US008865894B2

(12) United States Patent
Caravatti et al.

(10) Patent No.: US 8,865,894 B2
(45) Date of Patent: Oct. 21, 2014

(54) OXAZOLIDIN-2-ONE COMPOUNDS AND USES THEREOF

(71) Applicant: Novartis AG, Basel (CH)

(72) Inventors: Giorgio Caravatti, Bottmingen (CH); Robin Alec Fairhurst, Riehen (CH); Pascal Furet, Thann (FR); Frédéric Stauffer, Hesingue (FR); Frank Hans Seiler, Freiburg (DE); Clive McCarthy, Oxfordshire (GB); Heinrich Rueeger, Flueh (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/773,947

(22) Filed: Feb. 22, 2013

(65) Prior Publication Data

US 2013/0225574 A1    Aug. 29, 2013

Related U.S. Application Data

(60) Provisional application No. 61/736,707, filed on Dec. 13, 2012, provisional application No. 61/602,954, filed on Feb. 24, 2012.

(51) Int. Cl.
| | |
|---|---|
| C07D 401/14 | (2006.01) |
| A01N 43/54 | (2006.01) |
| C07D 403/04 | (2006.01) |
| C07D 413/14 | (2006.01) |
| A61K 31/5377 | (2006.01) |
| A61K 45/06 | (2006.01) |

(52) U.S. Cl.
CPC .......... *C07D 413/14* (2013.01); *A61K 31/5377* (2013.01); *A61K 45/06* (2013.01)
USPC .......................................... 544/122; 514/256

(58) Field of Classification Search
CPC .................................................. C07D 403/04
See application file for complete search history.

(56) References Cited

U.S. PATENT DOCUMENTS

| | | | |
|---|---|---|---|
| 3,975,384 A | 8/1976 | Narr | |
| 4,929,726 A | 5/1990 | Strekowski et al. | |
| 5,358,945 A | 10/1994 | Mizuchi et al. | |
| 5,786,355 A | 7/1998 | Konno et al. | |
| 5,976,758 A | 11/1999 | Fukui et al. | |
| 5,990,105 A | 11/1999 | Bos et al. | |
| 6,251,900 B1 | 6/2001 | Kawashima et al. | |
| 6,288,228 B1 | 9/2001 | Henkin et al. | |
| 6,495,558 B1 | 12/2002 | Armistead et al. | |
| 6,599,926 B2 | 7/2003 | Pinto et al. | |
| 6,603,000 B2 | 8/2003 | Yee et al. | |
| 6,743,788 B2 | 6/2004 | Cirillo et al. | |
| 6,846,928 B2 | 1/2005 | Bebbington et al. | |
| 7,045,519 B2 | 5/2006 | Nuss et al. | |
| 7,091,343 B2 | 8/2006 | Bebbington et al. | |
| 7,179,826 B2 | 2/2007 | Bebbington et al. | |
| 7,423,148 B2 | 9/2008 | Nuss et al. | |
| 7,566,712 B2 | 7/2009 | Bakthavatchalam et al. | |
| 7,652,009 B2 | 1/2010 | Kim et al. | |
| 7,767,669 B2 | 8/2010 | Nuss et al. | |
| 7,893,063 B2 | 2/2011 | Pass | |
| 7,957,951 B2 | 6/2011 | Foster et al. | |
| 8,173,647 B2 | 5/2012 | Atallah et al. | |
| 8,217,035 B2 | 7/2012 | Burger et al. | |
| 8,563,549 B2 | 10/2013 | Burger et al. | |
| 8,575,338 B2 | 11/2013 | Tsuzuki et al. | |
| 2004/0002496 A1 | 1/2004 | Bebbington et al. | |
| 2004/0009974 A1 | 1/2004 | Bebbington et al. | |
| 2004/0009981 A1 | 1/2004 | Bebbington et al. | |
| 2005/0014753 A1 | 1/2005 | Ding et al. | |
| 2009/0018134 A1 | 1/2009 | Pike et al. | |
| 2010/0048547 A1 | 2/2010 | Atallah et al. | |
| 2010/0249126 A1 | 9/2010 | Burger et al. | |
| 2011/0195966 A1 | 8/2011 | Garcia-Echeverria et al. | |
| 2012/0225859 A1 | 9/2012 | Burger et al. | |
| 2013/0123289 A1 | 5/2013 | Yang et al. | |
| 2013/0143862 A1 | 6/2013 | Ashcraft et al. | |
| 2013/0150368 A1 | 6/2013 | Ashcraft et al. | |
| 2013/0225574 A1 | 8/2013 | Caravatti et al. | |
| 2014/0135330 A1 | 5/2014 | Fairhurst et al. | |

FOREIGN PATENT DOCUMENTS

| | | |
|---|---|---|
| AU | 2010291318 | 3/2011 |
| DE | 2341925 A1 | 3/1975 |
| EP | 0 330 263 A1 | 8/1989 |
| EP | 0459830 A1 | 12/1991 |
| EP | 0767170 B1 | 10/2002 |
| EP | 1277738 A1 | 1/2003 |
| EP | 1277741 A1 | 1/2003 |
| EP | 2 394 999 A1 | 12/2011 |
| EP | 2 560 488 A1 | 2/2013 |

(Continued)

OTHER PUBLICATIONS

Amine, M. S. et al., "Utilities of 4-(4'Benzyl Phenyl)-6-Arylpyrimidine-2-Thiones for the Synthesis of Biologically Active Condensed and Non-Condensed Heterocycles", Egypt. J. Chem., 41, No. 1-6, pp. 267-276, 1998.
Angelo, M. et al., "Synthesis and Antifilarial Activity of N-[4-[[4-Alkoxy-3-[(dialkylamino)methyl]phenyl]amino]-2-pyrimidinyl]-N'-phenylguanidines", J. Med. Chem., 26, pp. 1258-1267, 1983.
Essawy, S.A. et al., "Some Reactions of 4-(2-Methoxynaphthyl)-6-(P-Chlorophenyl) Pyrimidin-2 (1H)-One and its Corresponding 2-Chloro Derivative", Egypt. J. Chem., 37, No. 4, pp. 413-421, 1994.
Kidwai, M. et al., "Base Catalysed Pyrimidine Synthesis Using Microwave", Bulletin of the Korean Chemical Society, 24(11), pp. 1575-1578, 2003, Caplus Abstract 2003:973238.
Kothari, Seema et al., "A Facile One Pot Conversion of 3',5'-Dibromo-4'-Hydroxy Substituted Chalcones to Pyrimidine Derivatives and their Antibacterial and Herbicidal Activity", Indian Journal of Heterocyclic Chemistry, vol. 8, Apr.-Jun. 1999, pp. 285-288.

(Continued)

*Primary Examiner* — Nyeemah A Grazier
(74) *Attorney, Agent, or Firm* — Scott W. Reid

(57) ABSTRACT

The present invention relates to oxazolidin-2-one substituted pyrimidine compounds that act as PI3K (phosphatidylinositol-3-kinase) inhibitors, as well as pharmaceutical compositions thereof, methods for their manufacture and uses for the treatment of conditions, diseases and disorders dependent on PI3K.

22 Claims, 12 Drawing Sheets

(56) References Cited

FOREIGN PATENT DOCUMENTS

| | | |
|---|---|---|
| EP | 2 563 365 A1 | 3/2013 |
| GB | 581334 | 10/1946 |
| GB | 2 431 156 A | 4/2007 |
| JP | 49-021148 B | 2/1974 |
| JP | 49-021149 B | 2/1974 |
| JP | 11-158073 A2 | 6/1999 |
| JP | 2001-089452 A | 4/2001 |
| WO | 89/00599 A1 | 1/1989 |
| WO | 99/19305 A2 | 4/1999 |
| WO | 99/65897 A1 | 12/1999 |
| WO | 00/43373 A2 | 7/2000 |
| WO | 01/00207 A1 | 1/2001 |
| WO | 01/00213 A1 | 1/2001 |
| WO | 01/00214 A1 | 1/2001 |
| WO | 01/05783 A1 | 1/2001 |
| WO | 01/60816 A1 | 8/2001 |
| WO | 01/72745 A1 | 10/2001 |
| WO | 01/83456 A1 | 11/2001 |
| WO | 02/20495 A2 | 3/2002 |
| WO | 02/22606 A1 | 3/2002 |
| WO | 02/22608 A1 | 3/2002 |
| WO | 02/36586 A1 | 5/2002 |
| WO | 0236586 A1 | 5/2002 |
| WO | 02/062766 A2 | 8/2002 |
| WO | 02/062789 A1 | 8/2002 |
| WO | 02/64096 A2 | 8/2002 |
| WO | 02/102313 A2 | 12/2002 |
| WO | 03/030909 A1 | 4/2003 |
| WO | 2004/000820 A2 | 12/2003 |
| WO | 2004/029204 A2 | 4/2004 |
| WO | 2004/032716 A2 | 4/2004 |
| WO | 2004/039788 A1 | 5/2004 |
| WO | 2004/048365 A1 | 6/2004 |
| WO | 2004/084824 A2 | 10/2004 |
| WO | 2004/092196 A2 | 10/2004 |
| WO | 2005/007648 A2 | 1/2005 |
| WO | 2005/009977 A1 | 2/2005 |
| WO | 2005/028444 A1 | 3/2005 |
| WO | 2005/099711 A1 | 10/2005 |
| WO | 2006/005914 A1 | 1/2006 |
| WO | 2006/026135 A2 | 3/2006 |
| WO | 2006/065872 A1 | 6/2006 |
| WO | 2006/071538 A2 | 7/2006 |
| WO | 2006/071960 A2 | 7/2006 |
| WO | 2006/078992 A2 | 7/2006 |
| WO | 2006/090167 A2 | 8/2006 |
| WO | 2006/113704 A2 | 10/2006 |
| WO | 2007/080382 A1 | 7/2007 |
| WO | 2007/084786 A1 | 7/2007 |
| WO | 2008/080937 A1 | 7/2008 |
| WO | 2008/098058 A1 | 8/2008 |
| WO | 2009/007748 A2 | 1/2009 |
| WO | 2009/066084 A1 | 5/2009 |
| WO | WO 2009066084 A1 * | 5/2009 |
| WO | 2009/109605 A1 | 9/2009 |
| WO | 2009/118324 A1 | 10/2009 |
| WO | 2009/120094 A2 | 10/2009 |
| WO | 2009/125870 A1 | 10/2009 |
| WO | 2010/020432 A2 | 2/2010 |
| WO | 2010/049481 A1 | 5/2010 |
| WO | 2010/052569 A2 | 5/2010 |
| WO | 2010/068863 A2 | 6/2010 |
| WO | 2010/090290 A1 | 8/2010 |
| WO | 2010/090344 A1 | 8/2010 |
| WO | 2010/105243 A1 | 9/2010 |
| WO | 2010/120994 A2 | 10/2010 |
| WO | 2010/135070 A1 | 11/2010 |
| WO | 2011/005119 A1 | 1/2011 |
| WO | 2011/017296 A1 | 2/2011 |
| WO | 2011/026835 A1 | 3/2011 |
| WO | 2011/031896 A2 | 3/2011 |
| WO | 2011/072174 A1 | 6/2011 |
| WO | 2011/114275 A1 | 9/2011 |
| WO | 2011/133888 A1 | 10/2011 |
| WO | 2011/143160 A2 | 11/2011 |
| WO | 2012/009678 A1 | 1/2012 |
| WO | 2012/044727 A2 | 4/2012 |
| WO | 2012/054535 A2 | 4/2012 |
| WO | 2012/055942 A1 | 5/2012 |
| WO | 2012/109423 A1 | 8/2012 |
| WO | 2012/171337 A1 | 12/2012 |
| WO | 2013/030368 A1 | 3/2013 |
| WO | 2013/046136 A1 | 4/2013 |
| WO | 2013/052395 A1 | 4/2013 |
| WO | 2013/173283 A1 | 11/2013 |
| WO | 2013/184621 A1 | 12/2013 |

OTHER PUBLICATIONS

Mikhaleva, M. A. et al., "Pyrimidines. 70. Relative Reactivities of the Chlorine Atoms of 2,2',4-Trichloro-4',5-Dipyrimidinyl in its Reaction with Piperdine", Chemistry of Heterocyclic Compounds (A Translation of Khimiyageterotsiklicheskikh Soedinenii), Plenum Press Co., New York, NY, US, vol. 15, No. 6, pp. 671-676, 1979.

Mokrosz, M. J. et al., "4-(3-Furyl)-2-(4-Methylpiperazino)Pyrimidines: Potent 5-HT2A Receptor Antagonists", Bioorganic & Medicinal Chemistry Letters, vol. 7, No. 13, pp. 1635-1638, 1997.

Sukhwal, Sudha et al., "A New Route to 2-Piperidino-4,6-Diarylpyrimidines", Indian Journal of Heterocyclic Chemistry, vol. 4, Jul.-Sep. 1994, pp. 67-68.

Ali, Khaled et al., "Essential role for the p110delta phosphoinositide 3-kinase in the allergic response" Nature, Oct. 21, 2004, pp. 1007-1011, vol. 431, Nature Publishing Group.

Andrisano, Renato "Pyrimidine. IV" Bollettino Scientifico della Facolta di Chimica Industriale di Bologna vol. 5, pp. 48-551, 1947, Volume Date 1944-1947. CA 44:19897, 1950 (1 page).

Banker, Gilbert S. et al., Modern Pharmaceutics 3rd Ed., Marcel Dekker, New York, 1996, pp. 451 and 596.

Bennet, J. Claude et al., Cecil Textbook of Medicine, 20th ed., W.B. Saunders, Philadelphia, 1996, Part XIV, Oncology, pp. 1004-1010.

Brown, Daniel M. et al., "Some Heterocyclic Analogues of Stilbenes", Journal of the Chemical Society, 1948, pp. 2147-2153.

Bundy, Gordon L., et al., "Synthesis of 2,4-Diaminopyrrolo[2,3-d]pyrimidines via Thermal Fischer Indolization. Pyrazole Formation with Ytterbium Triflate Catalysis", Journal of Heterocyclic Chemistry, vol. 37, pp. 1471-1477, Nov.-Dec. 2000.

Bundy, Gordon L., et al., "Synthesis of Novel 2,4-Diaminopyrrolo-[2,3-d]pyrimidines with Antioxidant, Neuroprotective, and Antiasthma Activity", Journal of Medicinal Chemistry vol. 38, pp. 4161-4163, Oct. 1995.

Buonamici, Silvia et al., "Interfering with Resistance to Smoothened Antagonists by Inhibition of the PI3K Pathway in Medulloblastoma", Sci Transl Med 2, vol. 2, Issue 51, pp. 1-8, 2010.

Cabaj, John E. et al., "Bromine-Mediated Addition of Nucleophiles to the Electron-Rich Pyrimidine Subunit of Tirilazad", Journal of Organic Chemistry vol. 59, No. 17, pp. 5090-5092, Aug. 1994.

Caine, Graham J. et al., "Coagulopathic Complications in Breast Cancer", vol. 98, No. 8, pp. 1578-1586, Oct. 2003.

Clayton, Elizabeth et al., "A Crucial Role for the p110delta Subunit of Phosphatidylinositol 3-Kinase in B Cell Development and Activation", J. Exp. Med., Sep. 9, 2002, pp. 753-763, vol. 196, No. 6, The Rockefeller University Press.

Crowder, Robert J. et al., "Treating breast cancer through novel inhibitors of the phosphatidylinositol 3'-kinase pathway", Breast Cancer Research, vol. 7, No. 5, pp. 212-214, Oct. 2005.

Falco, E.A. et al., "2, 4-Diaminopyrimidines. A new series of antimalarials", British Journal of Pharmacology and Chemotherapy vol. 6, pp. 185-200, Jun. 1951. CA 46:27482, 1952 (1 page).

Font, David et al., "Development of an Efficient and Straightforward Methodology Toward the Synthesis of Molecularly Diverse 2,6-Disubstituted 3,4-Dihydropyrimidin-4(3H)-ones", Synthesis, vol. 13, pp. 1833-1842, Sep. 2002.

Golub, T. R. et al., "Molecular Classification of Cancer: Class Discovery and Class Prediction by Gene Expression Monitoring", Science, vol. 286, pp. 531-537, 1999.

Jackson, Shaun P. et al., "PI 3-kinase p110beta: a new target for antithrombotic therapy", Nature Medicine, May 2005, vol. 11, No. 5, pp. 507-514, Nature Publishing Group.

(56) References Cited

OTHER PUBLICATIONS

Jaworska, Donna et al., Review of Methods for Assessing the Applicability Domains of SARS and QSARS, "SAR applicability domain" Sep. 27, 2004, pp. 1-8.
Jou, Shiann-Tarng et al., "Essential, Nonredundant Role for the Phosphoinositide 3-Kinase p110delta in Signaling by the B-Cell Receptor Complex", Molecular and Cellular Biology, Dec. 2002, pp. 8580-8591, vol. 22, No. 24, American Society for Microbiology.
Katiyar, Sanjay Babu et al., "Syntheses of 2,4,6-trisubstituted pyrimidine derivatives as a new class of antifilarial topoisomerase II inhibitors", Bioorganic & Medicinal Chemistry Letters, vol. 15, pp. 47-50, 2005.
Kothari, Seema et al., "A facile one pot conversion of 3',5'-dibromo-4'-hydroxy substituted chalcones to pyrimidine derivatives and their antibacterial and herbicidal activity", Indian Journal of Heterocyclic Chemistry, 8(4), pp. 285-288, 1999. CA 131:257250, 1999 (1 page).
Kowalewski, Andrzej et al., "Unfused Heterobicycles as Amplifiers of Phleomycin. IV 4,5'-Bipyrimidines with Dimethylamino and/or Dimethylaminoethylamino Substituents", Australian Journal of Chemistry, 34(12), pp. 2929-2933, 1981.
Lala, P. K. et al., "Role of nitric oxide in tumor progression: Lessons from experimental tumors" Cancer and Metastasis Reviews, 17(1), pp. 91-106, 1998.
Li, Shao Ying et al., "PIK3CA mutations in breast cancer are associated with poor outcome", Breast Cancer Research and Treatment (2006) 96, pp. 91-95.
Mamaev, V. P. et al., "Reaction kinetics of substituted 2-chloropyrimidines with piperidine", Reaktsionnaya Sposobnost Organicheskikh Soedinenii, 5(3) pp. 824-837, 1968. CA 70:76976, 1969 (1 page).
Mikhaleva, M. A. et al., "Pyrimidines. 70. Relative reactivity of the chlorine atoms of 2,2',4-trichloro-4',5-bipyrimidine in the reaction with piperidine", Khimiya Geterotsiklicheskikh Soedinenii, 6, pp. 821-826, 1979. CA 91:107951, 1979 (1 page).
Mokrosz, M.J. et al., "Structure-activity relationship studies of CNS agents. Part 25. 4,6-Di(heteroaryl)-2-(N-methylpiperazino) pyrimidines as new, potent 5-HT2A receptor ligands: a verification of the topographic model", Archiv der Pharmazie 328(9) pp. 659-666, 1995. CA 124:223, 1995 (1 page).
Nahta, Rita et al., "Signal Transduction Inhibitors in the Treatment of Breast Cancer", Curr. Med. Chem.—Anti-Cancer Agents, 2003, 3, pp. 201-216.
Ouf, A. A. Abou et al., "Preparation of Some Methyl Pyrimidines Expected to be Antimetabolites", Egyptian Journal of Pharmaceutical Science 14(2), pp. 180-195, 1973.
Patani, George A. et al., "Bioisosterism: A Rational Approach in Drug Design", Chem. Rev. 1996, vol. 96, No. 8, pp. 3147-3176.
Reif, Karin et al., "Cutting Edge: Differential Roles for Phosphoinositide 3-Kinases, p110gama and p110delta, in Lymphocyte Chemotaxis and Homing", J Immunol, 2004, vol. 173, pp. 2236-2240.
Sharma, P. et al., "A convenient one-pot synthesis of 2-substituted-4,6-diaryl pyrimidines", Indian Journal of Chemistry 38B, pp. 966-968, Aug. 1999. CA 132:207818, 2000 (1 page).
Silverman, Richard B., The Organic Chemistry of Drug Design and Drug Action 2nd ed., Elsevier Academic Press, 2004, pp. 29-34.
Sukhwal, S. et al., "A new route to 2-piperidino-4,6-diarylpyrimidines", Indian Journal of Heterocyclic Chemistry 4(1), pp. 67-68, 1994. CA 122:105796, 1995 (2 pages).
Tani, Hideo et al., "2,4,6-Trisubstituted pyrimidines", JP 49021148, May 30, 1974. CA 82:140173, 1975 (1 page).
Voskoglou-Nomikos, Theodora et al., "Clinical Predictive Value of the in Vitro Cell Line, Human Xenograft, and Mouse Allograft Preclinical Cancer Models", Clinical Cancer Research, vol. 9, pp. 4227-4239, 2003.
Wolff, Manfred E., Burger's Medicinal Chemistry and Drug Discovery, 5th ed., vol. 1, Wiley, New York, 1995, pp. 975-977.
Balant et al., Metabolic Considerations in Prodrug Design. Burger's Medicinal Chemistry and Drug Discovery. 1995;1:975-7.
Burger et al., Identification of NVP-BKM120 as a Potent, Selective, Orally Bioavailable Class I PI3 Kinase Inhibitor for Treating Cancer. ACS Med Chem Lett. 2011;2(10):774-9.
U.S. Appl. No. 14/208,015, filed Mar. 13, 2014.
U.S. Office Action for U.S. Appl. No. 14/069,400 mailed Feb. 28, 2014.
Amary et al., Ollier disease and Maffucci syndrome are caused by somatic mosaic mutations of IDH1 and IDH2. Nat Genet. Nov. 6, 2011;43(12):1262-5.
Balss et al., Analysis of the IDH1 codon 132 mutation in brain tumors. Acta Neuropathol. Dec. 2008;116(6):597-602. Epub Nov. 5, 2008.
Dang et al., Cancer-associated IDH1 mutations produce 2-hydroxyglutarate. Nature. Dec. 10, 2009;462(7274):739-44.
Dang et al., IDH mutations in glioma and acute myeloid leukemia. Trends Mol Med. Sep. 2010;16(9):387-97. Epub Aug. 5, 2010.
Gaal et al., Isocitrate dehydrogenase mutations are rare in pheochromocytomas and paragangliomas. J Clin Endocrinol Metab. Mar. 2010; 95(3):1274-8. Epub Nov. 13, 2009.
Gross et al., Cancer-associated metabolite 2-hydroxyglutarate accumulates in acute myelogenous leukemia with isocitrate dehydrogenase 1 and 2 mutations. J Exp Med. Feb. 15, 2010;207(2):339-44. Epub Feb 8, 2010.
Hayden et al., Frequent IDH1 mutations in supratentorial primitive neuroectodermal tumors (sPNET) of adults but not children. Cell Cycle. Jun. 1, 2009;8(11):1806-7. Epub Jun. 30, 2010.
Kranendijket et al., IDH2 mutations in patients with D-2-hydroxyglutaric aciduria. Science. Oct. 15, 2010;330(6002):336. Epub Sep. 16, 2010.
Pansuriya et al., Somatic mosaic IDH1 and IDH2 mutations are associated with enchondroma and spindle cell hemangioma in Ollier disease and Maffucci syndrome. Nat Genet. Nov. 6, 2011;43(12):1256-61.
Sellner et al., Increased levels of 2-hydroxyglutarate in AML patients with IDH1-R132H and IDH2-R140Q mutations. Eur J Haematol. Nov. 2010;85(5):457-9.
Shibata et al., Mutant IDH1 confers an in vivo growth in a melanoma cell line with BRAF mutation. Am J Pathol. Mar. 2011;178(3):1395-402.

\* cited by examiner

OXAZOLIDIN-2-ONE COMPOUNDS AND USES THEREOF

FIELD OF THE INVENTION

The present invention relates to oxazolidin-2-one substituted pyrimidine compounds that act as PI3K (phosphatidylinositol-3-kinase) inhibitors, as well as pharmaceutical compositions thereof, methods for their manufacture and uses for the treatment of conditions, diseases and disorders dependent on PI3K.

BACKGROUND OF THE INVENTION

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate (PIP$_2$) and phosphoinositol-3,4,5-triphosphate (PIP$_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423 (1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers (Kang at el., *Proc. Natl. Acad. Sci. USA* 102:802 (2005); Samuels et al., *Science* 304:554 (2004); Samuels et al., *Cancer Cell* 7:561-573 (2005)).

In some tumors the p110δ isoform, PIK3CB is amplified or over-expressed. In addition, studies indicate that tumors driven by PTEN loss may be sensitive to p110β rather than p110α. (Jia et al., *Nature,* 454:776-779 (2008). Wee et al., *PNAS* 105 (35), 13057-13062 (2008); Liu et al., *Nature Rev. Drug Discovery* 8:627-644 (2009)).

Both p110δ and p110γ are expressed primarily in the hematopoietic system and appear to play significant roles in leukocyte signalling (Liu et al. *Blood* 110(4), 1191-1198 (2007)). However, they do also play roles in some cancers (Knobbe et al., *Brain Pathol.* 13, 507-518 (2003); Kang et al. *PNAS* 103(5), 1289-1294 (2006)). p110δ expression is restricted to leukocytes pointing to its potential role in leukocyte-mediated diseases (Vanhaesebroeck et al. *PNAS* 94(9), 4330-4335 (1997)). p110δ is upregulated in blast cells in patients with acute myeloid leukaemia, where it plays a key role in cell survival (Sujobert et al., *Blood* 106(3), 1063-1066 (2005)) indicating its potential as a target in leukaemia and other haematological malignancies. p110δ activation plays an important role in the development of B-cell malignancies and therefore inhibition of p110δ could be used to treat B-cell malignancies such as chronic lymphocytic leukemia (CLL), non-Hodgkin's lymphoma (NHL), plasma cell myeloma and Hodgkin's lymphoma (NH) Castillo et al., *Expert Opin. Investig. Drugs* 21, 15-22 (2012)).

These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey at el., *Nature Rev. Drug Disc.* 4:988-1004 (2005)).

Published international patent application WO2007/084786 describes substituted pyrimidine molecules that inhibit PI3K.

SUMMARY OF THE INVENTION

There remains a need for compounds that inhibit the activity of more than one of the Class I PI3K isoforms (alpha, beta, delta and gamma), because such compounds are considered to have the ability to avoid adaption mechanisms due to pathway rewiring through the other isoforms, compared to compounds with unique specificity, e.g. specificity for one member of the PI3K Class I family.

Increased inhibition potency of at least one of the PI3K isoforms (i.e. inhibit at least one PI3K isoform at lower concentrations, especially one or both of the alpha and beta isoforms) may also be advantageous. In the case of PTEN null tumors, for example, although the driving isoform is p110b, complete efficacy could require participation of the other ClassIA isoforms. There is also a need for compounds which potently inhibit PI3Kalpha kinase, e.g. for the treatment of cancers that are primarily driven by oncogenic forms of the gene encoding p110a (e.g. PIK3CA H1047R or E545K), as well as tumors showing increased copy number of PIK3CA.

Compounds which show selective inhibition in favour of one or more PI3K isoforms (for example at least two, preferably three of the alpha, beta, delta and gamma isoforms, e.g. the alpha, beta and delta isoforms) compared to mTOR are also desirable, as the mTOR inhibitory effect generally reduces the safety window, more especially when the compound inhibits mTOR more strongly than PI3K (unfavorable ratio).

Furthermore, PI3K inhibitors which have a reduced, in particular, do not possess an off-target effect, such as tubulin binding, are desired, as such effect can cause toxicity effects not connected with the on-target PI3K inhibition and therefore such compounds may require additional careful dosing control to ensure the therapeutic effect is controllable and attributable to PI3K inhibition. Hence there is a need for compounds which have a reduced or weak off-target effect or do not have off-target effect.

Desirably compounds displaying an improved inhibition of at least one (e.g. PI3Kalpha), but especially two (e.g. PI3Kalpha and PI3Kbeta) or three (e.g. PI3Kalpha, PI3Kbeta and PI3Kdelta), or all four class 1 PI3Ks (PI3Kalpha, PI3Kbeta, PI3Kdelta and PI3Kgamma) as well as a reduced (in particular, an absence of) off-target effect are sought.

The present invention provides compounds and pharmaceutical compositions thereof which compounds are PI3K inhibitors. The invention also provides combinations comprising those compounds. The invention further provides the compounds of the invention for use in methods of treating, preventing or ameliorating a PI3K mediated disease such as cancer, comprising administering to a subject in need thereof an effective amount of a PI3K inhibiting compound of the invention. The invention also provides intermediates useful in the preparation of the compounds of the invention.

The present invention provides in one aspect a compound of Formula (I)

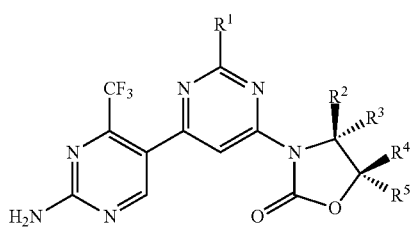

(I)

wherein,
$R^1$ is

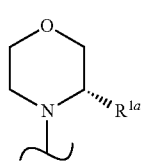

wherein $R^{1a}$ is H or —CH$_3$
or $R^1$ is

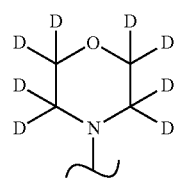

wherein D is deuterium; and
$R^2$ is H;
$R^3$ is H; and
$R^4$ is H, and $R^5$ is —CH$_3$ or —CH$_2$OH; or
$R^4$ is —CH$_2$OH, and $R^5$ is H;
or
$R^2$ is —CH$_3$, —CH$_2$OH, —CH$_2$OCH$_3$, —CH$_2$CH$_2$OH or —CH$_2$OC(O)H;
$R^3$ is H; and
$R^4$ is —CH$_3$, —CH$_2$OH, —CH$_2$CH$_2$OH, —CH$_2$CH(OH)CH$_3$ or —CH$_2$C(OH)(CH$_3$)$_2$ and $R^5$ is H, or
$R^4$ is H, and $R^5$ is —CH$_3$, —CH$_2$OH, —CH$_2$CH(OH)CH$_3$ or —CH$_2$C(OH)(CH$_3$)$_2$, or
$R^4$ is H or —CH$_3$ and $R^5$ is H or —CH$_3$;
or
$R^3$ is H;
$R^4$ is H;
$R^2$ and $R^5$ are joined and form —(CH$_2$)$_4$—;
or
$R^4$ is H and $R^5$ is H; and
$R^2$ is —CH$_2$OH, and $R^3$ is —CH$_3$; or
$R^2$ is H or —CH$_3$, and $R^3$ is —CH$_2$OH;
or
$R^2$ is H and $R^4$ is H; and
$R^3$ and $R^5$ are joined and form the group

or the group

or
$R^3$ is H and $R^5$ is H; and
$R^2$ and $R^4$ are joined and form the group

or a pharmaceutically acceptable salt thereof.

The wavy line indicates the point of attachment of the morpholine and also where present, the point of attachment of other shown groups, to the rest of the molecule.

The compounds of formula (I) are considered suitable, for example, to be used in the treatment of diseases dependent on PI3 kinase, especially proliferative diseases such as cancer, e.g. tumor diseases.

The invention may be more fully appreciated by reference to the following description, including the mentioned definitions and the concluding examples. The described embodiments are to be taken independently, collectively or in any combination unless otherwise stated. As used herein, the terms "including", "containing" and "comprising" are used herein in their open, non-limiting sense.

Unless specified otherwise, the term "compounds of the present invention" or "a compound of the present invention" and the like refers to compounds of formula (I) and subformulae thereof (e.g. formulae (IA) and (IA')), and salts of the compounds, as well as isotopically labeled compounds (including deuterium substitutions).

The compounds of the invention have the stereochemistry depicted in formula (I) and subformulae thereof unless stated otherwise.

DETAILED DESCRIPTION

Figure 1:
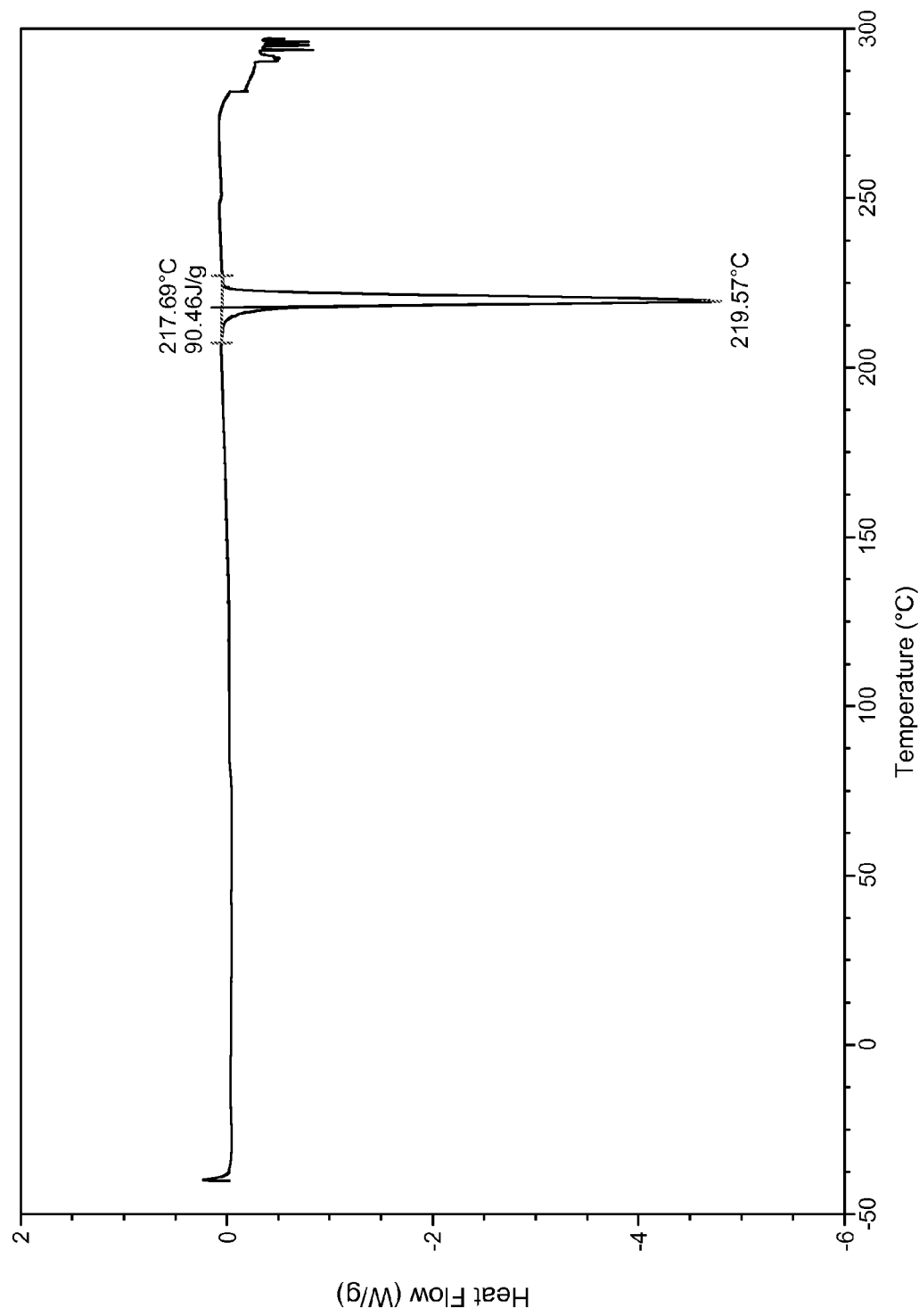
FIG. 1 is the differential Scanning calorimetry graph of the crystalline material of Example 10.

Various embodiments of the invention are described herein. It will be recognized that features specified in each embodiment may be combined with other specified features to provide further embodiments of the present invention. Various (enumerated) embodiments of the invention are also described herein.

The present invention provides in one aspect a compound according to formula (I):

wherein,
$R^1$ is wherein $R^{1a}$ is H or —$CH_3$
or $R^1$ is wherein D is deuterium;
$R^2$ is H;
$R^3$ is H; and
$R^4$ is H, and $R^5$ is —$CH_3$ or —$CH_2OH$; or
$R^4$ is —$CH_2OH$, and $R^5$ is H;
or
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$, —$CH_2OH$, —$CH_2CH_2OH$, —$CH_2CH(OH)CH_3$ or —$CH_2C(OH)(CH_3)_2$ and $R^5$ is H, or
$R^4$ is H, and $R^5$ is —$CH_3$, —$CH_2OH$, —$CH_2CH(OH)CH_3$ or —$CH_2C(OH)(CH_3)_2$, or
$R^4$ is H or —$CH_3$, and $R^5$ is H or —$CH_3$;
or
$R^3$ is H;
$R^4$ is H;
$R^2$ and $R^5$ are joined and form —$(CH_2)_4$—;
or
$R^4$ is H;
$R^5$ is H; and
$R^2$ is —$CH_2OH$, and $R^3$ is —$CH_3$; or
$R^2$ is H or —$CH_3$, and $R^3$ is —$CH_2OH$;
or
$R^2$ is H;
$R^4$ is H; and
$R^3$ and $R^5$ are joined and form the group or the group or
$R^3$ is H;
$R^5$ is H; and
$R^2$ and $R^4$ are joined and form the group or a pharmaceutically acceptable salt thereof.

In a preferred embodiment of that aspect, there is provided a compound according to formula (I) wherein, R¹ is

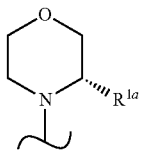

wherein R$^{1a}$ is H or —CH$_3$
or R¹ is

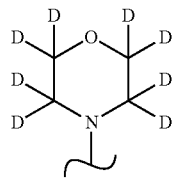

wherein D is deuterium;
R² is H;
R³ is H; and
R⁴ is H, and R⁵ is —CH$_3$ or —CH$_2$OH; or
R⁴ is —CH$_2$OH, and R⁵ is H;
or
R² is —CH$_3$, —CH$_2$OH, —CH$_2$OCH$_3$, —CH$_2$CH$_2$OH or —CH$_2$OC(O)H;
R³ is H;
R⁴ is —CH$_3$, —CH$_2$OH, —CH$_2$CH$_2$OH, —CH$_2$CH(OH)CH$_3$ or —CH$_2$C(OH)(CH$_3$)$_2$ and R⁵ is H, or
R⁴ is H, and R⁵ is —CH$_3$ or —CH$_2$OH, or
R⁴ is H or —CH$_3$ and R⁵ is H or —CH$_3$;
or
R³ is H;
R⁴ is H;
R² and R⁵ are joined and form —(CH$_2$)$_4$—; or
R⁴ is H;
R⁵ is H; and
R² is —CH$_2$OH, and R³ is —CH$_3$; or
R² is H or —CH$_3$, and R³ is —CH$_2$OH;
or
R² is H;
R⁴ is H; and
R³ and R⁵ are joined and form the group

or the group

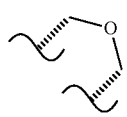

or
R³ is H;
R⁵ is H; and
R² and R⁴ are joined and form the group

or a pharmaceutically acceptable salt thereof.

In a more preferred embodiment of that aspect, there is provided a compound according to formula (I) wherein, R¹ is

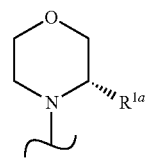

wherein R$^{1a}$ is H or —CH$_3$
or R¹ is

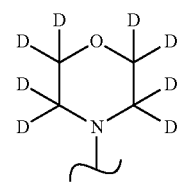

wherein D is deuterium;
R² is H;
R³ is H; and
R⁴ is H, and R⁵ is —CH$_3$ or —CH$_2$OH; or
R⁴ is —CH$_2$OH, and R⁵ is H;
or
R² is —CH$_3$, —CH$_2$OH, —CH$_2$OCH$_3$, —CH$_2$CH$_2$OH or —CH$_2$OC(O)H;
R³ is H;
R⁴ is —CH$_3$, —CH$_2$OH, —CH$_2$CH$_2$OH, —CH$_2$CH(OH)CH$_3$ or —CH$_2$C(OH)(CH$_3$)$_2$ and R⁵ is H, or
R⁴ is H, and R⁵ is —CH$_3$ or —CH$_2$OH, or
R⁴ is H or —CH$_3$ and R⁵ is H or —CH$_3$;
or
R³ is H;
R⁴ is H;
R² and R⁵ are joined and form —(CH$_2$)$_4$—;
or
R⁴ is H;
R⁵ is H; and
R² is —CH$_2$OH, and R³ is —CH$_3$; or
R² is H or —CH$_3$, and R³ is —CH$_2$OH;
or a pharmaceutically acceptable salt thereof.

In a further preferred embodiment, there is provided a compound of Formula (I)

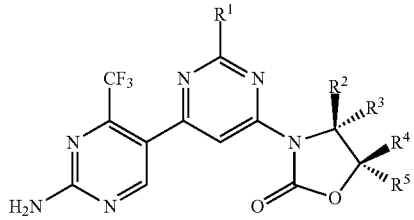

wherein,
R¹ is

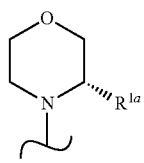

wherein R$^{1a}$ is H or —CH$_3$
or R¹ is

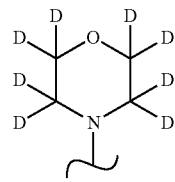

wherein D is deuterium;
R² is H;
R³ is H; and
R⁴ is H, and R⁵ is —CH$_3$ or —CH$_2$OH; or
R⁴ is —CH$_2$OH, and R⁵ is H;
or
R² is —CH$_3$, —CH$_2$OH, —CH$_2$OCH$_3$, —CH$_2$CH$_2$OH or —CH$_2$OC(O)H;
R³ is H;
R⁴ is —CH$_3$, —CH$_2$OH or —CH$_2$CH$_2$OH, and R⁵ is H, or
R⁴ is H, and R⁵ is —CH$_3$ or —CH$_2$OH, or
R⁴ is H or —CH$_3$ and R⁵ is H or —CH$_3$;
or
R³ is H;
R⁴ is H; and
R² and R⁵ are joined and form —(CH$_2$)$_4$—;
or
R⁴ is H;
R⁵ is H; and
R² is —CH$_2$OH, and R³ is —CH$_3$; or
R² is H or —CH$_3$, and R³ is —CH$_2$OH,
or a pharmaceutically acceptable salt thereof.

In a further alternative preferred embodiment, there is provided a compound according to Formula (I)

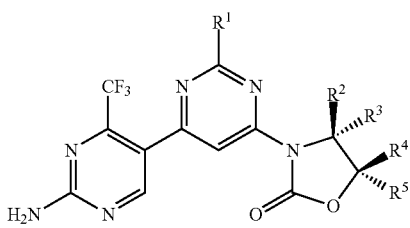

wherein,
R¹ is

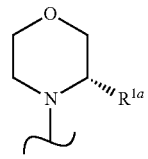

wherein R$^{1a}$ is H or —CH$_3$
or R¹ is

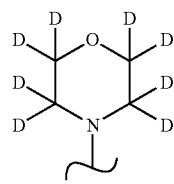

wherein D is deuterium;
R² is H;
R³ is H; and
R⁴ is H, and R⁵ is —CH$_3$ or —CH$_2$OH; or
R⁴ is —CH$_2$OH, and R⁵ is H;
or
R² is —CH$_3$, —CH$_2$OH, —CH$_2$OCH$_3$, —CH$_2$CH$_2$OH or —CH$_2$OC(O)H;
R³ is H;
R⁴ is —CH$_3$ or —CH$_2$OH, and R⁵ is H, or
R⁴ is H, and R⁵ is —CH$_3$ or —CH$_2$OH, or
R⁴ is H or —CH$_3$ and R⁵ is H or —CH$_3$;
or
R³ is H;
R⁴ is H;
R² and R⁵ are joined and form —(CH$_2$)$_4$—;
or
R⁴ is H;
R⁵ is H; and
R² is —CH$_2$OH, and R³ is —CH$_3$; or
R² is H or —CH$_3$, and R³ is —CH$_2$OH,
or a pharmaceutically acceptable salt thereof.

With respect to formula (I) in any one of the above-mentioned embodiments, the following detailed description is provided.

R$^{1a}$

In an embodiment, R$^{1a}$ is H.
In another embodiment R$^{1a}$ is —CH$_3$.
In a preferred embodiment R$^{1a}$ is H.

Further embodiments of the present invention are described below.

In an embodiment,
$R^1$ is

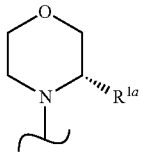

wherein $R^{1a}$ is H or —$CH_3$
or $R^1$ is

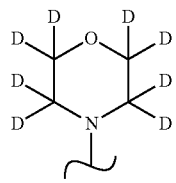

wherein D is deuterium;
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$, —$CH_2OH$ or —$CH_2CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$;
or
$R^3$ is H;
$R^4$ is H; and
$R^2$ and $R^5$ is —$(CH_2)_4$—;
or
$R^4$ is H;
$R^5$ is H; and
$R^2$ is —$CH_2OH$, and $R^3$ is —$CH_3$; or
$R^2$ is H or —$CH_3$, and $R^3$ is —$CH_2OH$,
or a pharmaceutically acceptable salt thereof.

In another embodiment,
$R^1$ is

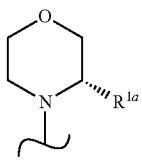

wherein $R^{1a}$ is H or —$CH_3$
or $R^1$ is

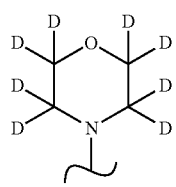

wherein D is deuterium;
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$, —$CH_2OH$ or —$CH_2CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$;
or
$R^4$ is H;
$R^5$ is H; and
$R^2$ is —$CH_2OH$, and $R^3$ is —$CH_3$; or
$R^2$ is H or —$CH_3$, and $R^3$ is —$CH_2OH$,
or a pharmaceutically acceptable salt thereof.

In yet a further embodiment,
$R^1$ is

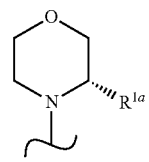

wherein $R^{1a}$ is H or —$CH_3$
or $R^1$ is

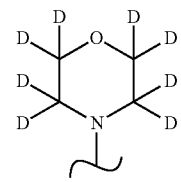

wherein D is deuterium;
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$, —$CH_2OH$ or —$CH_2CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In yet a further embodiment,
$R^1$ is

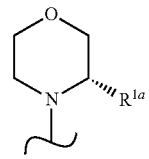

wherein $R^{1a}$ is H or —$CH_3$
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$, —$CH_2OH$ or —$CH_2CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In another embodiment,
R¹ is

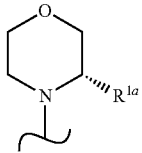

wherein R$^{1a}$ is H or —CH$_3$
R² is —CH$_3$ or —CH$_2$OH;
R³ is H;
R⁴ is —CH$_3$, —CH$_2$OH or —CH$_2$CH$_2$OH, and R⁵ is H, or
R⁴ is H, and R⁵ is —CH$_3$ or —CH$_2$OH, or
R⁴ is H or —CH$_3$ and R⁵ is H or —CH$_3$,
or a pharmaceutically acceptable salt thereof.
In another embodiment, preferably,
R¹ is

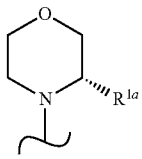

wherein R$^{1a}$ is H or —CH$_3$
R² is —CH$_3$ or —CH$_2$OH;
R³ is H;
R⁴ is —CH$_3$, —CH$_2$OH or —CH$_2$CH$_2$OH and R⁵ is H or
R⁴ is H and R⁵ is CH$_3$ or —CH$_2$OH,
or a pharmaceutically acceptable salt thereof.
In another embodiment, preferably,
R¹ is

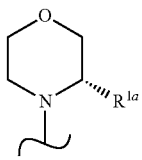

wherein R$^{1a}$ is H or —CH$_3$
R² is —CH$_3$ or —CH$_2$OH;
R³ is H;
R⁴ is —CH$_3$ or —CH$_2$CH$_2$OH, and
R⁵ is H,
or a pharmaceutically acceptable salt thereof.
In an embodiment,
R¹ is

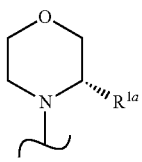

wherein R$^{1a}$ is H or —CH$_3$ or R¹ is

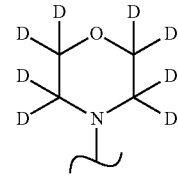

wherein D is deuterium;
R² is —CH$_3$, —CH$_2$OH, —CH$_2$OCH$_3$, —CH$_2$CH$_2$OH or —CH$_2$OC(O)H;
R³ is H;
R⁴ is —CH$_3$ or —CH$_2$OH, and R⁵ is H, or
R⁴ is H, and R⁵ is —CH$_3$ or —CH$_2$OH, or
R⁴ is H or —CH$_3$ and R⁵ is H or —CH$_3$;
or
R³ is H;
R⁴ is H;
R² and R⁵ is —(CH$_2$)$_4$—;
or
R⁴ is H;
R⁵ is H; and
R² is —CH$_2$OH, and R³ is —CH$_3$; or
R² is H or —CH$_3$, and R³ is —CH$_2$OH,
or a pharmaceutically acceptable salt thereof.
In another embodiment,
R¹ is

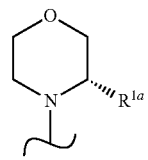

wherein R$^{1a}$ is H or —CH$_3$
or R¹ is

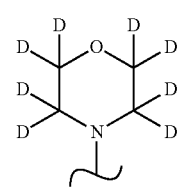

wherein D is deuterium;
R² is —CH$_3$, —CH$_2$OH, —CH$_2$OCH$_3$, —CH$_2$CH$_2$OH or —CH$_2$OC(O)H;
R³ is H;
R⁴ is —CH$_3$ or —CH$_2$OH, and R⁵ is H, or
R⁴ is H, and R⁵ is —CH$_3$ or —CH$_2$OH, or
R⁴ is H or —CH$_3$ and R⁵ is H or —CH$_3$;
or
R⁴ is H;
R⁵ is H; and
R² is —CH$_2$OH, and R³ is —CH$_3$; or
R² is H or —CH$_3$, and R³ is —CH$_2$OH,
or a pharmaceutically acceptable salt thereof.

In yet a further embodiment,
$R^1$ is

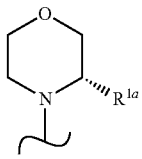

wherein $R^{1a}$ is H or —$CH_3$
or $R^1$ is

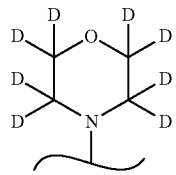

wherein D is deuterium;
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$ or —$CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In yet a further embodiment,
$R^1$ is

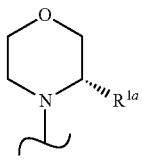

wherein $R^{1a}$ is H or —$CH_3$
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$ or —$CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In another embodiment,
$R^1$ is

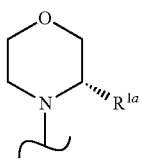

wherein $R^{1a}$ is H or —$CH_3$
$R^2$ is —$CH_3$ or —$CH_2OH$;
$R^3$ is H;
$R^4$ is —$CH_3$ or —$CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In another embodiment, preferably,
$R^1$ is

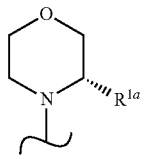

wherein $R^{1a}$ is H or —$CH_3$
$R^2$ is —$CH_3$ or —$CH_2OH$;
$R^3$ is H;
$R^4$ is —$CH_3$ or —$CH_2OH$ and $R^5$ is H or
$R^4$ is H and $R^5$ is $CH_3$ or —$CH_2OH$,
or a pharmaceutically acceptable salt thereof.

In another embodiment, preferably,
$R^1$ is

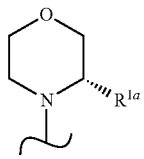

wherein $R^{1a}$ is H or —$CH_3$
$R^2$ is —$CH_3$ or —$CH_2OH$;
$R^3$ is H;
$R^4$ is —$CH_3$, and
$R^5$ is H,
or a pharmaceutically acceptable salt thereof.

In another preferred embodiment,
$R^1$ is

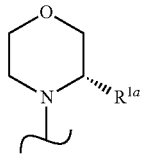

wherein $R^{1a}$ is H or —$CH_3$
$R^2$ is —$CH_2OH$;
$R^3$ is H;
$R^4$ is —$CH_3$, and
$R^5$ is H,
or a pharmaceutically acceptable salt thereof.

In an embodiment, compounds of the following formula (IA') are provided:

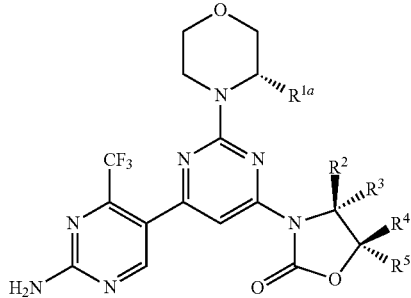

(IA')

wherein $R^{1a}$, $R^2$, $R^3$, $R^4$ and $R^5$, are as described in any of the above-mentioned embodiments.

In an embodiment, $R^{1a}$ may be hydrogen, thus providing compounds of the following formula (IA):

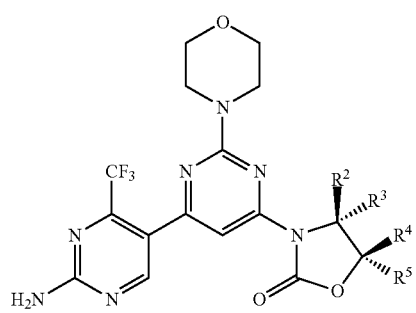

(IA)

wherein,
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$, —$CH_2OH$ or —$CH_2CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In an embodiment of compounds of formula (IA),
$R^2$ is —$CH_3$ or —$CH_2OH$;
$R^3$ is H;
$R^4$ is —$CH_3$, —$CH_2OH$ or —$CH_2CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In another embodiment of compounds of formula (IA),
$R^2$ is —$CH_3$ or —$CH_2OH$;
$R^3$ is H;
$R^4$ is —$CH_3$, —$CH_2OH$ or —$CH_2CH_2OH$ and $R^5$ is H or
$R^4$ is H and $R^5$ is $CH_3$ or —$CH_2OH$,
or a pharmaceutically acceptable salt thereof.

In another embodiment of compounds of formula (IA),
$R^2$ is —$CH_3$ or —$CH_2OH$;
$R^3$ is H;
$R^4$ is —$CH_3$ or —$CH_2CH_2OH$ and
$R^5$ is H,
or a pharmaceutically acceptable salt thereof.

In another embodiment of compounds of formula (IA),
$R^2$ is —$CH_3$;
$R^3$ is H;
$R^4$ is —$CH_2CH_2OH$, and
$R^5$ is H,
or a pharmaceutically acceptable salt thereof.

Alternatively, in an embodiment where $R^{1a}$ may be hydrogen, compounds of the following formula (IA) are provided:

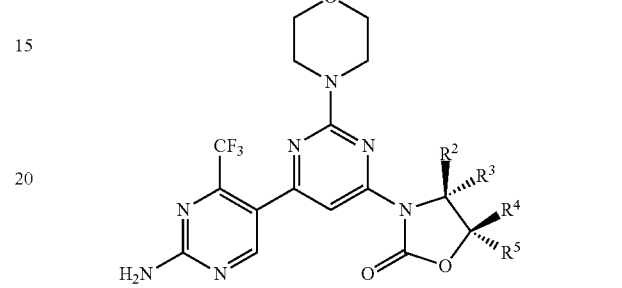

(IA)

wherein,
$R^2$ is —$CH_3$, —$CH_2OH$, —$CH_2OCH_3$, —$CH_2CH_2OH$ or —$CH_2OC(O)H$;
$R^3$ is H;
$R^4$ is —$CH_3$ or —$CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In an embodiment of compounds of formula (IA),
$R^2$ is —$CH_3$ or —$CH_2OH$;
$R^3$ is H;
$R^4$ is —$CH_3$ or —$CH_2OH$, and $R^5$ is H, or
$R^4$ is H, and $R^5$ is —$CH_3$ or —$CH_2OH$, or
$R^4$ is H or —$CH_3$ and $R^5$ is H or —$CH_3$,
or a pharmaceutically acceptable salt thereof.

In another embodiment of compounds of formula (IA),
$R^2$ is —$CH_3$ or —$CH_2OH$;
$R^3$ is H;
$R^4$ is —$CH_3$ or —$CH_2OH$ and $R^5$ is H or
$R^4$ is H and $R^5$ is $CH_3$ or —$CH_2OH$,
or a pharmaceutically acceptable salt thereof.

In another embodiment of compounds of formula (IA),
$R^2$ is —$CH_3$ or —$CH_2OH$;
$R^3$ is H;
$R^4$ is —$CH_3$, and
$R^5$ is H,
or a pharmaceutically acceptable salt thereof.

In a preferred embodiment of compounds of formula (IA),
$R^2$ is —$CH_2OH$;
$R^3$ is H;
$R^4$ is —$CH_3$, and
$R^5$ is H,
or a pharmaceutically acceptable salt thereof.

Further embodiments (enumerated) are provided as follows:

Embodiment 1

A compound of Formula (I)

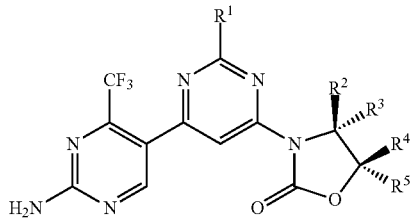

wherein,
R¹ is

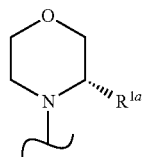

wherein R$^{1a}$ is H or —CH$_3$
or R¹ is

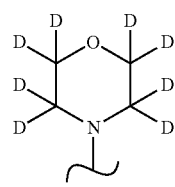

wherein D is deuterium;
R² and R³ is H;
R⁴ is H, and R⁵ is —CH$_3$ or —CH$_2$OH; or
R⁴ is —CH$_2$OH, and R⁵ is H;
or
R² is —CH$_3$, —CH$_2$OH, —CH$_2$OCH$_3$, —CH$_2$CH$_2$OH or —CH$_2$OC(O)H;
R³ is H;
R⁴ is —CH$_3$, —CH$_2$OH, —CH$_2$CH$_2$OH, —CH$_2$CH(OH)CH$_3$ or —CH$_2$C(OH)(CH$_3$)$_2$ and R⁵ is H, or
R⁴ is H, and R⁵ is —CH$_3$, —CH$_2$OH, —CH$_2$CH(OH)CH$_3$ or —CH$_2$C(OH)(CH$_3$)$_2$, or
R⁴ is H or —CH$_3$ and R⁵ is H or —CH$_3$;
or
R³ is H;
R⁴ is H;
R² and R⁵ are joined and form —(CH$_2$)$_4$—;
or
R⁴ is H;
R⁵ is H; and
R² is —CH$_2$OH, and R³ is —CH$_3$; or
R² is H or —CH$_3$, and R³ is —CH$_2$OH;
or
R² is H;
R⁴ is H; and
R³ and R⁵ are joined and form the group

or the group

or
R³ is H;
R⁵ is H; and
R² and R⁴ are joined and form the group

or a pharmaceutically acceptable salt thereof.

Embodiment 2

A compound according to Embodiment 1, wherein,
R² is —CH$_3$, —CH$_2$OH, —CH$_2$OCH$_3$, —CH$_2$CH$_2$OH or —CH$_2$OC(O)H;
R³ is H;
R⁴ is —CH$_3$, —CH$_2$OH or —CH$_2$CH$_2$OH, and R⁵ is H, or
R⁴ is H, and R⁵ is —CH$_3$ or —CH$_2$OH, or
R⁴ is H or —CH$_3$ and R⁵ is H or —CH$_3$;
or
R³ is H;
R⁴ is H;
R² and R⁵ is —(CH$_2$)$_4$—;
or
R⁴ is H;
R⁵ is H; and
R² is —CH$_2$OH, and R³ is —CH$_3$; or
R² is H or —CH$_3$, and R³ is —CH$_2$OH,
or a pharmaceutically acceptable salt thereof.

Embodiment 3

A compound according to Embodiment 1 or Embodiment 2, wherein
R² is —CH$_3$, —CH$_2$OH, —CH$_2$OCH$_3$, —CH$_2$CH$_2$OH or —CH$_2$OC(O)H;
R³ is H;
R⁴ is —CH$_3$, —CH$_2$OH or —CH$_2$CH$_2$OH, and R⁵ is H, or
R⁴ is H, and R⁵ is —CH$_3$ or —CH$_2$OH, or
R⁴ is H or —CH$_3$ and R⁵ is H or —CH$_3$;
or
R⁴ is H;
R⁵ is H; and
R² is —CH$_2$OH, and R³ is —CH$_3$; or
R² is H or —CH$_3$, and R³ is —CH$_2$OH,
or a pharmaceutically acceptable salt thereof.

Embodiment 4

A compound according to any one of Embodiments 1 to 3, wherein
$R^2$ is —CH$_3$, —CH$_2$OH, —CH$_2$OCH$_3$, —CH$_2$CH$_2$OH or —CH$_2$OC(O)H;
$R^3$ is H;
$R^4$ is —CH$_3$, —CH$_2$OH or —CH$_2$CH$_2$OH, and $R^5$ is H, or
$R^4$ is H, and $R^5$ is —CH$_3$ or —CH$_2$OH, or
$R^4$ is H or —CH$_3$ and $R^5$ is H or —CH$_3$,
or a pharmaceutically acceptable salt thereof.

Embodiment 5

A compound according to any one of Embodiments 1 to 4, of formula (IA')

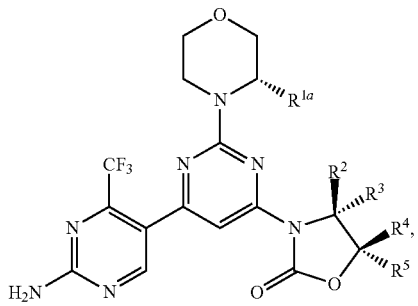

(IA')

wherein $R^{1a}$ is H or —CH$_3$,
or a pharmaceutically acceptable salt thereof.

Embodiment 6

A compound according to Embodiment 1, of formula (IA):

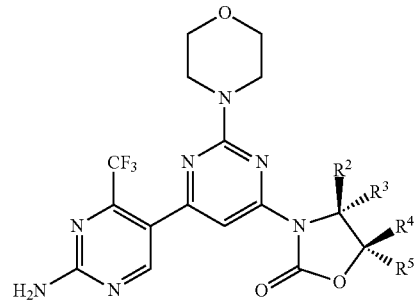

(IA)

wherein,
$R^2$ is —CH$_3$, —CH$_2$OH, —CH$_2$OCH$_3$, —CH$_2$CH$_2$OH or —CH$_2$OC(O)H;
$R^3$ is H;
$R^4$ is —CH$_3$, —CH$_2$OH or —CH$_2$CH$_2$OH, and $R^5$ is H, or
$R^4$ is H, and $R^5$ is —CH$_3$ or —CH$_2$OH, or
$R^4$ is H or —CH$_3$ and $R^5$ is H or —CH$_3$,
or a pharmaceutically acceptable salt thereof.

Embodiment 7

A compound according to Embodiment 6, wherein
$R^2$ is —CH$_3$ or —CH$_2$OH;
$R^3$ is H;
$R^4$ is —CH$_3$, —CH$_2$OH or —CH$_2$CH$_2$OH, and $R^5$ is H, or
$R^4$ is H, and $R^5$ is —CH$_3$ or —CH$_2$OH, or
$R^4$ is H or —CH$_3$ and $R^5$ is H or —CH$_3$,
or a pharmaceutically acceptable salt thereof.

Embodiment 8

A compound according to Embodiment 7, wherein
$R^2$ is —CH$_3$ or —CH$_2$OH;
$R^3$ is H;
$R^4$ is —CH$_3$, —CH$_2$OH or —CH$_2$CH$_2$OH and $R^5$ is H or
$R^4$ is H and $R^5$ is CH$_3$ or —CH$_2$OH,
or a pharmaceutically acceptable salt thereof.

Embodiment 9

A compound according to Embodiment 8, wherein
$R^2$ is —CH$_3$ or —CH$_2$OH;
$R^3$ is H;
$R^4$ is —CH$_3$ or —CH$_2$CH$_2$OH and
$R^5$ is H,
or a pharmaceutically acceptable salt thereof.

Embodiment 10

A compound, or a pharmaceutically acceptable salt thereof, according to Embodiment 1 which is selected from
(S)-3-(2'-Amino-2-morpholin-4-yl-4'-trifluoromethyl-[4,5'] bipyrimidinyl-6-yl)-4-methyl-oxazolidin-2-one,
(S)-3-(2'-Amino-2-morpholin-4-yl-4'-trifluoromethyl-[4,5'] bipyrimidinyl-6-yl)-4-hydroxymethyl-5,5-dimethyl-oxazolidin-2-one,
racemic 3-(2'-amino-2-morpholino-4'-(trifluoromethyl)-4,5'-bipyrimidin-6-yl)-4-(hydroxymethyl)-4-methyloxazolidin-2-one,
(S)-3-(2'-amino-2-morpholino-4'-(trifluoromethyl)-4,5'-bipyrimidin-6-yl)-4-(hydroxymethyl)-4-methyloxazolidin-2-one (absolute stereochemistry not determined),
(R)-3-(2'-amino-2-morpholino-4'-(trifluoromethyl)-4,5'-bipyrimidin-6-yl)-4-(hydroxymethyl)-4-methyloxazolidin-2-one (absolute stereochemistry not determined),
(3aS,7aS)-3-(2'-Amino-2-morpholin-4-yl-4'-trifluoromethyl-[4,5']bipyrimidinyl-6-yl)-hexahydro-benzooxazol-2-one,
(S)-3-(2'-Amino-2-morpholin-4-yl-4'-trifluoromethyl-[4,5'] bipyrimidinyl-6-yl)-4-methoxymethyl-oxazolidin-2-one,
(4S,5S)-3-(2'-Amino-2-morpholin-4-yl-4'-trifluoromethyl-[4,5']bipyrimidinyl-6-yl)-4-hydroxymethyl-5-methyl-oxazolidin-2-one,
(S)-3-(2'-Amino-2-morpholin-4-yl-4'-trifluoromethyl-[4,5'] bipyrimidinyl-6-yl)-4-hydroxymethyl-oxazolidin-2-one,
(4S,5R)-3-(2'-Amino-2-(D8-morpholin-4-yl)-4'-trifluoromethyl-[4,5']bipyrimidinyl-6-yl)-4-hydroxymethyl-5-methyl-oxazolidin-2-one,
(S)-3-(2'-Amino-2-morpholin-4-yl-4'-trifluoromethyl-[4,5'] bipyrimidinyl-6-yl)-4-(2-hydroxy-ethyl)-oxazolidin-2-one,
(4S,5R)-3-[Z-Amino-2-((S)-3-methyl-morpholin-4-yl)-4'-trifluoromethyl-[4,5']bipyrimidinyl-6-yl]-4-hydroxymethyl-5-methyl-oxazolidin-2-one, Formic acid (4S,5R)-3-(2'-amino-2-morpholin-4-yl-4'-trifluoromethyl-[4,5']bipyrimidinyl-6-yl)-5-methyl-2-oxo-oxazolidin-4-ylmethyl ester,
(S)-3-[Z-Amino-2-((S)-3-methyl-morpholin-4-yl)-4'-trifluoromethyl-[4,5']bipyrimidinyl-6-yl]-4-methyl-oxazolidin-2-one,
(S)-3-(2'-Amino-2-morpholin-4-yl-4'-trifluoromethyl-[4,5']bipyrimidinyl-6-yl)-5-hydroxymethyl-oxazolidin-2-one,
(4S,5R)-3-(2'-Amino-2-morpholin-4-yl-4'-trifluoromethyl-[4,5']bipyrimidinyl-6-yl)-5-hydroxymethyl-4-methyl-oxazolidin-2-one,
(S)-3-(2'-Amino-2-morpholin-4-yl-4'-trifluoromethyl-[4,5']bipyrimidinyl-6-yl)-5-methyl-oxazolidin-2-one,
(S)-3-(2'-amino-2-D8-morpholino-4'-(trifluoromethyl)-[4,5-bipyrimidin]-6-yl)-4-methyloxazolidin-2-one,
(4S,5R)-3-(2'-Amino-2-morpholin-4-yl-4'-trifluoromethyl-[4,5']bipyrimidinyl-6-yl)-4-hydroxymethyl-5-methyl-oxazolidin-2-one,
(4S,5S)-3-(2'-Amino-2-morpholin-4-yl-4'-trifluoromethyl-[4,5']bipyrimidinyl-6-yl)-5-hydroxymethyl-4-methyl-oxazolidin-2-one,
(R)-3-(2'-Amino-2-morpholin-4-yl-4'-trifluoromethyl-[4,5']bipyrimidinyl-6-yl)-5-hydroxymethyl-oxazolidin-2-one,
(3aR,6aR)-3-(2'-amino-2-morpholino-4'-(trifluoromethyl)-[4,5'-bipyrimidin]-6-yl)-tetrahydrofuro[3,4-d]oxazol-2(3H)-one,
racemic (3aR*,6R*,6aR*)-3-(2'-Amino-2-morpholino-4'-(trifluoromethyl)-[4,5'-bipyrimidin]-6-yl)-6-hydroxy-hexahydro-2H-cyclopenta[d]oxazol-2-one,
(3aR,6R,6aR)-(Z-Amino-2-morpholino-4'-(trifluoromethyl)-[4,5'-bipyrimidin]-6-yl)-6-hydroxyhexahydro-2H-cyclopenta[d]oxazol-2-one,
(3aS,6S,6aS)-(Z-Amino-2-morpholino-4'-(trifluoromethyl)-[4,5'-bipyrimidin]-6-yl)-6-hydroxyhexa-hydro-2H-cyclopenta[d]oxazol-2-one, and
(4S,5R)-3-(2'-Amino-2-morpholino-4'-(trifluoromethyl)-[4,5'-bipyrimidin]-6-yl)-5-(2-hydroxyethyl)-4-methyloxazolidin-2-one.

Embodiment 11

A compound, or a pharmaceutically acceptable salt thereof, according to Embodiment 1 which is selected from (4S,5R)-3-[2'-Amino-2-((S)-3-methyl-morpholin-4-yl)-4'-trifluoromethyl-[4,5']bipyrimidinyl-6-yl]-4-hydroxymethyl-5-methyl-oxazolidin-2-one,
(4S,5R)-3-(2'-Amino-2-morpholin-4-yl-4'-trifluoromethyl-[4,5']bipyrimidinyl-6-yl)-4-hydroxymethyl-5-methyl-oxazolidin-2-one, and
(4S,5R)-3-(2'-Amino-2-morpholino-4'-(trifluoromethyl)-[4,5'-bipyrimidin]-6-yl)-5-(2-hydroxyethyl)-4-methyloxazolidin-2-one.

Embodiment 12

A compound which is selected from (4S,5R)-3-[Z-Amino-2-((S)-3-methyl-morpholin-4-yl)-4'-trifluoromethyl-[4,5']bipyrimidinyl-6-yl]-4-hydroxymethyl-5-methyl-oxazolidin-2-one,
(4S,5R)-3-(2'-Amino-2-morpholin-4-yl-4'-trifluoromethyl-[4,5']bipyrimidinyl-6-yl)-4-hydroxymethyl-5-methyl-oxazolidin-2-one, and
(4S,5R)-3-(2'-Amino-2-morpholino-4'-(trifluoromethyl)-[4,5'-bipyrimidin]-6-yl)-5-(2-hydroxyethyl)-4-methyloxazolidin-2-one.

Embodiment 13

The compound (4S,5R)-3-[2'-Amino-2-((S)-3-methyl-morpholin-4-yl)-4'-trifluoromethyl-[4,5']bipyrimidinyl-6-yl]-4-hydroxymethyl-5-methyl-oxazolidin-2-one.

Embodiment 14

The compound (4S,5R)-3-(2'-Amino-2-morpholin-4-yl-4'-trifluoromethyl-[4,5]bipyrimidinyl-6-yl)-4-hydroxymethyl-5-methyl-oxazolidin-2-one.

Embodiment 15

The compound (4S,5R)-3-(2'-Amino-2-morpholino-4'-(trifluoromethyl)-[4,5'-bipyrimidin]-6-yl)-5-(2-hydroxyethyl)-4-methyloxazolidin-2-one.

Embodiment 16

A pharmaceutically acceptable salt of the compound of Embodiment 13, Embodiment 14 or Embodiment 15.

Figure 2:
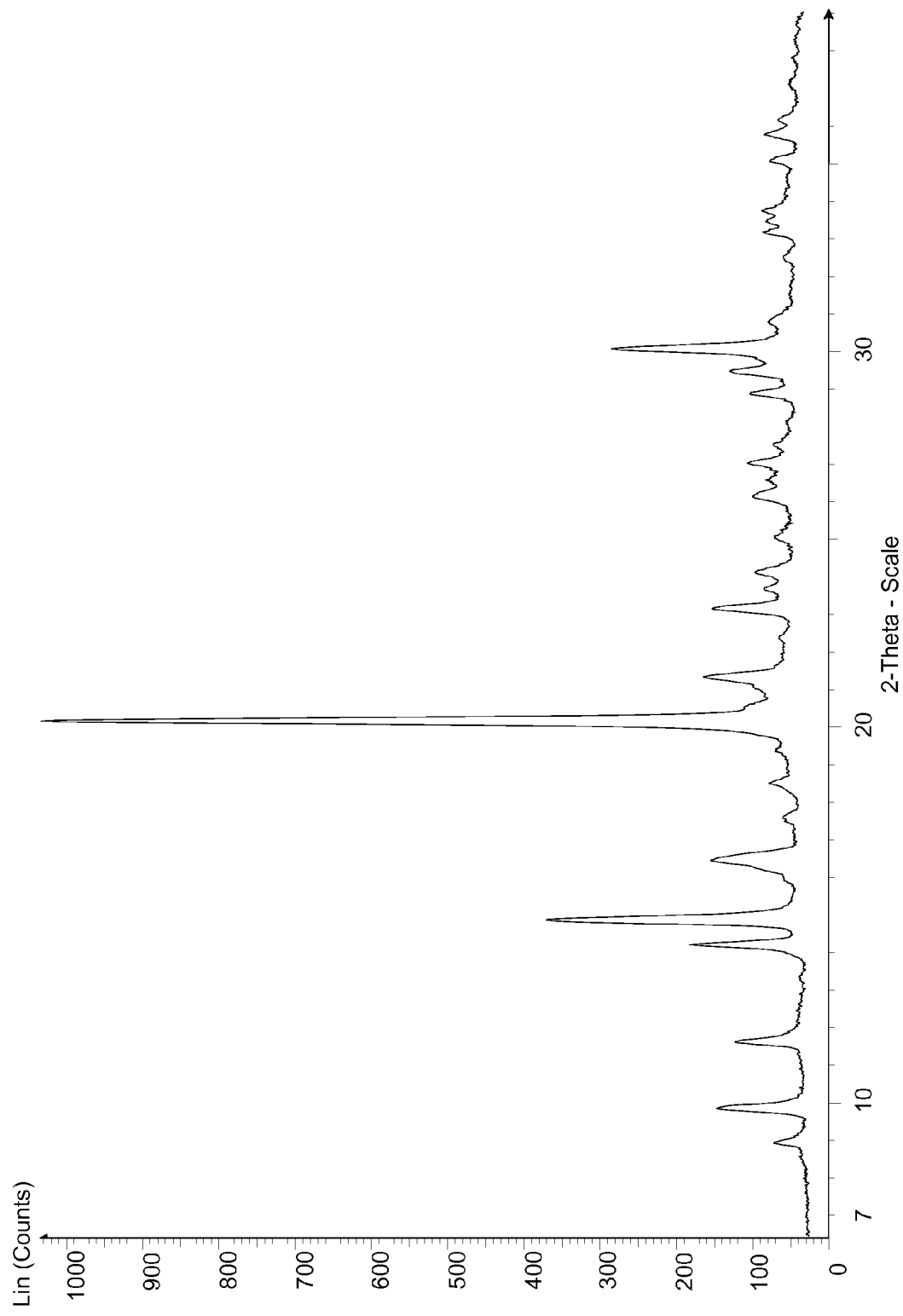
FIG. 2 is the powder X-Ray diffraction graph of the crystalline material of Example 10.
Figure 3:
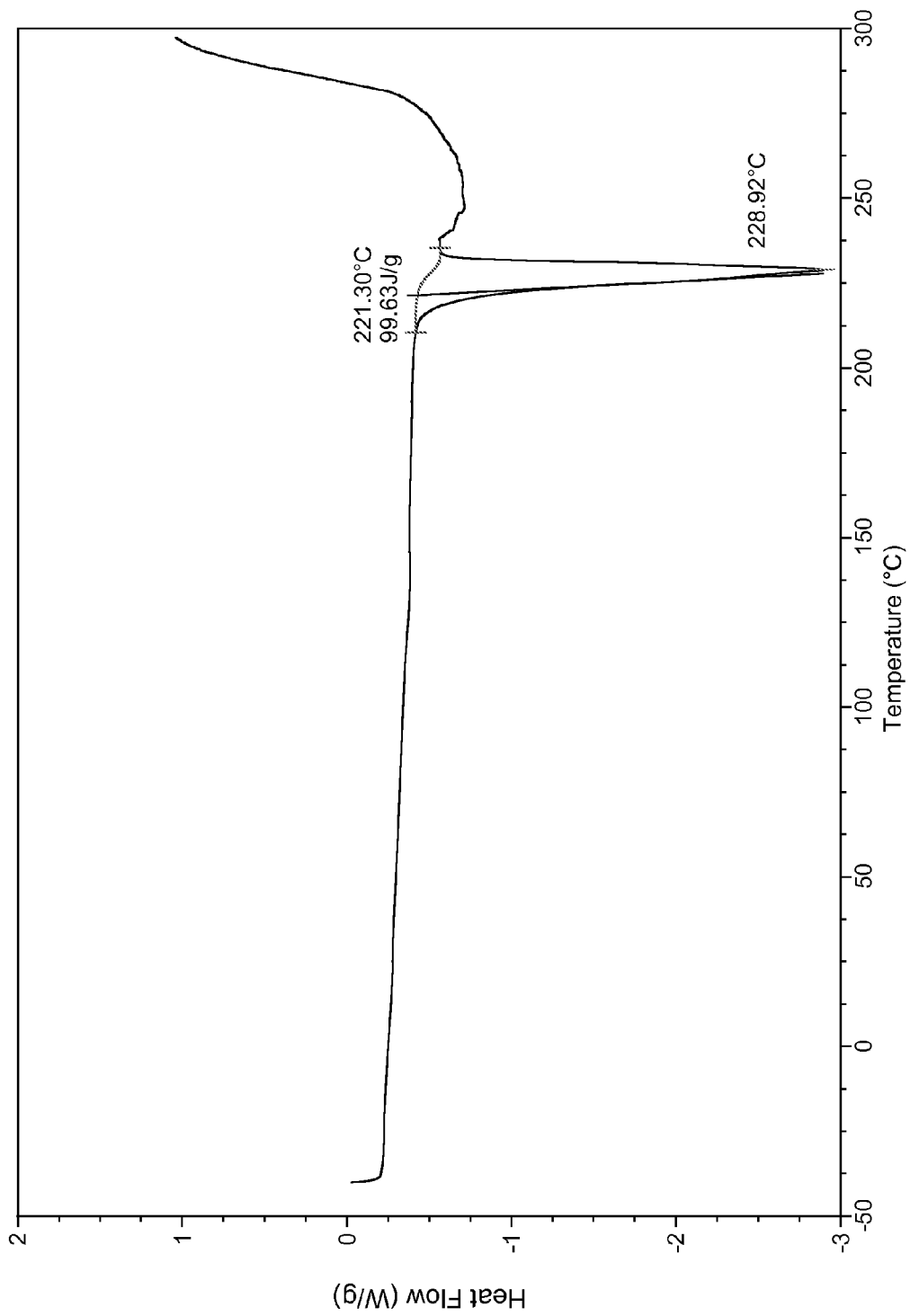
FIG. 3 is the differential Scanning calorimetry graph of the crystalline material of Example 18, batch A.

In yet another aspect of the present invention, a crystalline form of the compound obtained from Example 10 is provided having a X-ray diffraction spectrum substantially the same as the X-ray powder diffraction spectrum shown in FIG. 2.

Figure 4:
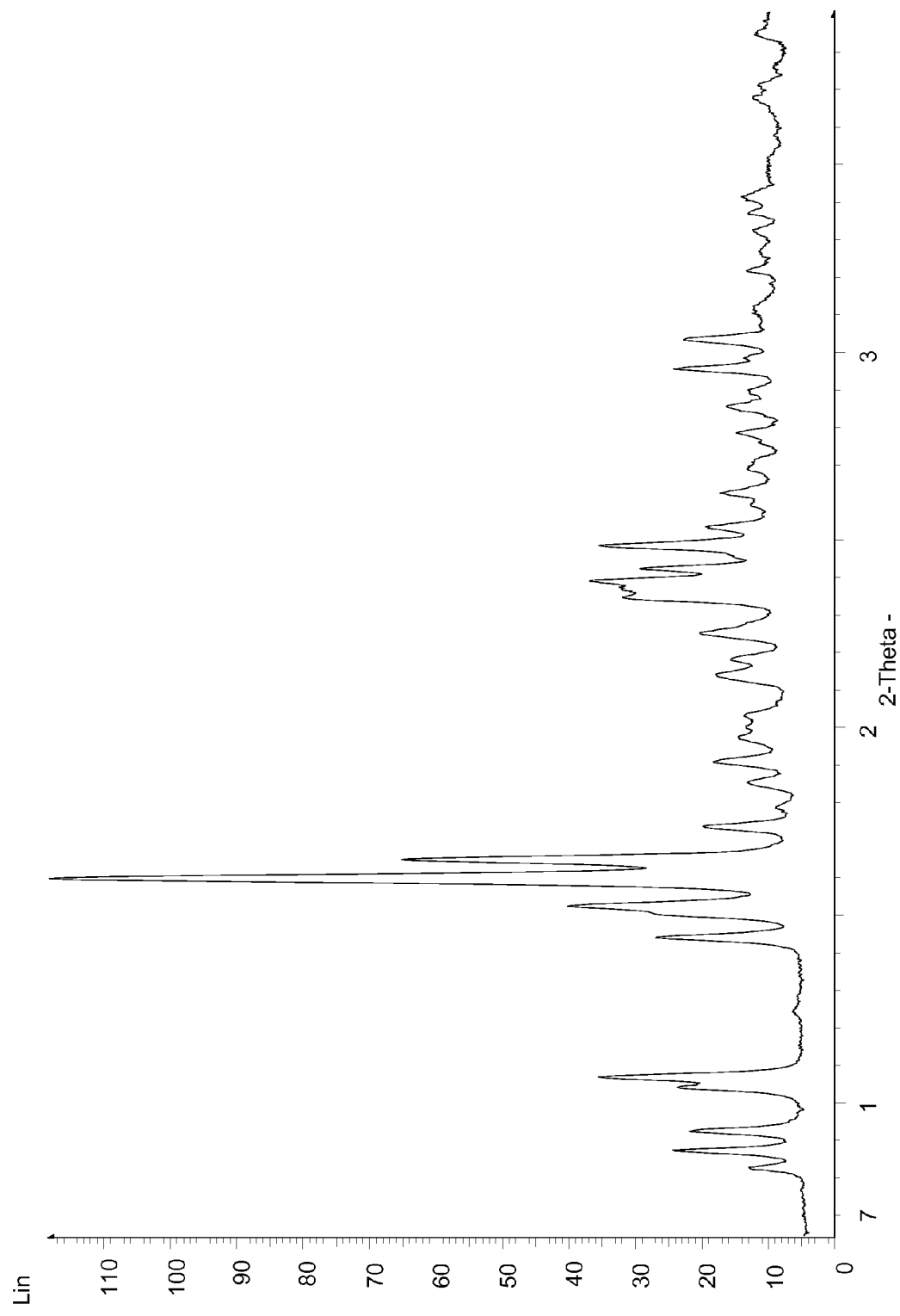
FIG. 4 is the powder X-Ray diffraction graph of the crystalline material of Example 18, batch A.
Figure 5:
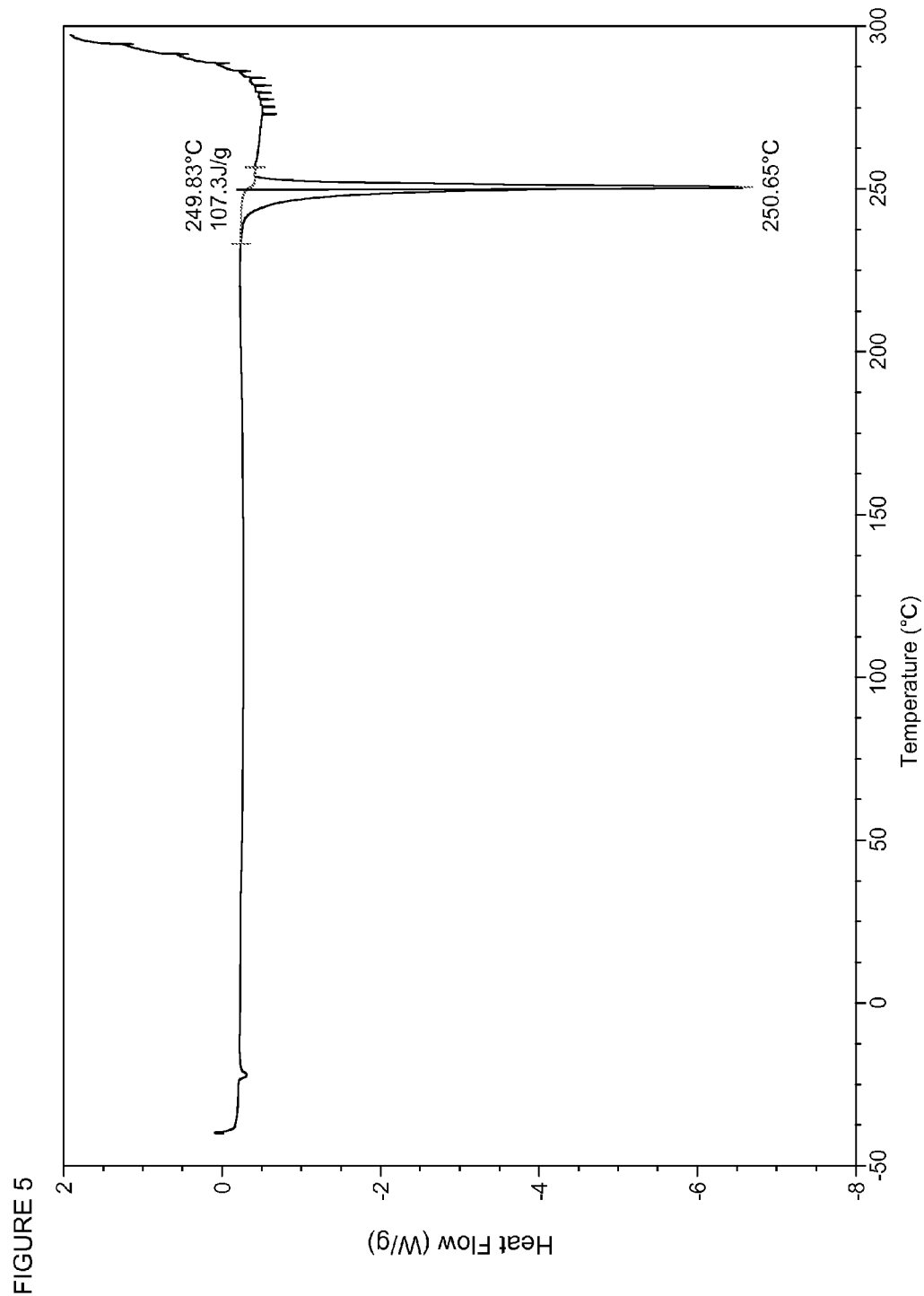
FIG. 5 is the differential Scanning calorimetry graph of the crystalline material of Example 18, batch B.

In yet another aspect of the present invention, a crystalline form of the compound obtained from Example 18, batch A is provided having a X-ray diffraction spectrum substantially the same as the X-ray powder diffraction spectrum shown in FIG. 4.

Figure 6:
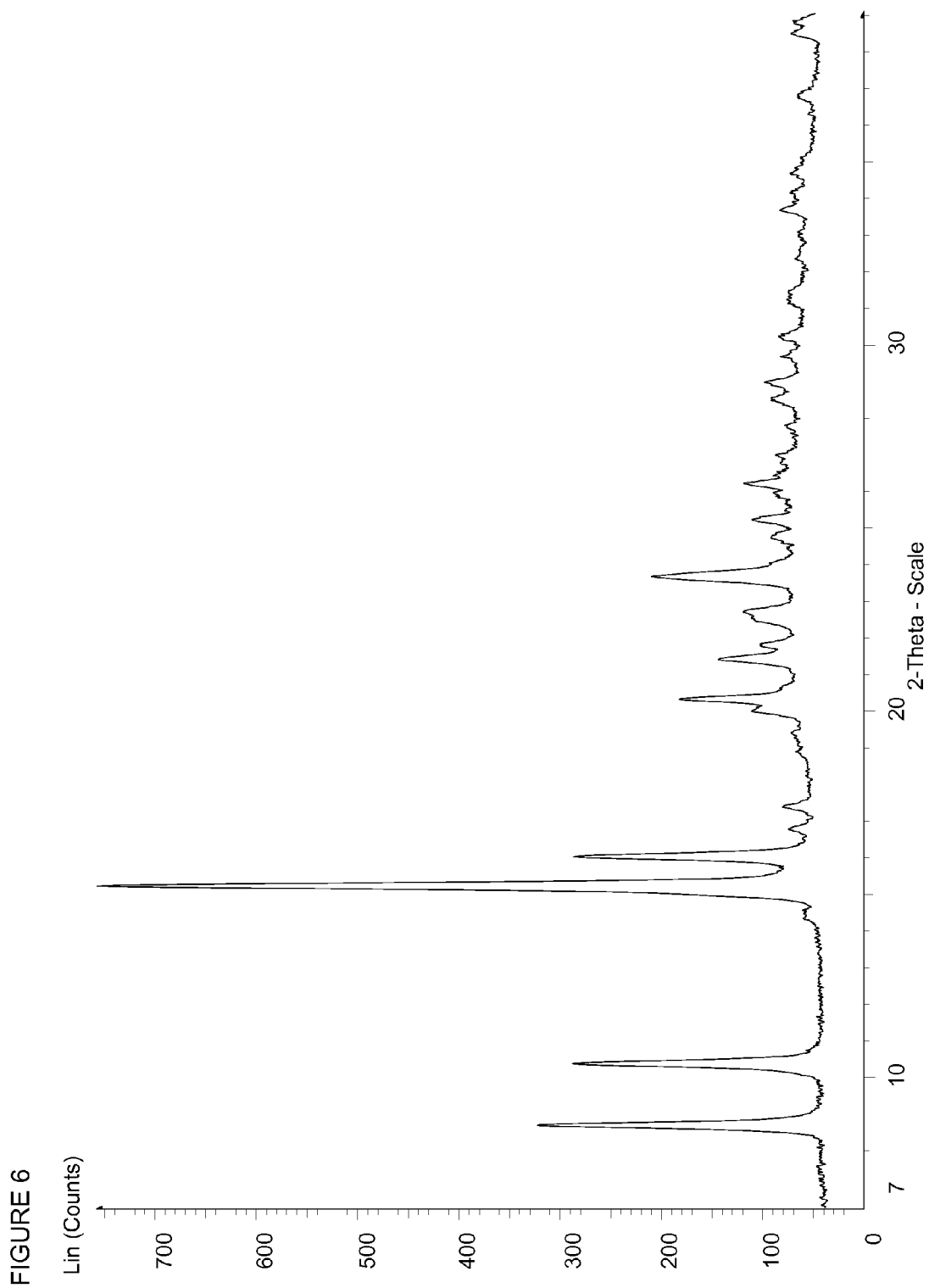
FIG. 6 is the powder X-Ray diffraction graph of the crystalline material of Example 18, batch B.
Figure 7:
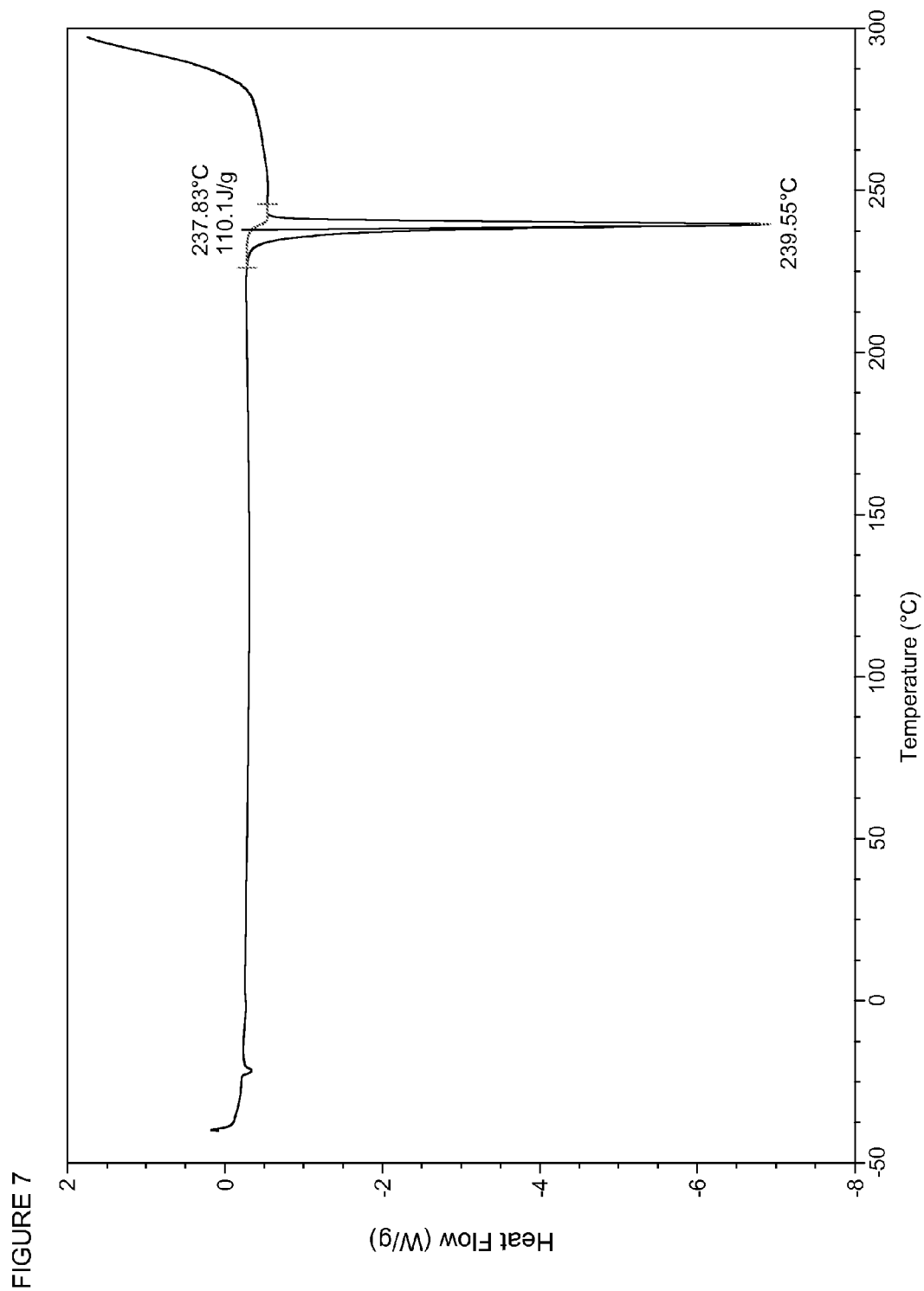
FIG. 7 is the differential Scanning calorimetry graph of the crystalline material of Example 18, batch C.

In yet another aspect of the present invention, a crystalline form of the compound obtained from Example 18, batch B is provided having a X-ray diffraction spectrum substantially the same as the X-ray powder diffraction spectrum shown in FIG. 6.

Figure 8:
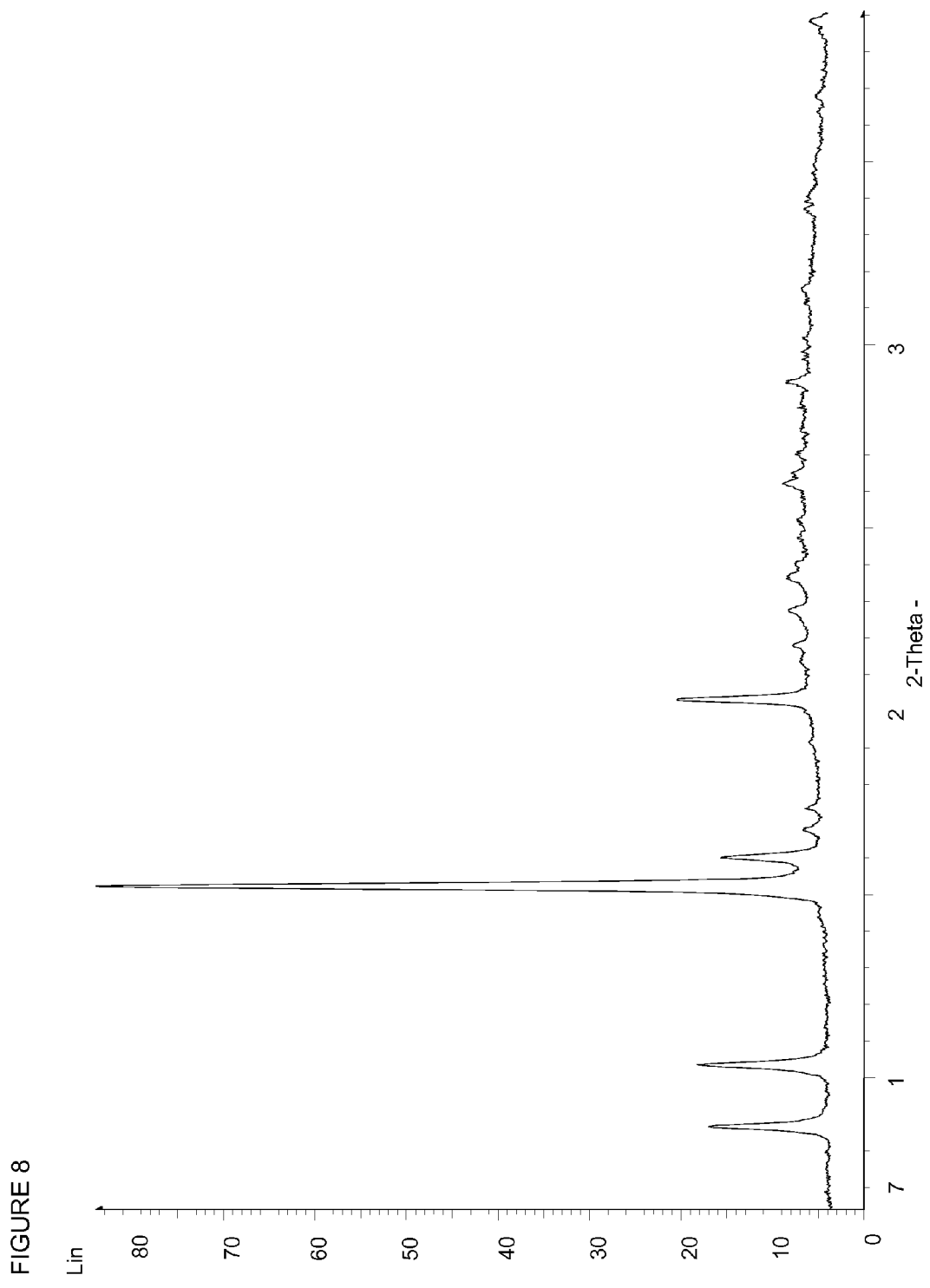
FIG. 8 is the powder X-Ray diffraction graph of the crystalline material of Example 18, batch C.
Figure 9:
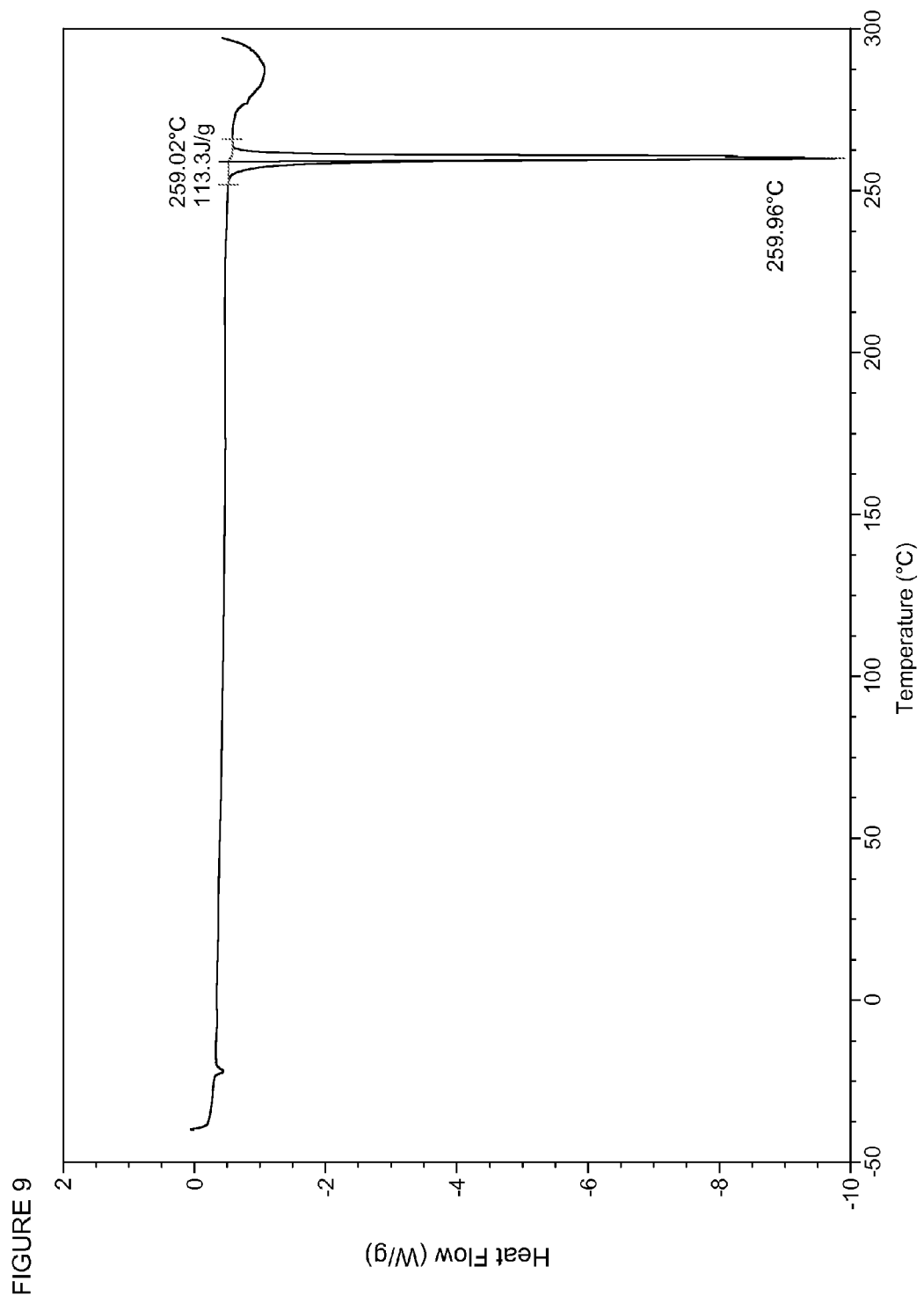
FIG. 9 is the differential Scanning calorimetry graph of the crystalline material of Example 18, batch D.

In yet another aspect of the present invention, a crystalline form of the compound obtained from Example 18, batch C is provided having a X-ray diffraction spectrum substantially the same as the X-ray powder diffraction spectrum shown in FIG. 8.

Figure 10:
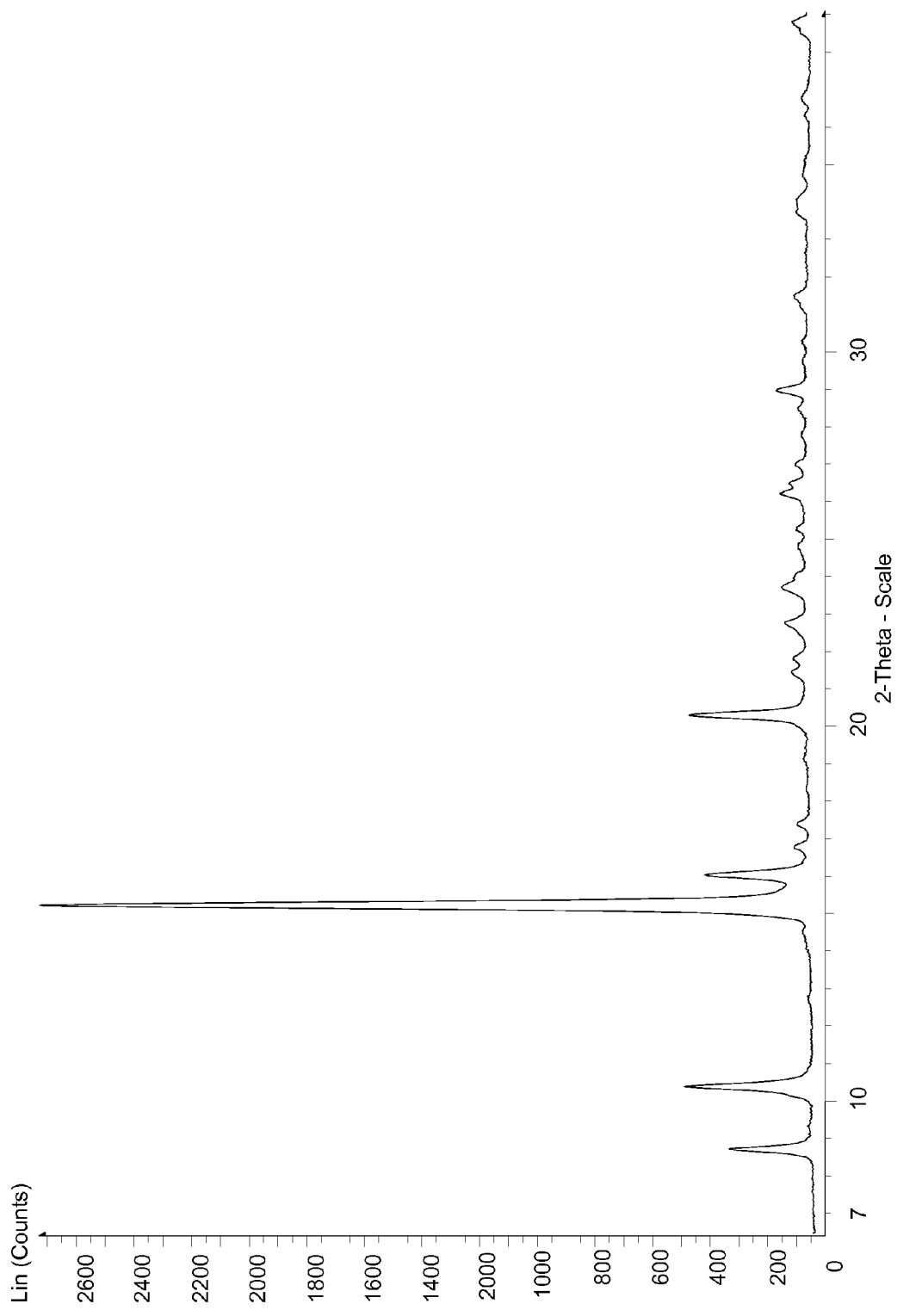
FIG. 10 is the powder X-Ray diffraction graph of the crystalline material of Example 18, batch D.
Figure 11:
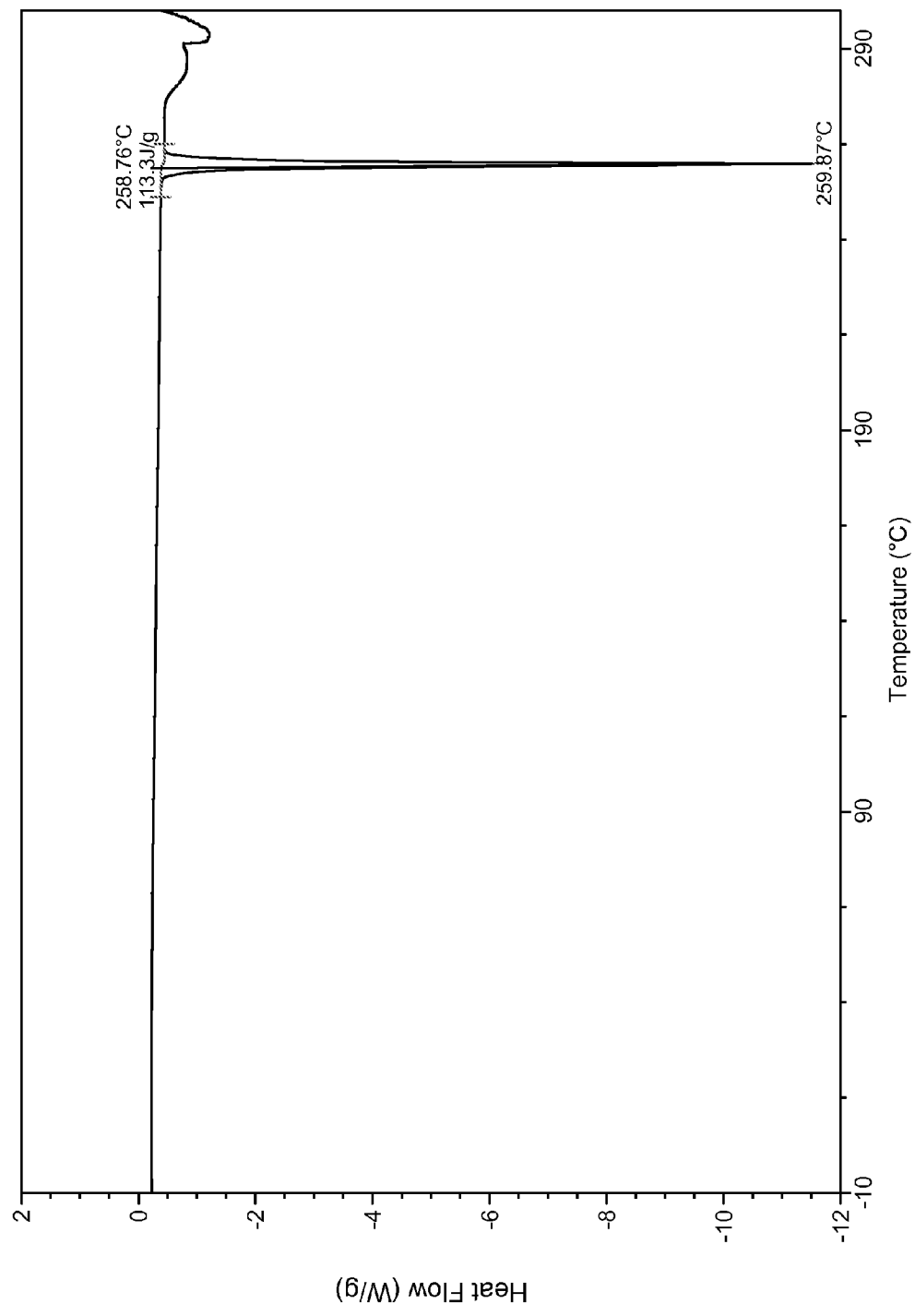
FIG. 11 is the differential Scanning calorimetry graph of the crystalline material of Example 18, batch E.

In yet another aspect of the present invention, a crystalline form of the compound obtained from Example 18, batch D is provided having a X-ray diffraction spectrum substantially the same as the X-ray powder diffraction spectrum shown in FIG. 10.

Figure 12:
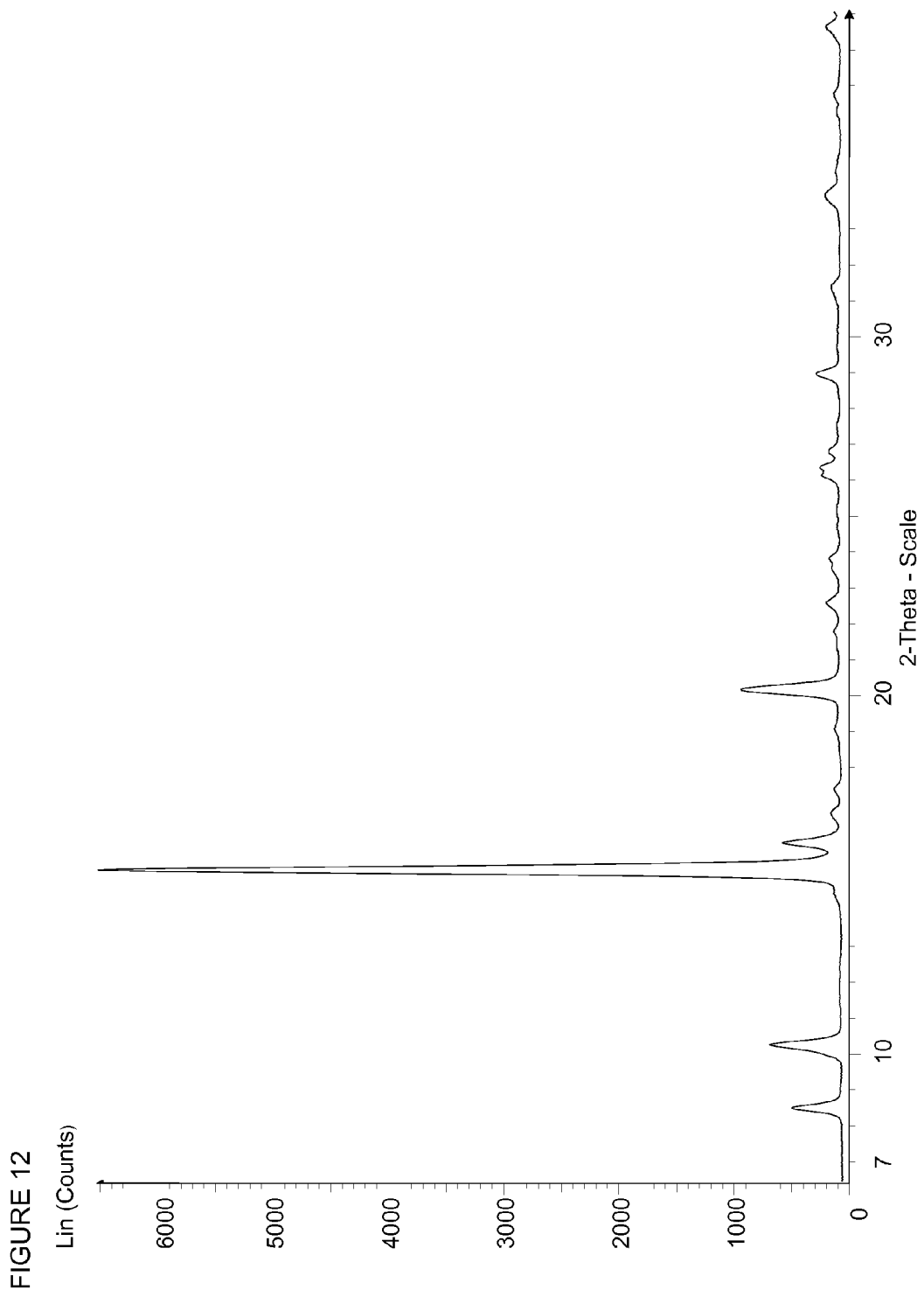
FIG. 12 is the powder X-Ray diffraction graph of the crystalline material of Example 18, batch E.

In yet another aspect of the present invention, a crystalline form of the compound obtained from Example 18, batch E is provided having a X-ray diffraction spectrum substantially the same as the X-ray powder diffraction spectrum shown in FIG. 12.

The term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

Specific embodiments are provided by the specific exemplified compounds described herein.

The present invention provides compounds and pharmaceutical formulations thereof that are useful in the treatment of diseases, conditions and/or disorders in which PI3K contributes to the disease pathogenesis described herein.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, volumes 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amino, hydroxyl or carboxyl groups) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Suitable hydroxyl protecting groups include trialkylsilyl ethers where one or two of the alkyl groups can be replaced by phenyl. Suitable carboxyl protecting groups (C(O)O-Pg) include alkyl esters (e.g., methyl, ethyl or t-butyl), benzyl esters, silyl esters, and the like. The need for such protection is readily determined by one skilled in the art. For a general description of protecting groups and their use, see T. W. Greene, Protective Groups in Organic Synthesis, John Wiley & Sons, New York, 1991.

Scheme 1 (below) describes a potential route for producing compounds of Formula (IA'), where $R^1$-$R^5$ are as defined above. In cases where a protecting group is present a deprotection step is added to convert protected IA' into IA'.

Scheme 1

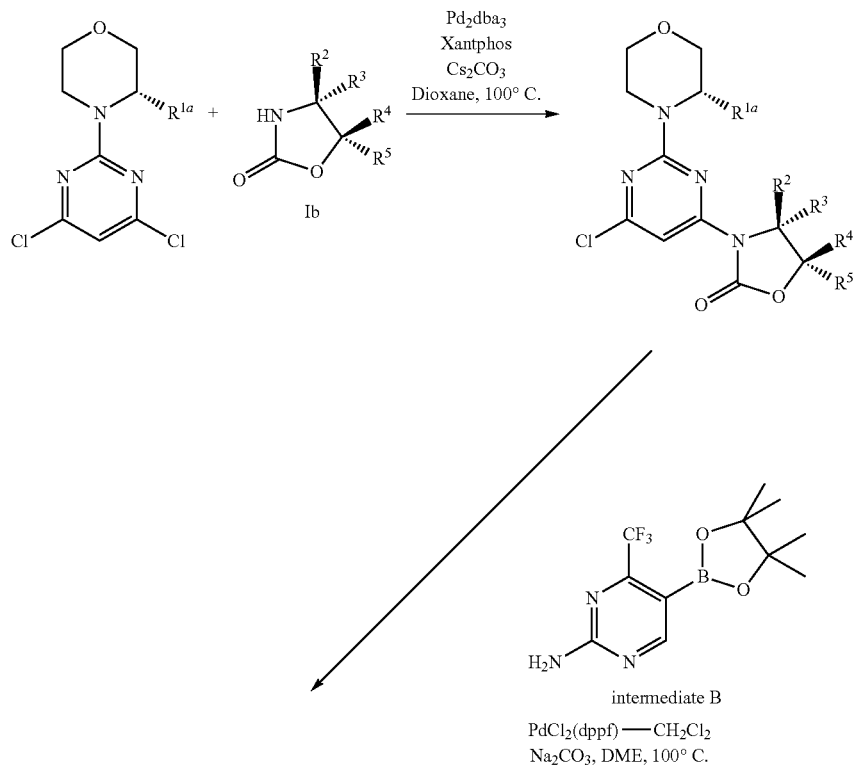

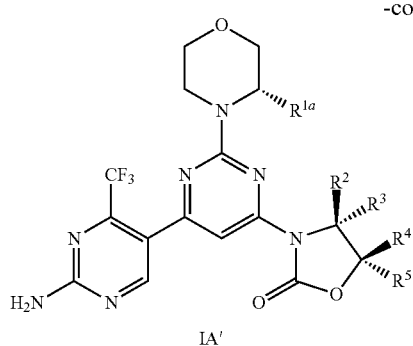

IA'

Alternatively, compounds of Formula (IA') can also be synthesized by inverting the steps shown in scheme I, i.e. Suzuki coupling first, followed by the Buchwald reaction with Ib.

For those oxazolidine-2-ones Ib that are not commercially available, Scheme 2 below provides a process for preparing those said intermediates where $R^2$-$R^5$ are as defined above. If a primary hydroxyl group is present in either $R^2$ to $R^5$, a selective protection step is preceding as exemplified in Scheme 3. The amine group can be protected in a further preceding step as shown in Scheme 4, where also a different hydroxyl protecting group is shown.

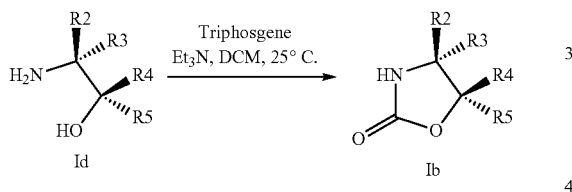

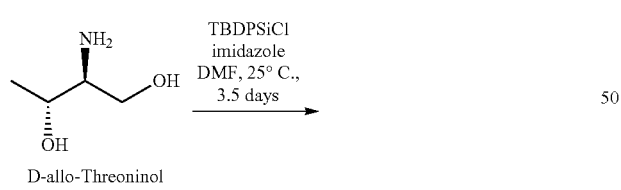

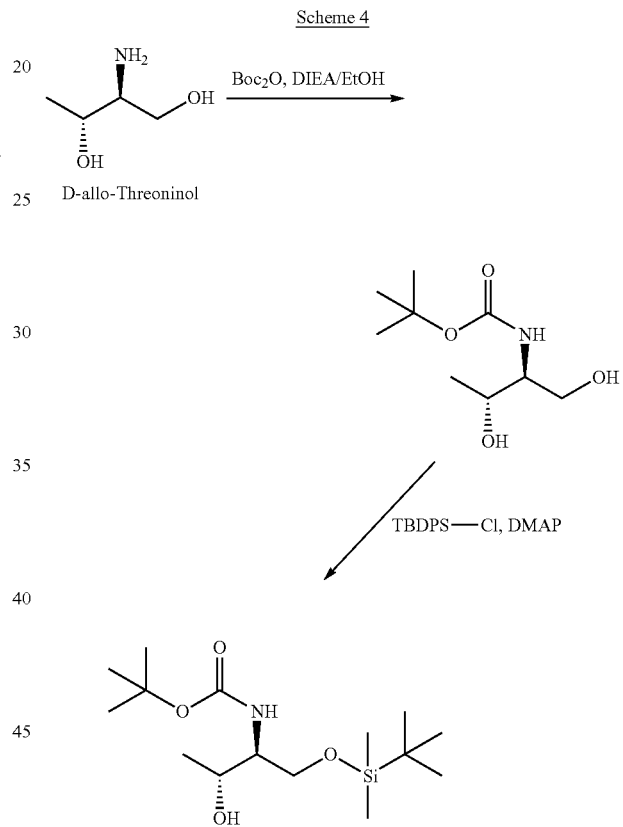

The protected product of Scheme 3 and be cyclised with triphosgene as generally shown in Scheme 2, and specifically shown in Scheme 5, to provide an example of a Ib intermediate.

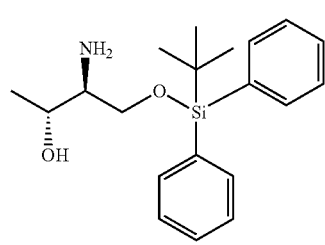

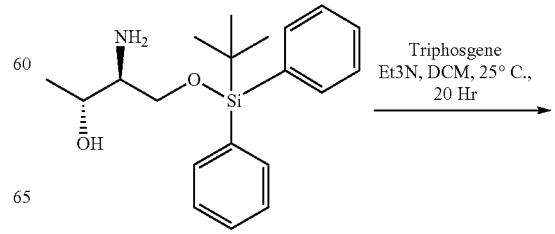

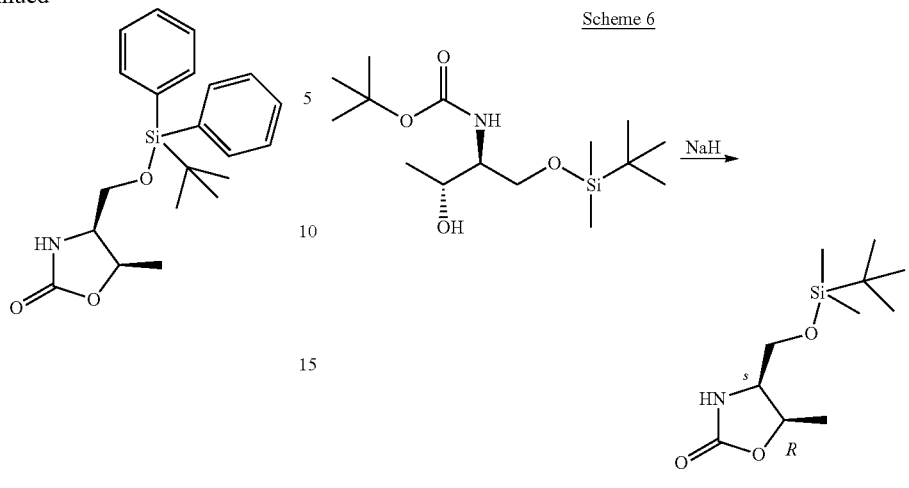
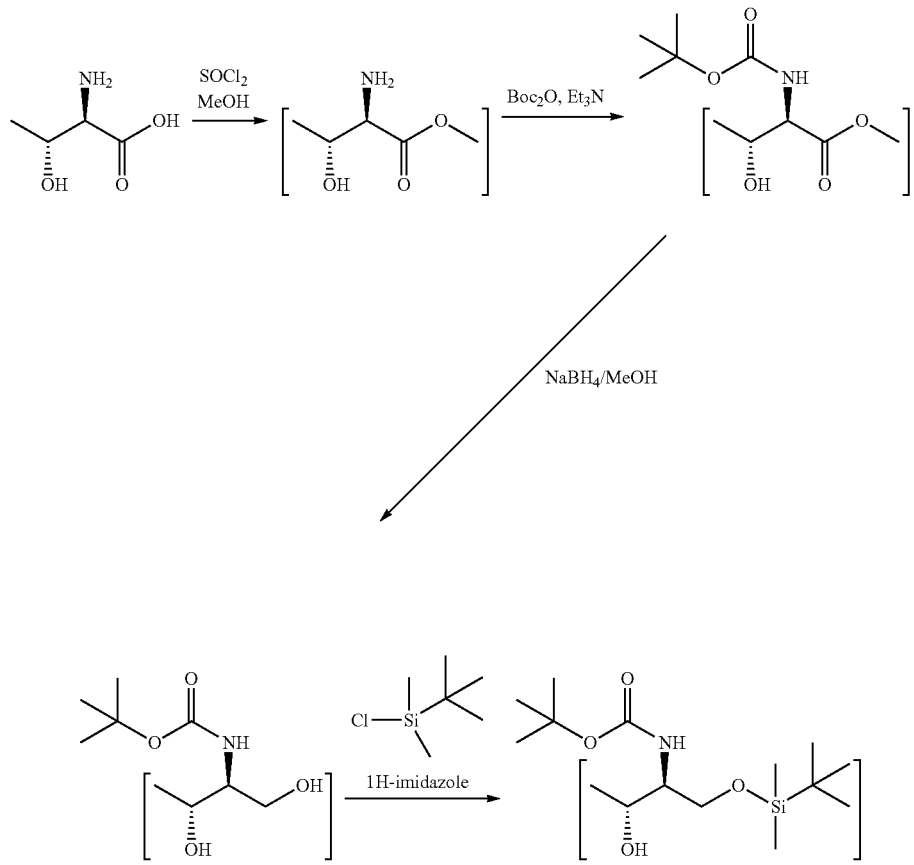
The doubly-protected product of Scheme 4 and be cyclised with sodium hydride as shown in Scheme 6 to provide an example of a Ib intermediate.
Scheme 7 depicts an alternative route to the doubly-protected intermediate of Scheme 4, which can then be cyclised as already shown in Scheme 6.

Scheme 8 below provides the synthesis of the boronic ester intermediate B.

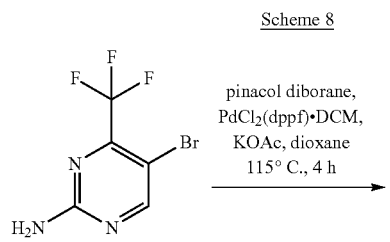

Scheme 8 pinacol diborane,
PdCl₂(dppf)•DCM,
KOAc, dioxane
115° C., 4 h

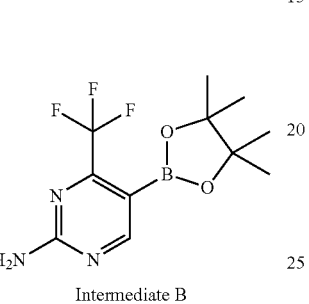

Intermediate B

Reaction of the cyclised product of Scheme 6 with the 4,6-dichloro-pyrimidine intermediate (e.g. intermediate A or the product from step 10.1, both referred to herein below) as shown in Scheme 1, can provide further intermediates, and specific ones are shown as follows:

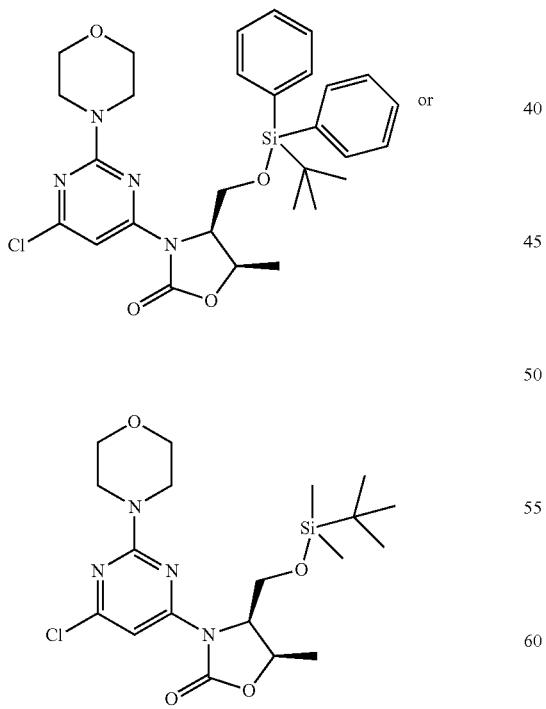

Further reaction of the formed intermediates as shown in Scheme 1 with intermediate B, provides a protected product IA', as follows:

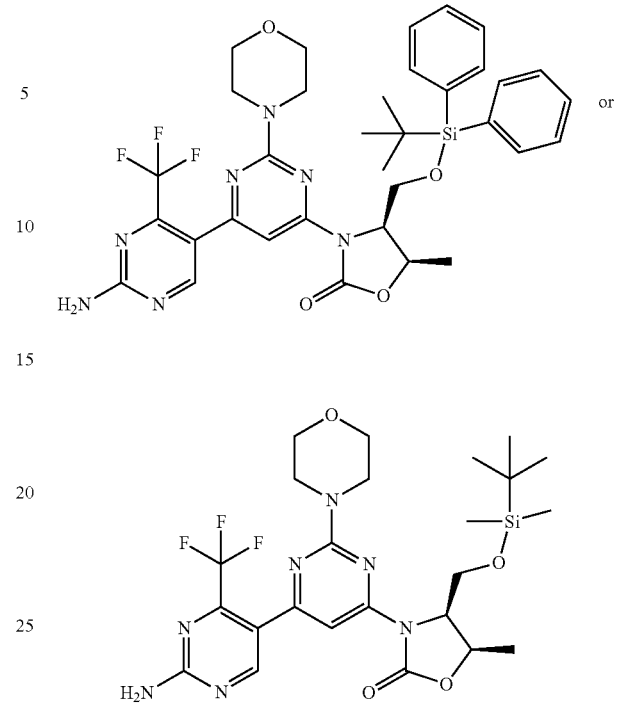

Thus, an intermediate compound of the invention includes a compound of the following Formulae:

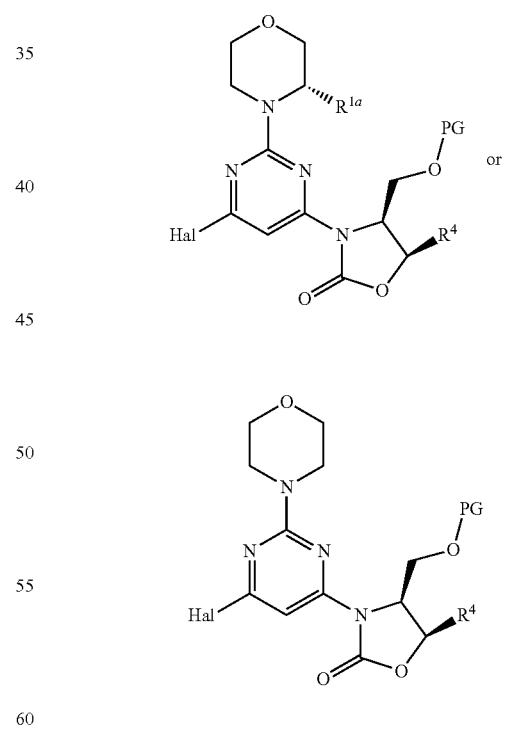

Wherein $R^{1a}$ and $R^4$ are as previously defined herein, Hal is halogen, such as choro, and PG is a protecting group, for example a silyl protecting group forming for example tri-alkylsilyl ethers where one or two of the alkyl groups can be replaced by phenyl, for example an alkyl-diphenyl-silyl ether protecting group, specifically dimethyl-tertbutyl-silyl, or diphenyl-tertbutyl silyl.

Another intermediate compound of the invention includes a compound of the following Formulae:

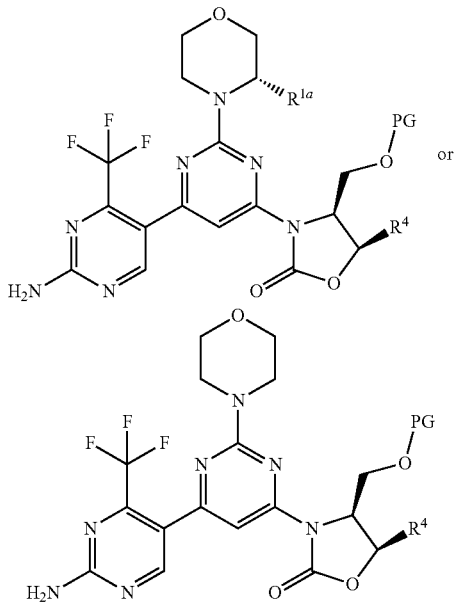

Other similarly protected intermediate compounds as depicted herein above can be envisaged with reference to the formulae herein if a primary hydroxyl group is present in either $R^2$ to $R^5$. Such protected compounds are also included in the disclosure. For example where $R^4$ is the group $CH_2CH_2OH$, this can be protected to provide compounds wherein $R^4$ is $CH_2CH_2O$-PG, wherein PG is as defined above, for example:

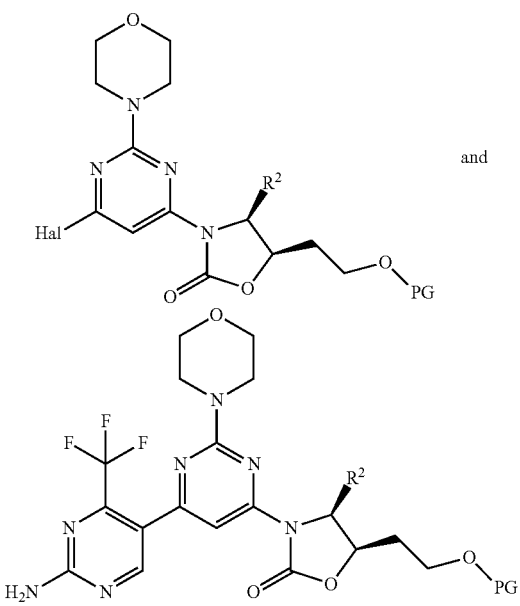

Deprotection of the tertiarybutyldiphenylsilyl or tertiarybutyldimethylsilyl protected hydroxyl group (general deprotection of silyl ethers) of protected product IA', to provide, for example, the final product, can be achieved using HF.pyridine (e.g. in THF) or HCl.

The compounds of the present invention, or intermediates used herein, may be isolated and used as the compound per se (for example free base form) or as its salt if for example the pKA value of the compound is such to allow salt formation. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and which typically are not biologically or otherwise undesirable. The compounds of the present invention may be capable of forming acid addition salts by virtue of the presence of an amino group. Compounds per se of the invention are preferred.

Inorganic acids and organic acids for formation of pharmaceutically acceptable acid addition salts include, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids for salt derivation include, for example, hydrochloric acid, hydrobromic acid, sulfuric acid, nitric acid, phosphoric acid, and the like.

Organic acids for salt derivation include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts may be formed with inorganic and organic bases.

Inorganic bases for salt derivation include, for example, ammonium salts and metals from columns I to XII of the periodic table. In certain embodiments, the salts may be derived from sodium, potassium, ammonium, calcium, magnesium, iron, silver, zinc, and copper; particularly suitable salts include ammonium, potassium, sodium, calcium and magnesium salts.

Organic bases for salt derivation include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In cases where pharmaceutically acceptable salts of the present invention can be formed, they can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Unless indicated otherwise, any formula given herein is intended to represent unlabeled forms. Isotopically labeled forms of the compounds with deuterium are shown with deuterium (D) as a substituent in place of H. Other isotopically labeled compounds of the present invention may be prepared and have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I, respectively. The invention can include various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention can generally be prepared by carrying out the procedures disclosed in the schemes or in the examples and preparations described below by substituting a readily available isotopically labeled reagent for a non-isotopically labeled reagent, for example deuterium labeled morpholine (D8-morpholine).

Furthermore, substitution with heavier isotopes, particularly deuterium (i.e., $^2$H or D) may afford certain therapeutic advantages resulting from greater metabolic stability, for example increased in vivo half-life, reduced dosage requirements, reduced CYP inhibition (competitive or time dependent) or an improvement in therapeutic index. For example, substitution with deuterium may modulate undesirable side effects of the undeuterated compound, such as competitive CYP inhibition, time dependent CYP inactivation, etc. It is understood that deuterium in this context is regarded as a substituent in compounds of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Furthermore, the compounds of the present invention, including their salts, may also be obtained in the form of their hydrates, or include other solvents used for their crystallization. The compounds of the present invention may inherently or by design form solvates with pharmaceutically acceptable solvents (including water). Such solvent molecules are those commonly used in the pharmaceutical art, which are known to be innocuous to the recipient, e.g., water, ethanol, and the like. The term "hydrate" refers to the complex where the solvent molecule is water. The term "solvate" refers to a molecular complex of a compound of the present invention (including pharmaceutically acceptable salts thereof) with one or more solvent molecules incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or compound according to the present invention, within the crystalline lattice structure.

The compounds of the present invention, including salts, hydrates and solvates thereof, may inherently or by design form polymorphs.

As used herein "polymorph" refers to crystalline forms having the same chemical composition but different spatial arrangements of the molecules, atoms, and/or ions forming the crystal.

As used herein "amorphous" refers to a solid form of a molecule, atom, and/or ions that is not crystalline. An amorphous solid does not display a definitive X-ray diffraction pattern.

Pharmaceutically acceptable solvates in accordance with the invention include those wherein the solvent of crystallization may be isotopically substituted, e.g. $D_2O$, $d_6$-acetone, $d_6$-DMSO.

It will be recognized by those skilled in the art that the compounds of the present invention contain chiral centers and as such exist in isomeric forms. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention. It is understood that a substituent may be attached at a chiral center of a carbon atom. Therefore, compounds of the invention include enantiomers, shown by indicating stereospecific arrangements at chiral centers in the structural depiction of the compounds of the invention, wherein a broken wedge bond indicates the attached substituent or atom is below the plane and a solid wedge bond indicates the attached substituent or atom is above the plane.

"Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Any asymmetric atom (e.g., chiral carbon or the like) of the compound(s) of the present invention can be enantiomerically enriched, for example the (R)- or (S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration described for the specific asymmetric atom (e.g. chiral carbon).

Accordingly, a compound of the present invention can be in the form of a substantially pure enantiomer.

Any resulting mixtures of isomers can be separated on the basis of the physicochemical differences of the constituents, into the pure or substantially pure optical isomers, for example, by chromatography and/or fractional crystallization.

Optically active (R)- and (S)-isomers may be prepared using chiral synthons or chiral reagents, or resolved using conventional techniques. Any resulting racemates of final products or intermediates can be resolved into the optical antipodes by known methods. For example, known methods include separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

The compounds of formula (I) inhibit PI3 kinases (PI3K) and may therefore be useful in the treatment of protein or lipid kinase dependant diseases, especially diseases depending on the class I PI3kinases, PI3Kalpha, PI3Kbeta, PI3Kdelta and PI3Kgamma or one or more of the individual kinase members thereof or any combination of any two or more of the mentioned kinases.

Compounds that inhibit the activity of more than one of the Class I PI3K isoforms (alpha, beta, delta and gamma), in particular substantially equipotent on the ClassIA members p110a, p110b and p110d and optionally as well as the classIB member p110g, are considered to be of benefit because such compounds are considered to have the ability to avoid adaption mechanisms due to pathway rewiring through the other isoforms, compared to compounds with unique specificity, e.g. specificity for one member of the PI3K Class I family. By "equipotent", it is meant that the compounds inhibit several isoforms to a comparable extent, e.g. as measured in an enzyme or cellular assay described herein.

Increased inhibition potency of at least one of the PI3K isoforms (i.e. inhibit at least one PI3K isoform at lower concentrations) may also be advantageous. In the case of PTEN null tumors, for example, although the driving isoform is p110b, complete efficacy could require participation of the other Class IA isoforms. For example potency on the alpha and beta isoforms could be advantageous.

There is also a need for compounds which potently inhibit PI3Kalpha kinase, for example, for the treatment of cancers that are primarily driven by oncogenic forms of the gene encoding p110a (e.g. PIK3CA H1047R or E545K), as well as tumors showing increased copy number of PIK3CA.

It is desirable that the compounds of the present invention display the mentioned PI3 kinase activity without displaying activity on mTOR, or at least display a favourable selectivity for inhibiting one or more of the Class I PI3 Kinases over mTOR. For example, compounds which show selective inhibition in favour of one or more PI3K isoforms (for example at least two, preferably three, e.g. the alpha, beta and delta isoforms) compared to mTOR are desirable, because the mTOR inhibitory effect generally reduces the safety window, more especially when the compound inhibits mTOR more strongly than PI3K (unfavorable ratio).

Furthermore, PI3K inhibitors which have a reduced off-target effect, or do not possess an off-target effect, such as not possessing tubulin binding, are desired, as such effect can cause toxicity effects not connected with the on-target PI3K inhibition and therefore such compounds may require additional careful dosing control to ensure the therapeutic effect is controllable and attributable to PI3K inhibition. The compounds of the present invention, when measured using the procedures described herein, show weak or no observable off-target effect (tubulin binding).

Compounds that inhibit the activity of more than one of the Class I PI3K isoforms (alpha, beta, delta and gamma), in particular substantially equipotent on the ClassIA members p110a, p110b and p110d and optionally as well as the classIB member p110g, and in addition have a reduced off-target effect, or do not possess an off-target effect, such as not possessing tubulin binding, or reduced tubulin binding, are desired.

Desirably compounds displaying an improved inhibition of at least one (e.g. PI3Kalpha), but especially two (e.g. PI3Kalpha and PI3Kbeta) or three (e.g. PI3Kalpha, PI3Kbeta and PI3Kdelta), or all four class 1 PI3Ks (PI3Kalpha, PI3Kbeta, PI3Kdelta and PI3Kgamma) as well as a reduced (in particular, an absence of) off-target effect (e.g. reduced or absence of tubulin binding) are sought. Desirably, these compounds also show selective inhibition in favour of one or more PI3K isoforms (for example at least two, preferably three, e.g. the alpha, beta and delta isoforms) compared to mTOR are desirable.

Consequently, in a further aspect a compound of the present invention may be used (e.g. in the manufacture of a medicament) for the treatment of diseases, conditions or disorders associated with the inhibition or antagonism of the PI3 kinases in a subject (e.g. mammal, preferably a human). Because of the relevance to PI3 kinase inhibition, compounds of the present invention are therefore considered useful in the treatment of proliferative diseases such as cancer. Particular diseases/conditions for treatment by the compounds of the present invention include a benign or especially malignant tumor, solid tumors, a carcinoma of the brain, kidney, liver, adrenal gland, bladder, breast, stomach (especially gastric tumors), oesophagus, ovaries, colon, rectum, prostate, pancreas, lung (e.g. non-small cell lung cancer, small cell lung cancer), vagina, thyroid, sarcoma, glioblastomas, multiple myeloma or gastrointestinal cancer, especially colon carcinoma or colorectal adenoma, or a tumor of the neck and head, other diseases such as Cowden syndrome, Lhermitte-Duclos disease and Bannayan-Zonana syndrome, (or diseases in which the PI3K/PKB pathway is aberrantly activated), prostate hyperplasia, a neoplasia, especially of epithelial character, preferably mammary carcinoma or squamous cell carcinoma, B-cell malignancies such as chronic lymphocytic leukemia (CLL), non-Hodgkin's lymphoma (NHL), plasma cell myeloma and Hodgkin's lymphoma (NH) or a leukemia. The compounds desirably are able to bring about the regression of tumors and to prevent the formation of tumor metastases and the growth of (also micro) metastases. It may also be possible to use the compounds of formula (I) in the treatment of diseases of the immune system insofar as several or, especially, individual lipid kinases and/or (further) serine/threonine protein kinases are involved.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the present invention are typically used as a pharmaceutical composition (e.g., a compound of the present invention and at least one pharmaceutically acceptable carrier).

Thus, in another aspect, the present invention provides a pharmaceutical composition comprising a compound of the present invention, or a pharmaceutically acceptable salt thereof, and a pharmaceutically acceptable carrier.

A compound of the present invention may be provided in a composition in amorphous form. A compound of the present invention may be provided in a composition in its free form, i.e. not in the form of a salt (the free base form). A compound of the present invention may be provided in a composition in its free form, i.e. not in the form of a salt (the free base form) and which is also in amorphous form.

As used herein, the term "pharmaceutically acceptable carrier" includes generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Solutions of the active ingredient, and also suspensions, and especially isotonic aqueous solutions or suspensions, may be used, it being possible, e.g., in the case of lyophilized compositions that comprise the active ingredient alone or together with a carrier, e.g., mannitol, for such solutions or suspensions to be produced prior to use. The pharmaceutical compositions may be sterilized and/or may comprise adjuvants, e.g., preservatives, stabilizers, wetting and/or emulsifying agents, solubilizers, salts for regulating the osmotic pressure and/or buffers; and are prepared in a manner known per se, e.g., by means of conventional dissolving or lyophilizing processes. The said solutions or suspensions may comprise viscosity-increasing substances, such as sodium carboxymethylcellulose, carboxymethylcellulose, Hydroxypropylmethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8-22 carbon atoms, especially from 12-22 carbon atoms, e.g., lauric acid, tridecylic acid, myristic acid, pentadecylic acid, palmitic acid, margaric acid, stearic acid, arachidic acid, behenic acid or corresponding unsaturated acids, e.g., oleic acid, elaidic acid, erucic acid, brasidic acid or linoleic acid, if desired with the addition of antioxidants, e.g., vitamin E, beta-carotene or 3,5-di-tert-butyl-4-hydroxytoluene. The alcohol component of those fatty acid esters has a maximum of 6 carbon atoms and is a mono- or poly-hydroxy, e.g., a mono-, di- or tri-hydroxy; alcohol, e.g., methanol, ethanol, propanol, butanol or pentanol; or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$-$C_{12}$, Hüls AG, Germany), but especially vegetable oils, such as cottonseed oil, almond oil, olive oil, castor oil, sesame oil, soybean oil and more especially groundnut oil.

Injectable compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Pharmaceutical compositions for topical administration can be obtained by combining the active ingredient with a liquid carrier (e.g. an aqueous liquid carrier) to dissolve or disperse the active, together with further optional formulating ingredients such as solvents/solubilisers, gelling agents, oils, stabilisers, buffers and preservatives to provide for example a solution, lotion, cream, gel or ointment. The pharmaceutical compositions for topical administration may be provided, for example, for dermal application. The pharmaceutical compositions for topical administration may comprise from approximately 0.1% to approximately 2% of active ingredient, the active ingredient being especially a compound of formula (I), in particular, a compound described in the individual examples herein.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition comprising a therapeutically effective amount of a compound of the present invention may be formulated for use as a parenteral administration. The pharmaceutical compositions (e.g., intravenous (iv) formulation) can be subjected to conventional pharmaceutical operations such as sterilization and/or can contain conventional inert diluents, or buffering agents, as well as adjuvants, such as preservatives, stabilizers, wetting agents, emulsifiers and buffers well known to those of skill in the art.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (a g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

A compound of the present invention, in particular, a compound described in the individual examples herein, may be provided in an amorphous form.

A compound of the present invention, in particular, a compound described in the individual examples herein may be formulated as a standard suspension, nanosuspension and solid dispersion, e.g. as follows.

Standard Suspension:
1.) Required amount of crystalline material of Example 18, Batch E was weighed with the aim of targetting a formulation concentration of 3 mg/ml.
2.) The crystalline material of Example 18, Batch E was then dispersed in 0.5% [w/w] Carboxymethylcellulose/0.5% [w/w] Tween80/Water
3.) Suspension was vortexed to homogenize
4.) Suspension was sonicated using a probe sonicator to reduce particle size (2 min)

Nanosuspension:
1.) 32 mg of crystalline material of Example 18, Batch E precisely weighed into a tailor-made marble milling device
2.) 2.148 g of 0.2 mm Zirconia milling medium was added to the milling device 3.) 0.608 ml of 1% [w/V] HPMC 603 (Hydroxypropylmethylcellulose grade 603)/0.05% [/w] SDS (SodiumDodecylSulfate)/Water was added to the milling device
4.) The milling devices were closed and put into a rotary mill
5.) The sample was milled for 4 h at 400 rpm
6.) Nanosuspension were collected using a syringe Solid Dispersion:
1.) 30 mg of crystalline material of Example 18, Batch E was weighed into a lyophilization vial
2.) 30 mg of HPMC603 (Hydroxypropylmethylcellulose grade 603) was added to the same vial
3.) 5.6 ml of Dioxane was added to the vial. The vial was closed with a lid.
4.) Sample was stirred at ambient conditions for 12 h
5.) Obtained solution was freeze-dried according to the following conditions

| Temperature [° C.] | Time [min] | Pressure [ybar] | Temperature Condenser [° C.] |
|---|---|---|---|
| Thermal Treatment | | | |
| −20 | 30 | 2500 | −40 |
| −20 | 60 | 2500 | −40 |
| Primary Drying | | | |
| 25 | 180 | 2000 | −40 |
| 25 | 60 | 500 | −40 |
| 25 | 120 | 100 | −40 |
| Post Heat | | | |
| 25 | 1000 | 2000 | −40 |

When providing a compound of the invention as a solid dispersion, prepared for example by combining the compound with a carrier (such as a polymer, e.g. HPMC) and solvent and freeze-drying the mixture (with the intention to provide the compound in amorphous form, rather than in crystalline form), for stability reasons it may be advantageous to increase the ratio of the amount of carrier to the amount of compound to avoid re-crystallisation of the compound upon standing.

In certain instances, it may be advantageous to administer the compound of the present invention in combination with at least one additional pharmaceutical (or therapeutic) agent (e.g., an anti-proliferative or anti-cancer agent or adjunct therapy typically used in chemotherapy). The compound of the present invention may be administered either simultaneously with, or before or after, one or more other therapeutic agent(s). Alternatively, the compound of the present invention may be administered separately, by the same or different route of administration, or together in the same pharmaceutical composition as the other agent(s). Suitable additional anti-cancer agents include but are not limited to, HER2 and HER3 receptor inhibitors: As recently exemplified in HER2 positive breast cancer models, PI3K inhibition will lead to pathway reactivation, through a FoxO dependent HER2/HER3 transcriptional induction, implying the use of HER2 inhibitors in this setting (Serra et al, 2011 Oncogene 30; Chandarlapaty et al, 2011 Cancer Cell 19; Chakrabarty et al 2012, PNAS 109). For example Trastuzumab (sold under the trademark Herceptin® by Genentech/Roche), pertuzumab (sold under the trademark Perjeta™, by Genentech/Roche), the antibody-drug conjugate Trastuzumab Emtansine (T-DM1) from Genentech/Roche, erlotinib (sold under the trademark Tarceva®, by Genentech/Roche, gefitinib (sold under the trademark Iressa™, by AstraZeneca), MOR10703, neratinib (also known as HKI-272, (2E)-N-[[3-chloro-4-[(pyridin-2-yl)methoxy]phenyl]amino]-3-cyano-7-ethoxyquinolin-6-yl]-4-(dimethylamino)but-2-enamide, and described in PCT Publication No. WO 05/028443), lapatinib or lapatinib ditosylate (sold under the trademark Tykerb® by GlaxoSmithKline). Such combination being useful in for example HER2 positive breast cancers and HER2 amplified gastric cancers. As a therapeutic target, HER3 (ErbB3) presents with the challenge of having an inactive tyrosine kinase, thus precluding the utility of ATP-mimetic tyrosine kinase inhibitors (TKIs). Circumventing this challenge are antibody-mediated strategies aimed at blocking ligand binding to ErbB3 (e.g., MM-121) or blocking the dimerization of ErbB3 with ErbB2 in ErbB2-overexpressing cells (e.g, pertuzumab)

Estrogen receptor downregulators/aromatase inhibitors: For example Fulvestrant (sold under the tradename Faslodex®), Letrozole (sold under the trademark Femara® by Novartis) or Exemestane (sold under the trademark Aromasin® by Pfizer). Such combination being useful in the treatment of for example ER positive breast cancer. The rationale for the combination being aimed to address PI3K related hormone resistance.

Mitogen-activated protein kinase kinase (MEK) inhibitors: For example XL-518 (Cas No. 1029872-29-4, available from ACC Corp.), AZD6244 or selumetinib (AstraZeneca), GSK1120212 (GlaxoSmithKline), AZD8330 (AstraZeneca), or MEK162. Such combination being useful in the treatment of for example KRAS mutant lung, colorectal cancer (CRC) and pancreatic cancers.

Bcl2/BclXL inhibitors: for example ABT737 (Abbott).

Anti-androgens: For example Nilutamide (sold under the tradenames Nilandron® and Anandron®), bicalutamide (sold under tradename Casodex®), flutamide (sold under the tradename Fulexin™), MDV3100 (Enzalutamide, sold under the tradename Xtandi® by Medivation) and Abiraterone (sold under the tradename Zytiga® by Janssen). Such combination being useful in the treatment of for example hormone dependent prostate cancer with PTEN inactivation. The rationale for the combination being aimed to address cross talk between PI3K and Androgen Receptor pathways.

Heat Shock Protein90 (HSP90) inhibitors: For example Tanespimycin (17-allylamino-17-demethoxygeldanamycin, also known as KOS-953 and 17-AAG, available from SIGMA, and described in U.S. Pat. No. 4,261,989) and 5-(2, 4-Dihydroxy-5-isopropyl-phenyl)-4-(4-morpholin-4-ylmethyl-phenyl)-isoxazole-3-carboxylic acid ethylamide (also known as AUY922 and described in PCT Publication No. WO2004/072051). Such combination being useful in the treatment of for example EGFR dependent lung cancers, or for inhibiting EGRmut which become refractory to EGR inhibitors, or in HER2 positive breast cancer, or HER2 positive gastric cancer.

Taxane anti-neoplastic agents: For example Cabazitaxel (1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis (acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate);

Anti-mitotic agents: For example Docetaxel (sold under the tradename Taxotere® by Sanofi-Aventis), useful for the treatment of breast cancer.

Plant Alkaloids: For example paclitaxel (sold under the tradenames Taxol and Onxal™) and Paclitaxel protein-bound (sold under the tradename Abraxane®) and useful for the treatment of prostate cancer, vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®) and vinorelbine (sold under the tradename Navelbine®).

Anti-Insulin-like Growth Factor-1 receptor (IGF-1R) antibodies: For example Figitumumab (also known as CP-751, 871, available from ACC Corp), and robatumumab (CAS No. 934235-44-6).

PARP (poly ADP-ribose polymerase) inhibitors: For example BSI-201 (iniparib) and olaparib. Such combination being useful in for example addressing possible induction of DNA damage machinery by PI3K inhibitors.

Suitable therapeutic agents for adjunct therapy include steroids, anti-inflammatory agents, anti-histamines, anti-emetics, and other agents well-known to those of skill in art for use in improving the quality of care for patients being treated for the diseases, conditions, or disorders described herein.

Because activation of the PI3K/Akt pathway drives cell survival, inhibition of the pathway in combination with therapies that drive apoptosis in cancer cells, including radiotherapy and chemotherapy, may result in improved responses (Ghobrial et al., CA Cancer J. Clin 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer. Ther. 4:1764-1771 (2005)). Compounds of the present invention may be administered in conjunction with radiotherapy.

The compound of the present invention or pharmaceutical composition thereof can be administered by the following routes: enteral, such as nasal; rectal or oral; parenteral, such as intramuscular or intravenous; or topical, such as dermal administration. The compound of the present invention or pharmaceutical composition thereof for use in humans is preferably administered orally (e.g. in tablet form).

The pharmaceutical composition or combination of the present invention can be in unit dosage of about 1 mg to about 1000 mg of active ingredient(s) for a subject of about 50 kg to about 70 kg, or about 1 mg to about 500 mg or about 1 mg to about 250 mg or about 1 mg to about 150 mg or about 0.5 mg to about 100 mg, or about 1 mg to about 50 mg of active ingredients. Unit dosage can also be of about 50 mg to about 1000 mg of active ingredient(s) for a subject of about 50 kg to about 70 kg, or about 50 mg to about 500 mg or about 50 mg to about 250 mg or about 50 mg to about 150 mg or about 50 mg to about 100 mg of active ingredients. Unit dosage can also be of about 100 mg to about 500 mg of active ingredient(s) for a subject of about 50 kg to about 70 kg, or about 200 mg to about 500 mg or about 300 mg to about 500 mg or about 300 mg to about 400 mg of active ingredients. These dosages may be provided as the total daily dosage, and may be provided in unit dosage or in split dosages. The dosage may depend upon the particular dosage form used for delivering the active ingredient(s). In general, the therapeutically effective dosage of a compound, the pharmaceutical composition, or the combinations thereof, is dependent on the species of the subject, the body weight, age and individual condition, the disorder or disease or the severity thereof being treated. The dosage can also depend on the bioavailability of the active ingredient in the species being treated. A physician, pharmacist, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions prepared from e.g. 10 mM DMSO stock solution, and in vivo either enterally, parenterally, advantageously intravenously, e.g., as a suspension or in aqueous solution. The dosage in vitro may range between about $10^{-3}$ molar and about $10^{-9}$ molar concentrations. A therapeutically effective amount in vivo may range depending on the route of administration, between about 0.1 to about 500 mg/kg, or between about 1 to about 100 mg/kg.

In general, a therapeutically effective amount of a compound of the present invention is administered to a patient in need of treatment. The term "a therapeutically effective amount" of a compound of the present invention refers to an amount of the compound of the present invention that will elicit the biological or medical response of a subject, for example, reduction or inhibition of an enzyme activity or a protein activity or a protein complex activity, or ameliorate symptoms, alleviate conditions, slow or delay disease progression, or prevent a disease, etc.

In yet another aspect, a method for treating cancer in a mammal is provided which comprises administering to a mammal in need of such treatment an effective amount of a compound of the present invention.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. Preferably, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder, refers (i) to ameliorating the disease or disorder (i.e., slowing or arresting or reducing the development of the disease or at least one of the clinical symptoms thereof); (ii) to alleviating or ameliorating at least one physical parameter including those which may not be discernible by the patient; or (iii) to preventing or delaying the onset or development or progression of the disease or disorder. In general, the term "treating" or "treatment" describes the management and care of a patient for the purpose of combating the disease, condition, or disorder and includes the administration of a compound of the present invention to prevent the onset of the symptoms or complications, alleviating the symptoms or complications, or eliminating the disease, condition or disorder.

As used herein, a subject is "in need of" a treatment if such subject would benefit biologically, medically or in quality of life from such treatment (preferably, the subject is a human).

Another aspect of the invention is a product comprising a compound of the present invention and at least one other therapeutic agent (or pharmaceutical agent) as a combined preparation for simultaneous, separate or sequential use in therapy to enhance apoptosis.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the present invention for treating a disease or condition by inhibiting or antagonizing PI3K, wherein the medicament is prepared for administration with another therapeutic agent. The invention also provides for the use of another therapeutic agent, wherein the medicament is administered as a combination of a compound of the present invention with the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), Chem-Impex International, Inc. (Wood Dale, Ill.), and AstraZeneca Pharmaceuticals (London, England).

The abbreviations used in the following Examples have the corresponding meanings listed below.

AcOH acetic acid
$AlCl_3$ aluminium trichloride
API atmospheric pressure ionization
Boc tert-butoxycarbonyl
Brine saturated (at rt) sodium chloride solution
br. s broad singulet
$^n$BuOH n-butanol
$^t$Bu tert-butyl
CDI carbonyl diimidazole
Celite trademark of Celite Corp. (World Minerals Inc.), Santa Barbara, Calif., USA, for filtering aid based on kieselguhr
$CH_3CN$ acetonitrile
conc. concentrated
d doublett
DCE dichloroethane
DCM dichloromethane
DEA diethylamine
DIEA N,N-diethyl-isopropylamine
DMAP 4-dimethylaminopyridine
DME dimethoxyethane
DMF N,N-dimethylformamide
DMSO dimethylsulfoxide
ES-MS electrospray mass spectrometry
Et ethyl
$Et_3N$ triethylamine
$Et_2O$ diethyl ether
EtOAc ethyl acetate
EtOH ethanol
H hour(s)
HPLC high-performance liquid chromatography
Hyflo Hyflo Super Cel®
iPr isopropyl
$K_2CO_3$ potassium carbonate
KOH potassium hydroxide
$K_3PO_4$ potassium phosphate
LAH lithium aluminium hydride
LC liquid chromatography
Me methyl
MeI methyl iodide
MeOH methanol
$MgSO_4$ magnesium sulfate
M multiplett
min minute(s)
mL milliliter(s)
m.p. melting point
MS Mass Spectrometry
NaH sodium hydride
$NaHCO_3$ sodium bicarbonate
$Na_2CO_3$ sodium carbonate
NaHMDS sodium hexamethyldisilazane
NaOH sodium hydroxide
$Na_2SO_4$ sodium sulfate
$MgSO_4$ magnesium sulfate
NaOAc sodium acetate
NBS N-bromosuccinimide
$NH_4Cl$ ammonium chloride
$NH_4OH$ ammonium hydroxide
NMR nuclear magnetic resonance
$POCl_3$ phosphorus (III) oxychloride
RT room temperature
$R_f$ TLC retention factor
S singulet
$scCO_2$ super critical $CO_2$
t triplet
TBAF tetrabutylammonium fluoride
TBDPSCl tert-Butyldiphenylsilyl chloride
TBME tert-butylmethylether
TEA triethylamine
TEMPO 2,2,6,6-tetramethylpiperidinyloxyl
TFA trifluoroacetic acid
THF tetrahydrofurane
TLC thin layer chromatography
TMS trimethylsilyl
TMSCl trimethylsilyl chloride
$t_R$ time of retention
TsCl p-toluenesulfonyl chloride
TsOH p-toluenesulfonic acid
UV ultraviolet General Method 1H-NMR measurements were performed on a Bruker Ultrashield™ 400 (400 MHz), Bruker Ultrashield™ 600 (600 MHz) or a 500 MHz DRX Bruker CryoProbe (500 MHz) spectrometer using or not trimethylsilane as an internal standard. Chemical shifts (d-values) are reported in ppm downfield from tetramethylsilane, coupling constants (J) are given in Hz, spectra splitting pattern are designated as singulet (s), doublet (d), doublet doublet (dd), triplet (t), quadruplet (q), multiplet or more overlapping signals (m), broad signal (br). Solvents are given in parentheses.

TLC were performed with precoated silica gel 60 $F_{254}$ glass plates (Merck, Darmstadt, Germany) using the respective named solvent systems. Visualization was generally done by UV light (254 nm).

HPLC Conditions:

LC-MS 1:

Column: Acquity HSS T3 2.1×50 mm, 1.8 μm. Flow: 1.2 mL/min. Column temperature: 50° C.
Gradient: 2% to 98% B in 1.4 min, 98% B for 0.75 min, 98% to 2% B in 0.04 min, 2% B for 0.01 min; A=water+0.05% formic acid+3.75 mM ammonium acetate, B=acetonitrile+0.04% formic acid
Detection full scan: 215-350 nm

LC-MS 2:

Column: Acquity HSS T3 2.1×50 mm, 1.8 μm. Flow: 1.2 mL/min. Column temperature: 50° C.
Gradient: 2% to 98% B in 1.4 min, 98% B for 0.75 min, 98% to 2% B in 0.04 min, 2% B for 0.01 min; A=water+0.05% formic acid+0.05% ammonium acetate, B=acetonitrile+0.04% formic acid
Detection full scan: 215-350 nm

LC-MS 3:

Column: Acquity HSS T3 2.1×50 mm, 1.8 μm. Flow: 1.0 mL/min. Column temperature: 60° C.
Gradient: 5% to 98% B in 1.4 min, 98% B for 0.75 min, 98% to 5% B in 0.04 min, 5% B for 0.01 min; A=water+0.05% formic acid+3.75 mM ammonium acetate, B=acetonitrile+0.04% formic acid
Detection full scan: 215-350 nm

HPLC 1:

Column: Chromolith performance RP18e 4.6×100 mm, Flow: 2.0 mL/min. Gradient: 2% to 100% B in 4.5 min, 100% B for 1 min, A=water+0.1% TFA, B=acetonitrile+0.1% TFA
Detection: 215 nm

UPLC 1:

Column: Acquity UPLC HSS T3 C18, 1.7 μm 2.1×50 mm, Flow: 1.0 mL/min. Gradient: 5% to 100% B in 1.5 min, 100% B for 1 min, A=water+0.1% TFA, B=acetonitrile+0.1% TFA
Detection: 218 nm Intermediate A:
4-(4,6-Dichloro-pyrimidin-2-yl)-morpholine Intermediate A is commercially available or can be prepared using the following procedure.

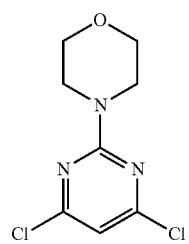 [SMILES: Clc1cc(Cl)nc(N2CCOCC2)n1]

To a solution of 2,4,6-trichloropyrimidine (5.0 mL, 42.6 mmol) in mesitylen (80 mL) at 165° C. was added dropwise a solution of morpholine (4.83 mL, 55.4 mmol) in mesitylen (20 mL) and the suspension was stirred at 165° C. for 30 min. The reaction mixture was treated with H₂O, EtOAc and NaHCO₃. The organic layer was washed with H₂O and brine, dried (Na₂SO₄), filtered and concentrated. The residue was purified by flash chromatography (hexane/EtOAc, 100:0→7:3). The residue was triturated in hexane and filtered to afford the title compound (3.36 g, 33%). $t_R$: 1.11 min (LC-MS 1); ESI-MS: 234.2 [M+H]⁺ (LC-MS 1).

Intermediate B: 5-(4,4,5,5-Tetramethyl-[1,3,2]dioxaborolan-2-yl)-4-trifluoromethyl-pyrimidin-2-ylamine

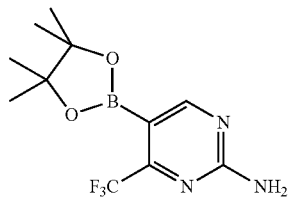 [SMILES: CC1(C)OB(c2cnc(N)nc2C(F)(F)F)OC1(C)C]

To a suspension of the product from step B.1 (16.2 g, 66.3 mmol), bis-pinacolatodiboron (18.5 g, 72.9 mmol) and KOAc (19.5 g, 199 mmol) in dioxane (300 mL) under argon was added PdCl₂(dppf)CH₂Cl₂ adduct (2.4 g, 2.98 mmol) and the mixture was stirred at 115° C. for 4 h. The reaction mixture was cooled to 50° C. and treated with EtOAc. The resulting suspension was filtered over Hyflo and washed with EtOAc. The combined filtrated were concentrated. The residue was suspended in 2 N NaOH, stirred at RT for 5 min and then Et₂O and H₂O were added and the binary mixture was filtered through Hyflo. The phases of the filtrate were separated. The pH of the resulting aqueous layer was adjusted to 5-6 with HCl 4N and then extracted with EtOAc. The organic layer was washed with H₂O and brine, dried (Na₂SO₄), filtered and concentrated. The residue was triturated in Et₂O and hexane, filtered to afford the title compound (8.33 g, 42%). $t_R$: 1.00 min (LC-MS 1); ESI-MS: 290.3 [M+H]⁺ (LC-MS 1).

Step B1:
5-Bromo-4-trifluoromethyl-pyrimidin-2-ylamine

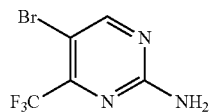

To a solution of 2-amino-4-trifluoromethylpyrimidine (25 g, 0.15 mol) in CH₃CN (800 mL) was added dropwise (over 2.5 hours) NBS (34.8 g, 0.195 mol) dissolved in 200 mL of CH₃CN in the dark. The mixture was stirred 4.5 h at RT in the dark and then the solvent was evaporated. The residue was dissolved in EtOAc and H2O and the binary mixture was transferred into a separating funnel. The aqueous layer was separated and extracted with EtOAc. The organic layers were washed with H2O and brine, dried with Na2SO4, filtered and evaporated. The residue was purified by chromatography on silica gel using a gradient of hexane/EtOAc 9:1 to 3:2. The combined pure fractions were evaporated and the residue suspended in 40 mL hexane, stirred for 10 min., filtered and washed with 2×20 mL of hexane to give the title product as a beige solid (31.2 g, 85%). $t_R$: 0.82 min (LC-MS 1).

Example 1

(S)-3-(2'-Amino-2-morpholin-4-yl-4'-trifluoromethyl-[4,5']bipyrimidinyl-6-yl)-4-methyl-oxazolidin-2-one

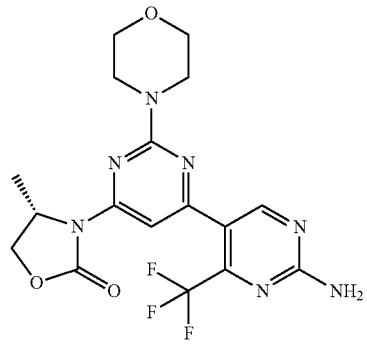 [SMILES: C[C@H]1COC(=O)N1c1cc(-c2cnc(N)nc2C(F)(F)F)nc(N2CCOCC2)n1]

A solution of product from step 1.1 (350 mg, 1.16 mmol), intermediate B (449 mg, 1.51 mmol), Na$_2$CO$_3$(2M, 1.7 mL, 3.48 mmol) and PdCl$_2$(dppf)-CH$_2$Cl$_2$(95 mg, 0.17 mmol) in DME (10 mL) under argon was stirred at 80° C. for 1 h. The mixture was diluted in EtOAc and extracted with saturated NaHCO$_3$. The organic layer was washed with H$_2$O and brine, dried (Na$_2$SO$_4$), filtered and concentrated. The residue was purified by flash chromatography (CH$_2$Cl$_2$/EtOH, 99.5:0.5→98:2). The residue was triturated in hexane, filtered and dried. The residue was purified by preparative HPLC (Waters Sun Fire C18, 30×100 mm, 5 um; 0.1% TFA-water/acetonitrile; gradient acetonitrile 5-100% in 20 min) to afford the title compound (260 mg, 52%). $t_R$: 0.93 min (LC-MS 1); ESI-MS: 426.3 [M+H]$^+$ (LC-MS 1).

Step 1.1: (S)-3-(6-Chloro-2-morpholin-4-yl-pyrimidin-4-yl)-4-methyl-oxazolidin-2-one

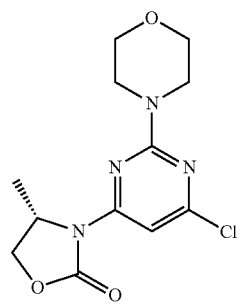 [SMILES: C[C@H]1COC(=O)N1c1cc(Cl)nc(N2CCOCC2)n1]

To a solution of (S)-4-methyl-2-oxazolidinone (432 mg, 4.19 mmol) in DMF (10 mL) was slowly added NaH (60% mineral oil, 201 mg, 5.02 mmol) under an argon atmosphere and the suspension was stirred at rt for 30 min. The reaction mixture was cooled to 0° C. and the intermediate A (1 g, 4.19 mmol) was added. The mixture was stirred at RT for 4 h. The reaction mixture was diluted with EtOAc and extracted with H$_2$O. The organic layer was washed with H$_2$O and brine, dried (Na$_2$SO$_4$), filtered and concentrated. The residue was purified by flash chromatography (hexane/EtOAc, 97:3→1:1) to afford the title compound (605 mg, 47%). $t_R$: 1.00 min (LC-MS 1); ESI-MS: 299.2/301.2 [M+H]$^+$ (LC-MS 1).

Example 2

(S)-3-(2'-Amino-2-morpholin-4-yl-4'-trifluoromethyl-[4,5']bipyrimidinyl-6-yl)-4-hydroxymethyl-5,5-dimethyl-oxazolidin-2-one

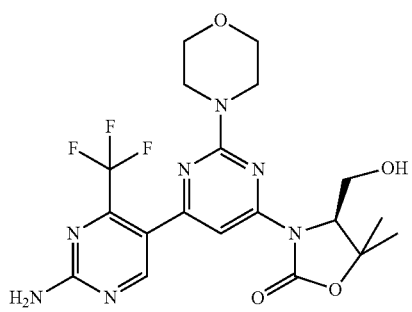 [SMILES: CC1(C)OC(=O)N(c2cc(-c3cnc(N)nc3C(F)(F)F)nc(N3CCOCC3)n2)[C@H]1CO]

A solution of the product from step 2.1 (28 mg, 0.04 mmol) and TBAF (2 mL, 2.0 mmol, 1M in THF) was stirred at rt overnight. The reaction mixture was concentrated and the residue was purified by flash chromatography (DCM/MeOH, 100:0→95:5) to give the title product. $t_R$: 0.89 min (LC-MS 1); ESI-MS: 470.2 [M+H]$^+$ (LC-MS 1).

Step 2.1: (S)-3-(2'-Amino-2-morpholin-4-yl-4'-trifluoromethyl-[4,5']bipyrimidinyl-6-yl)-4-(tert-butyl-diphenyl-silanyloxymethyl)-5,5-dimethyl-oxazolidin-2-one

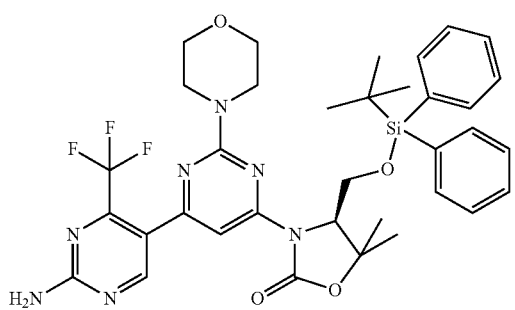 [SMILES: CC1(C)OC(=O)N(c2cc(-c3cnc(N)nc3C(F)(F)F)nc(N3CCOCC3)n2)[C@H]1CO[Si](c1ccccc1)(c1ccccc1)C(C)(C)C]

The title compound was prepared in analogy to the procedure used for example 1 but using the product from step 2.2. The mixture was performed at 100° C. for 40 min. After extraction, the residue was purified by flash chromatography (heptane/EtOAc, 100:0→30:70) to give the title product. $t_R$: 1.45 min (LC-MS 1); ESI-MS: 708.4 [M+H]$^+$ (LC-MS 1).

Step 2.2: (S)-4-(tert-Butyl-diphenyl-silanyloxymethyl)-3-(6-chloro-2-morpholin-4-yl-pyrimidin-4-yl)-5,5-dimethyl-oxazolidin-2-one

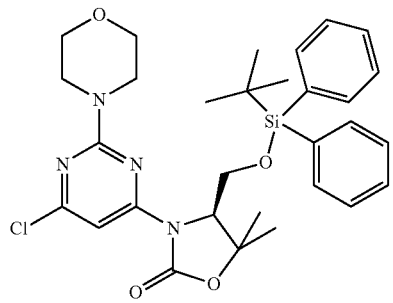 [SMILES: CC1(C)OC(=O)N(c2cc(Cl)nc(N3CCOCC3)n2)[C@H]1CO[Si](c1ccccc1)(c1ccccc1)C(C)(C)C]

A solution of the product from step 2.3 (95 mg, 0.25 mmol), intermediate A (58 mg, 0.25 mmol), xantphos (10 mg, 0.02 mmol), Pd$_2$dba$_3$ (4.5 mg, 4.95 umol) and Cs$_2$CO$_3$ (121 mg, 0.37 mmol) in dioxane under argon was stirred at 100° C. for 3 h. The mixture was cooled to rt, diluted with EtOAc and extracted with a saturated NaHCO$_3$ solution. The organic layer was washed with brine, dried (Na$_2$SO$_4$), filtered and concentrated. The residue was purified by flash chromatography (heptane/EtOAc, 100:0→0:100) to give the title product (85 mg, 56%). $t_R$: 1.54 min (LC-MS 1); ESI-MS: 581.4/583.3 [M+H]$^+$ (LC-MS 1).

Step 2.3: (S)-4-(tert-Butyl-diphenyl-silanyloxymethyl)-5,5-dimethyl-oxazolidin-2-one

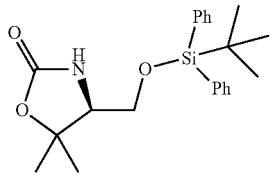 [SMILES: CC1(C)OC(=O)N[C@H]1CO[Si](c1ccccc1)(c1ccccc1)C(C)(C)C]

The title compound was prepared in analogy to the procedure used for step 6.2 but using the product from step 2.4, and using Et$_3$N instead of imidazole. The mixture was stirred at RT for 16 h. The reaction mixture was concentrated and purified by flash chromatography (heptane/EtOAc, 100:0→55:45) to give the title product. $t_R$: 1.33 min (LC-MS 1); ESI-MS: 384.3 [M+H]$^+$ (LC-MS 1).

Step 2.4: (S)-4-Hydroxymethyl-5,5-dimethyl-oxazolidin-2-one

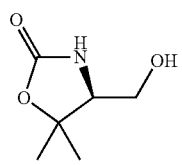

A solution of the product from step 2.5 (110 mg, 0.59 mmol) and HCl (4M in dioxane, 5 mL, 20 mmol) was stirred at RT for 4 h. The reaction mixture was concentrated and the residue was used without further purification.

Step 2.5: (S)-1,1,5,5-Tetramethyl-dihydro-oxazolo[3,4-c]oxazol-3-one

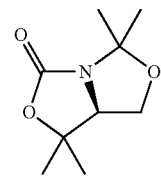

To a solution of the product from step 2.6 (190 mg, 0.73 mmol) in DMF (6 mL) under argon at 0° C. was added NaH (88 mg, 2.20 mmol, 60% in oil) and the mixture was stirred at 0° C. for 6 h. The reaction mixture was quenched with H$_2$O and concentrated. The residue was triturated in EtOAc and filtered. The filtered solution was dried (Na$_2$SO$_4$), filtered and concentrated. The product was purified by flash chromatography (heptane/EtOAc, 100:0→60:40).

Step 2.6: (S)-4-(1-Hydroxy-1-methyl-ethyl)-2,2-dimethyl-oxazolidine-3-carboxylic acid tert-butyl ester

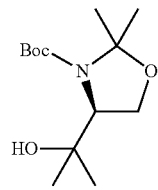

To a solution of (S)-3-tert-butyl 4-methyl 2,2-dimethyloxazolidine-3,4-dicarboxylate (500 mg, 1.93 mmol) in THF (15 mL) under argon at 0° C. was added dropwise methylmagnesium bromide (1.4 mL, 4.24 mmol) and the mixture was stirred at 0° C. for 2 h. The reaction was quenched with a saturated NH$_4$Cl solution and extracted with EtOAc. The organic layer was washed with brine, dried (Na$_2$SO$_4$), filtered and concentrated. The residue was purified by flash chromatography (heptane/EtOAc, 100:0→65:35). $t_R$: 1.01 min (LC-MS 1); ESI-MS: 260.3 [M+H]$^+$ (LC-MS 1).

Example 3

Racemic 3-(2'-amino-2-morpholino-4'-(trifluoromethyl)-4,5'-bipyrimidin-6-yl)-4-(hydroxymethyl)-4-methyloxazolidin-2-one

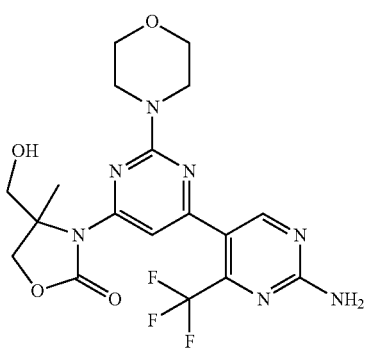 [SMILES: CC1(CO)COC(=O)N1c1cc(-c2cnc(N)nc2C(F)(F)F)nc(N2CCOCC2)n1]

A solution of intermediate B (68 mg, 0.21 mmol), the product from step 3.1 (120 mg, 021 mmol), a 2M Na$_2$CO$_3$ solution (317 uL, 0.63 mmol) and tetrakis (15 mg, 0.01 mmol) in DME (2 mL) was stirred at 80° C. for 3 h. The reaction mixture was diluted in EtOAc and Na$_2$SO$_4$ was added. The resulting suspension was filtered and the filtrate was concentrated. The residue was dissolved with THF (2 ML) and TBAF (212 uL, 0.21 mmol) was added. The mixture was stirred at rt for 16 h and was concentrated. The crude was purified by flash chromatography (DCM/EtOH, 99:1→96:4). The residue was triturated in DCM/hexane to afford the title compound. t$_R$: 0.85 min (LC-MS 1); ESI-MS: 456.3 [M+H]$^+$ (LC-MS 1).

Step 3.1: 4-(tert-Butyl-diphenyl-silanyloxymethyl)-3-(6-chloro-2-morpholin-4-yl-pyrimidin-4-yl)-4-methyl-oxazolidin-2-one

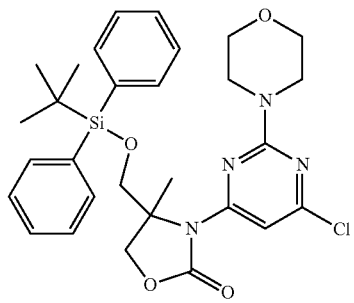 [SMILES: CC1(CO[Si](c2ccccc2)(c2ccccc2)C(C)(C)C)COC(=O)N1c1cc(Cl)nc(N2CCOCC2)n1]

The title compound was prepared in analogy to the procedure described for step 2.2 but using product from step 3.2. After extraction, the residue was purified by flash chromatography (hexane/EtOAc: 9:1→1:1) to give the title compound.

Step 3.2: 4-(tert-Butyl-diphenyl-silanyloxymethyl)-4-methyl-oxazolidin-2-one

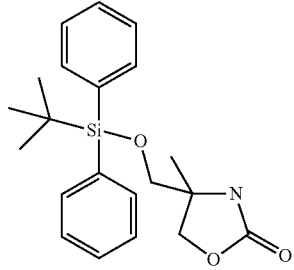 [SMILES: CC1(CO[Si](c2ccccc2)(c2ccccc2)C(C)(C)C)COC(=O)N1]

The title compound was prepared in analogy to the procedure described for step 6.4 but using 4-(hydroxymethyl)-4-methyloxazolidin-2-one, and using DCM instead of DMF. The reaction mixture was extracted with Et$_2$O. The organic layer was washed with H$_2$O and brine, dried (Na$_2$SO$_4$), filtered and concentrated. The resulting solid was triturated in hexane and filtered to afford the title compound. t$_R$: 1.20 min (LC-MS 1); ESI-MS: 339.2/341.2 [M+H]$^+$ (LC-MS 1).

Example 3A

First eluting enantiomer of 3-(2'-amino-2-morpholino-4'-(trifluoromethyl)-4,5'-bipyrimidin-6-yl)-4-(hydroxymethyl)-4-methyloxazolidin-2-one Absolute stereochemistry not determined.

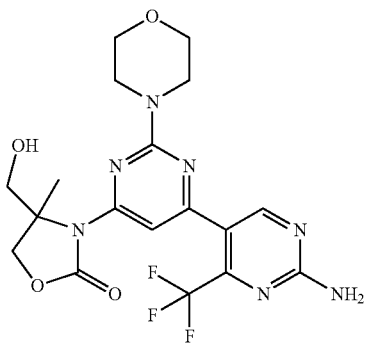 [SMILES: CC1(CO)COC(=O)N1c1cc(-c2cnc(N)nc2C(F)(F)F)nc(N2CCOCC2)n1]

The title compound was obtained after preparative chiral SFC separation of the racemic product of example 3. (Column: Chiralpak AD-H, 30×250 mm. Flow 80 mL/min. scCO$_2$/MeOH 85:15). t$_R$: 3.97 min (Column: Chiralpak AD-H, 4.6×250 mm. Flow 3 mL/min. scCO$_2$/MeOH 85:15).

Example 3B

Second eluting enantiomer of 3-(2'-amino-2-morpholino-4'-(trifluoromethyl)-4,5'-bipyrimidin-6-yl)-4-(hydroxymethyl)-4-methyloxazolidin-2-one Absolute stereochemistry not determined.

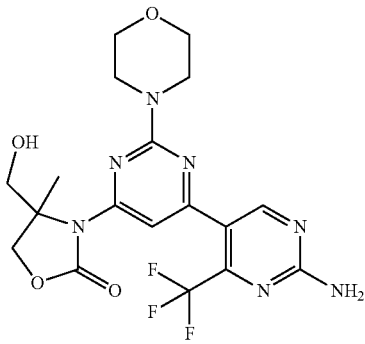 [SMILES: CC1(CO)COC(=O)N1c1cc(-c2cnc(N)nc2C(F)(F)F)nc(N2CCOCC2)n1]

The title compound was obtained after preparative chiral SFC separation of the racemic product of example 3. (Column: Chiralpak AD-H, 30×250 mm. Flow 80 mL/min.

scCO₂/MeOH 85:15). $t_R$: 4.49 min (Column: Chiralpak AD-H, 4.6×250 mm. Flow 3 mL/min. scCO₂/MeOH 85:15).

Example 4

(3aS,7aS)-3-(2'-Amino-2-morpholin-4-yl-4'-trifluoromethyl-[4,5']bipyrimidinyl-6-yl)-hexahydro-benzooxazol-2-one

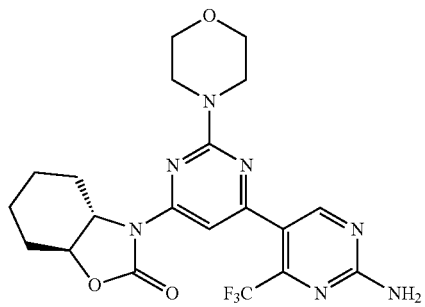 [SMILES: Nc1ncc(-c2cc(N3C(=O)O[C@H]4CCCC[C@@H]43)nc(N3CCOCC3)n2)c(C(F)(F)F)n1]

A solution of product from step 4.1 (60 mg, 0.17 mmol), intermediate B (54 mg, 0.17 mmol), Na₂CO₃ (2M, 260 μL, 0.52 mmol) and palladium tetrakis (10 mg, 8.7 μmol) in DME (1.5 mL) under argon was stirred at 80° C. for 2 h in a sealed vial. The reaction mixture was concentrated. The residue was purified by flash chromatography (CH₂Cl₂/EtOH, 99.8:0.2→97.5:2.5). The residue was dissolved in DCM (2 mL) and then treated in hexane (4 mL). The crystals were filtered and washed with hexane (3 ml) to give the title compound (36 mg, 44%). $t_R$: 1.10 min (LC-MS 1); ESI-MS: 466.3 [M+H]⁺ (LC-MS 1).

Step 4.1: (3aS,7aS)-3-(6-Chloro-2-morpholin-4-yl-pyrimidin-4-yl)-hexahydro-benzooxazol-2-one

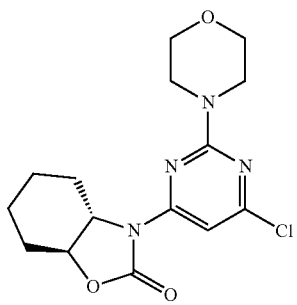 [SMILES: O=C1O[C@H]2CCCC[C@@H]2N1c1cc(Cl)nc(N2CCOCC2)n1]

The title compound was prepared in analogy to the procedure described for step 2.2, but using product from step 4.2. The reaction was performed at 100° C. for 1 h. The reaction mixture was filtered through Hyflo and concentrated. The residue was purified by flash chromatography (hexane/EtOAc: 9:1→1:1) to give the title compound. $t_R$: 1.20 min (LC-MS 1); ESI-MS: 339.2/341.2 [M+H]⁺ (LC-MS 1).

Step 4.2: (3aS,7aS)-Hexahydro-benzooxazol-2-one

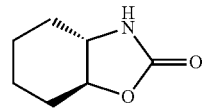

The (1S,2S)-2-Aminocyclohexanole (750 mg, 6.51 mmol) and the 2-Nitrophenyl chloroformate (1378 mg, 6.84 mmol) were stirred in DCE (15 mL) with DIEA (2.39 mL, 13.68 mmol) in a sealed vial at 90° C. for 1 h. The reaction mixture was given into a separating funnel with 50 mL EtOAc and 50 mL saturated NaHCO₃ solution. The aqueous layer was washed with 50 mL EtOAc. The organic layers were combined and washed with 50 mL H2O, 50 mL brine, dried with Na₂SO₄, filtered and concentrated. The residue was purified by flash chromatography (hexane/EtOAc: 7:3→3:7) to give the title compound (770 mg, 5.13 mmol). $t_R$: 0.69 min (LC-MS 1); ¹H NMR (400 MHz, <dmso>) δ ppm 1.19-1.44 (m, 3H) 1.45-1.61 (m, 1H) 1.65 (d, J=9.77 Hz, 1H) 1.76 (d, J=11.34 Hz, 1H) 1.82-1.93 (m, 1H) 1.93-2.10 (m, 1H) 3.03-3.23 (m, 1H) 3.74 (td, J=11.34, 3.52 Hz, 1H) 7.53 (br. s., 1H)

Example 5

(S)-3-(2'-Amino-2-morpholin-4-yl-4'-trifluoromethyl-[4,5']bipyrimidinyl-6-yl)-4-methoxymethyl-oxazolidin-2-one

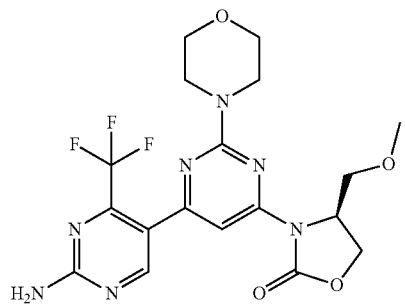 [SMILES: COC[C@H]1COC(=O)N1c1cc(-c2cnc(N)nc2C(F)(F)F)nc(N2CCOCC2)n1]

In a microwave vial, to a solution of product from step 5.1 (116 mg, 0.28 mmol) and intermediate B (90 mg, 0.31 mmol) in DME (2.1 mL) were added saturated Na₂CO₃ solution (0.7 ml) and PdCl₂(dppf)₂·CH₂Cl₂ (23 mg, 0.03 mmol). The mixture was bubbled with argon for 5 min. It was stirred at 120° C. for 15 min under microwave irradiations. The reaction mixture was taken up in DCM and water. Layers were separated and aqueous layer was extracted twice more with some DCM. Then organic layers were combined, dried over sodium sulfate and evaporated. The residue was purified by flash chromatography (DCM/MeOH: 100%→95% DCM). The residue obtained was purified by reverse phase flash chromatography (MeCN/H₂O: 10%→100% MeCN) to give the title compound (19 mg, 13%). $t_R$: 0.91 min (LC-MS 1); ESI-MS: 456.1 [M+H]⁺ (LC-MS 1).

Step 5.1: (S)-3-(6-Chloro-2-morpholin-4-yl-pyrimidin-4-yl)-4-methoxymethyl-oxazolidin-2-one

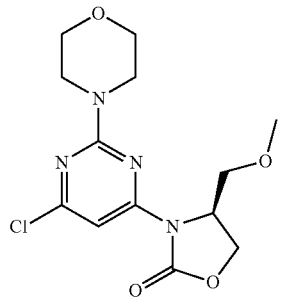 [SMILES: COC[C@H]1COC(=O)N1c1cc(Cl)nc(N2CCOCC2)n1]

The title compound was prepared in analogy to the procedure described for step 2.2, but using product from step 5.2. The reaction was performed at 115° C. for 80 min. The reaction mixture was concentrated and taken up with DCM/water. The layers were separated and the aqueous one was extracted three times with DCM. The organic layers were combined and dried over sodium sulfate. The residue was purified by flash chromatography (heptane/EtOAc: 100%→60% heptane.) to give the title compound (116 mg, 22%). $t_R$: 0.98 min (LC-MS 1); ESI-MS: 329.2 [M+H]$^+$ (LC-MS 1).

Step 5.2: (S)-4-Methoxymethyl-oxazolidin-2-one

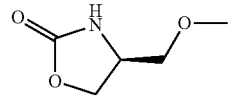

TsOH (800 mg, 4.21 mmol) was added to a yellow solution of product from step 5.3 (1.013 g, 4.13 mmol) in MeOH (10 ml). The mixture was stirred at RT for 90 min. Then TsOH (140 mg, 0.74 mmol) was added and it was stirred for 70 min at RT. Then solvent was removed and the residue was dissolved in DCM (6 mL) with Triethylamine (1.44 ml, 10.32 mmol). A solution of triphosgene (0.613 g, 2.07 mmol) in DCM (4 mL) was slowly added to the mixture. The reaction mixture was stirred at RT for 2 h 30. The reaction was quenched with a few drops of water. It was then acidified to pH=4 with buffer was added and then the layers were separated. The aqueous one was extracted once more with some DCM. Organic layers were combined, dried over sodium sulfate and evaporated. The residue was purified by flash chromatography (DCM/MeOH: 100%→90% DCM) to give the title compound (231 mg, 38%). ESI-MS: 132.1 [M+H]$^+$ (LC-MS 1).

Step 5.3: (S)-4-Methoxymethyl-2,2-dimethyl-oxazolidine-3-carboxylic acid tert-butyl ester

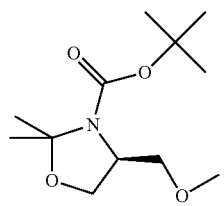

NaH (265 mg, 6.63 mmol) was added to a yellow solution of (S)-1-Boc-2,2-dimethyl-4-hydroxymethyloxazolidine (AstaTech Inc., Bristol, Pa.) (1 g, 4.19 mmol) in THF (10 ml). Then the mixture was stirred for 15 min at ambient temperature. The Methyliodid (323 µL, 5.19 mmol) was added to the yellow suspension and the mixture was stirred for 2 h 30 at rt. Then water was added to quench the reaction. The solvent was removed. The residue was purified by flash chromatography (DCM/MeOH: 5%→10% MeOH) to give the title compound (1.013 g, 94%). ESI-MS: 246.1 [M+H]$^+$ (LC-MS 1); $^1$H NMR (400 MHz, <cdcl3>) δ ppm 1.48 (s, 9H) 1.53 (br. s., 6H) 3.30 (m, 1H) 3.36 (s, 3H) 3.41-3.63 (m, 2H) 3.88-4.00 (m, 2H)

Example 6

(4S,5S)-3-(2'-Amino-2-morpholin-4-yl-4'-trifluoromethyl-[4,5']bipyrimidinyl-6-O-4-hydroxymethyl-5-methyl-oxazolidin-2-one

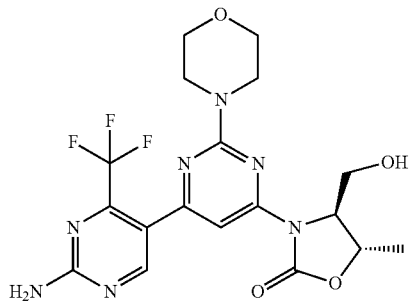 [SMILES: C[C@@H]1OC(=O)N(c2cc(-c3cnc(N)nc3C(F)(F)F)nc(N3CCOCC3)n2)[C@H]1CO]

A solution of product from step 6.1 (600 mg, 0.82 mmol) in THF (5 mL) was treated with HF.pyridine in THF (7.14 mL, 57.5 mmol) for 4 days at RT in a plastic vial. Then the reaction mixture was added dropwise to a stirred a mixture of saturated NaHCO$_3$ solution (300 mL) and EtOAc (200 mL). Then solid NaHCO3 was added until pH~8 and the layers were separated. The aqueous one was washed with 100 mL EtOAc, The organic extracts were combined and washed with water and brine. It was then dried over Na$_2$SO$_4$, filtered and evaporated. The crude was purified by flash chromatography (DCM/EtOH: 99:1→95:5). The fractions were combined and concentrated. The residue was sonicated in DCM and then hexane was added. The crystals obtained were filtered off and re-purified 3 times by flash chromatography (DCM/EtAOc: 9:1→3:7, then Hexane/THF: 9:1→1:1, then Hexane/THF: 7:3→1:1) to give the title compound (243 mg, 64%). $t_R$: 0.80 min (LC-MS 1); ESI-MS: 456.6 [M+H]$^+$ (LC-MS 1).

Step 6.1: (4S,5S)-3-(2'-Amino-2-morpholin-4-yl-4'-trifluoromethyl-[4,5']bipyrimidinyl-6-yl)-4-(tert-butyl-diphenyl-silanyloxymethyl)-5-methyl-oxazolidin-2-one

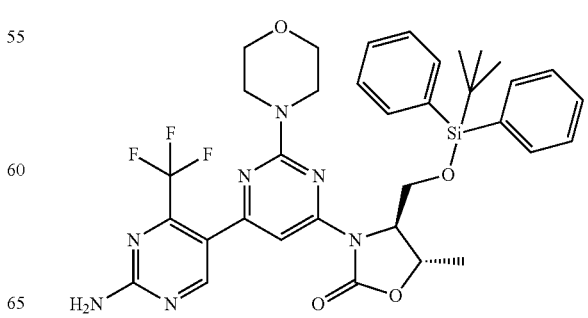

The title compound was prepared in analogy to the procedure described for example 1, but using product from step 6.2. The reaction was performed at 80° C. for 1 h. After extraction, the residue was purified by flash chromatography (DCM/EtOH: 95.5:0.5→97:3) to give the title compound. $t_R$: 1.43 min (LC-MS 1); ESI-MS: 694.5 [M+H]⁺ (LC-MS 1).

Step 6.2: (4S,5S)-4-(tert-Butyl-diphenyl-silanyloxymethyl)-3-(6-chloro-2-morpholin-4-yl-pyrimidin-4-yl)-5-methyl-oxazolidin-2-one

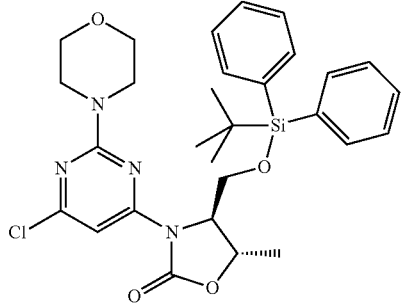 [SMILES: C[C@@H]1OC(=O)N(c2cc(Cl)nc(N3CCOCC3)n2)[C@H]1CO[Si](c1ccccc1)(c1ccccc1)C(C)(C)C]

The title compound was prepared in analogy to the procedure described for step 2.2, but using product from step 6.3. The reaction was performed at 100° C. for 3 h 30. The reaction mixture was taken up with EtOAc and washed with saturated NaHCO₃ solution and brine. The organic layer was and dried over sodium sulfate. The residue was purified by flash chromatography (heptane/EtOAc: 100%→30% heptane.) to give the title compound (116 mg, 22%). $t_R$: 1.51 min (LC-MS 1); ESI-MS: 567.4/569.5 [M+H]⁺ (LC-MS 1).

Step 6.3: (4S,5S)-4-(tert-Butyl-diphenyl-silanyloxymethyl)-5-methyl-oxazolidin-2-one

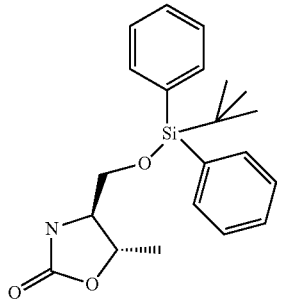 [SMILES: C[C@@H]1OC(=O)N[C@H]1CO[Si](c1ccccc1)(c1ccccc1)C(C)(C)C]

The product from step 6.4 (3.2 g, 9.31 mmol) was dissolved in DCM (32 ml) and treated with Et3N (3.25 ml, 23.29 mmol). The solution was flushed with Argon and stirred for 5 min at RT. Then, it was treated with Triphosgene (1.382 g, 4.66 mmol) and stirred at RT for 16H. The reaction was quenched with saturated NH4Cl solution (10 mL) and stirred 10 min at RT. The water layer was separated and the organic layer washed with water. The combined aqueous layer were extracted 3× with DCM. The combined organic layer were dried over Na₂SO₄, filtered and concentrated. The residue was purified by flash chromatography (heptane/EtOAc: 100%→50% heptane.) to give the title compound (2.22 g, 61%). $t_R$: 1.28 min (LC-MS 1); ESI-MS: 387.3 [M+18]⁺ (LC-MS 1).

Step 6.4: (2S,3S)-3-Amino-4-(tert-butyl-diphenyl-silanyloxy)-butan-2-ol

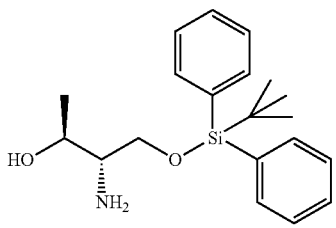 [SMILES: C[C@H](O)[C@@H](N)CO[Si](c1ccccc1)(c1ccccc1)C(C)(C)C]

D-threoninol (2 g, 19.02 mmol) was dissolved in DMF (15 ml), treated with imidazole (3.89 g, 57.1 mmol) and stirred at RT for 5 min. Then, TBDPS-Cl (5.13 ml, 19.97 mmol) was added dropwise to the reaction solution under argon. The reaction solution was stirred for 16H at RT. Then it was diluted in EtOAc and washed twice with saturated NaHCO₃ solution and once with brine. Organic layer was dried over Na₂SO₄, filtered and concentrated. The residue was purified by flash chromatography (heptane/EtOAc: 100%→0% heptane.) to give the title compound (3.21 g, 47%). $t_R$: 0.98 min (LC-MS 1); ESI-MS: 344.3 [M+H]⁺ (LC-MS 1).

Example 7

(S)-3-(2'-Amino-2-morpholin-4-yl-4'-trifluoromethyl-[4,5']bipyrimidinyl-6-yl)-4-hydroxymethyl-oxazolidin-2-one

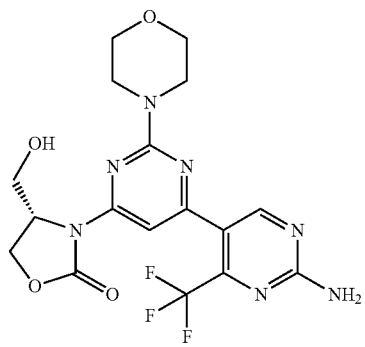 [SMILES: Nc1ncc(-c2cc(N3C(=O)OC[C@@H]3CO)nc(N3CCOCC3)n2)c(C(F)(F)F)n1]

A solution of product from step 7.1 (200 mg, 0.35 mmol), intermediate B (131 mg, 0.39 mmol), Na₂CO₃(2M, 526 µL, 1.05 mmol) and palladium tetrakis (24 mg, 0.21 mmol) in DME (4 mL) under argon was stirred at 80° C. for 2 h. The reaction mixture was treated with Na₂SO₄, diluted in EtOAc and the insoluble parts were filtered off. The filter cake was washed three times with EtOAc and the filtrate was evaporated. Then the residue was dissolved in THF and TBAF solution (1N, 351 µL, 0.35 mmol) was added. The mixture was stirred 1 h at RT. The solvent was removed and the residue was purified by flash chromatography (DCM/EtOH: 99:1→95:5) to give the title compound. $t_R$: 0.74 min (LC-MS 1).

Step 7.1: (R)-4-(tert-Butyl-diphenyl-silanyloxymethyl)-3-(6-chloro-2-morpholin-4-yl-pyrimidin-4-yl)-oxazolidin-2-one

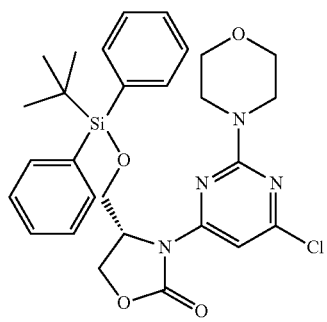 [SMILES: CC(C)(C)[Si](OC[C@H]1COC(=O)N1c1cc(Cl)nc(N2CCOCC2)n1)(c1ccccc1)c1ccccc1]

The title compound was prepared in analogy to the procedure described for step 2.2, but using product from step 7.2. The reaction was performed at 100° C. for 3 h. The reaction mixture was filtered and the filtrate was concentrated. The residue was purified by flash chromatography (hexane/EtOAc: 9:1→6:4) to give the title compound. $t_R$: 1.53 min (LC-MS 1); ESI-MS: 553.4/555.5 [M+H]$^+$ (LC-MS 1).

Step 7.2: (R)-4-(tert-Butyl-diphenyl-silanyloxymethyl)-oxazolidin-2-one

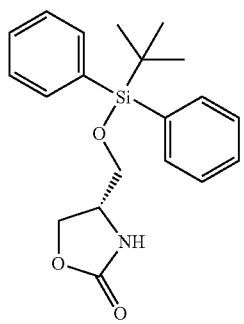 [SMILES: CC(C)(C)[Si](OC[C@H]1COC(=O)N1)(c1ccccc1)c1ccccc1]

The title compound was prepared in analogy to the procedure described for step 6.4, but using (S)-4-(hydroxymethyl) oxazolidin-2-one (SpeedChemical Corp. Shanghai), and DCM instead of DMF. The reaction was performed at RT for 16 h. The reaction mixture was diluted with water and extracted twice with Et$_2$O. The organic layers were combined, washed with water and brine, dried over Na$_2$SO$_4$, filtered and evaporated. The residue was purified by flash chromatography (hexane/EtOAc: 98:2→4:6). The residue was treated with hexane and Et$_2$O. The crystals obtained were filtered off to give the title compound. $t_R$: 1.26 min (LC-MS 1), $^1$H NMR (400 MHz, <dmso>) 5 ppm 0.98 (s, 9H) 3.51-3.63 (m, 2H) 3.88 (dd, J=8.60, 4.30 Hz, 1H) 4.14 (dd, J=8.60, 4.69 Hz, 1H) 4.30-4.38 (m, 1H) 7.37-7.50 (m, 6H) 7.57-7.65 (m, 4H) 7.71 (s, 1H).

Example 8

(4S,5R)-3-42'-Amino-2-(D8-morpholin-4-yl)-4'-trifluoromethyl-[4,5']bipyrimidinyl-6-yl)-4-hydroxymethyl-5-methyl-oxazolidin-2-one

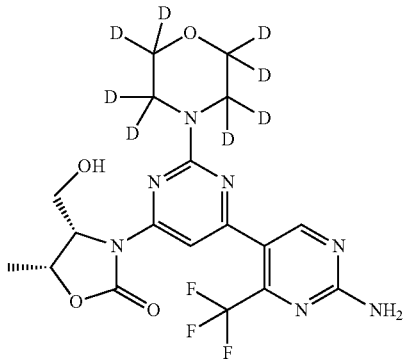 [SMILES: [2H]C1([2H])OC([2H])([2H])C([2H])([2H])N(c2nc(-c3cnc(N)nc3C(F)(F)F)cc(N3C(=O)O[C@H](C)[C@@H]3CO)n2)C1([2H])[2H]]

The title compound was prepared in analogy to the entire sequence described for example 6, but using product from step 8.1 instead of intermediate A and D-allo-Threoninol instead of D-threoninol. $t_R$: 0.79 min (LC-MS 1); ESI-MS: 464.5 [M+H]$^+$ (LC-MS 1).

Step 8.1:
4(4,6-Dichloro-pyrimidin-2-yl)-D8-morpholine

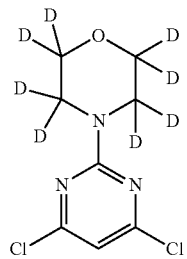 [SMILES: [2H]C1([2H])OC([2H])([2H])C([2H])([2H])N(c2nc(Cl)cc(Cl)n2)C1([2H])[2H]]

The 2,4,6-trichloropyrimidine was dissolved in EtOH with Et$_3$N and D8-morpholine. The reaction mixture was stirred at RT for 1 H. It was then diluted with saturated NaHCO$_3$ solution and extracted twice with EtOAc. The organic extracts were combined and washed with brine. Then it was dried over Na$_2$SO$_4$, filtered and concentrated. The residue was purified by flash chromatography (hexane/EtOAc: 0% hexane→40%). $t_R$: 0.94 min (LC-MS 1); ESI-MS: 242.3/244.2 [M+H]$^+$ (LC-MS 1).

Example 9

(S)-3-(2'-Amino-2-morpholin-4-yl-4'-trifluoromethyl-[4,5']bipyrimidinyl-6-yl)-4-(2-hydroxy-ethyl)-oxazolidin-2-one

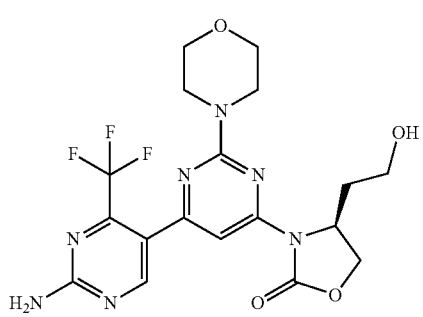 [SMILES: Nc1ncc(-c2cc(N3C(=O)OC[C@@H]3CCO)nc(N3CCOCC3)n2)c(C(F)(F)F)n1]

The title compound was prepared in analogy to the procedure described for example 6 but using product from step 9.1. The extraction was performed in DCM. The residue was purified by preparative HPLC (H₂O/ACN) then by flash chromatography (DCM/MeOH, 100:0→95:5). $t_R$: 0.78 min (LC-MS 1); ESI-MS: 456.2 [M+H]⁺ (LC-MS 1).

Step 9.1: (S)-3-(2'-Amino-2-morpholin-4-yl-4'-trifluoromethyl-[4,5']bipyrimidinyl-6-yl)-4-(tert-butyl-diphenyl-silanyloxymethyl)-[1,3]oxazinan-2-one

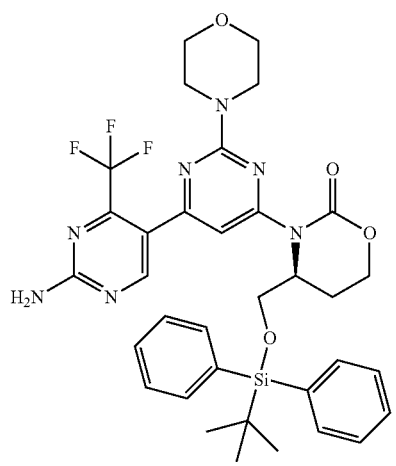 [SMILES: CC(C)(C)[Si](OC[C@@H]1CCOC(=O)N1c1cc(-c2cnc(N)nc2C(F)(F)F)nc(N2CCOCC2)n1)(c1ccccc1)c1ccccc1]

The title compound was prepared in analogy to the procedure described for example 1 but using product from step 9.2. The reaction was performed at 120° C. for 15 min. The reaction mixture was dissolved in DCM and extracted with H₂O. The organic layer was dried (Na₂SO₄), filtered and concentrated. The residue was purified by flash chromatography (heptane/EtOAc, 8:2→4:6). $t_R$: 1.54 min (LC-MS 1); ESI-MS: 694.3 [M+H]⁺ (LC-MS 1).

Step 9.2: (S)-4-(tert-Butyl-diphenyl-silanyloxymethyl)-3-(6-chloro-2-morpholin-4-yl-pyrimidin-4-yl)-[1,3]oxazinan-2-one

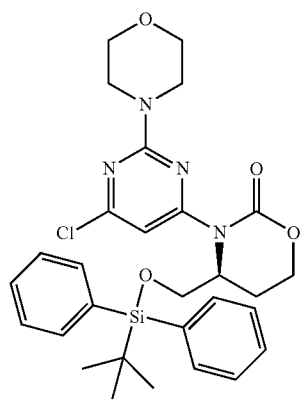 [SMILES: CC(C)(C)[Si](OC[C@@H]1CCOC(=O)N1c1cc(Cl)nc(N2CCOCC2)n1)(c1ccccc1)c1ccccc1]

The title compound was prepared in analogy to the procedure described for step 2.2 but using product from step 9.3. The reaction was performed at 115° C. for 2.5 h. The mixture was concentrated. The residue was purified by preparative HPLC (H₂O/ACN), then by flash chromatography (heptane/EtOAc, 9:1→0:100). $t_R$: 1.49 min (LC-MS 1); ESI-MS: 567.3 [M+H]⁺ (LC-MS 1).

Step 9.3: (S)-4-(tert-Butyl-diphenyl-silanyloxymethyl)-[1,3]oxazinan-2-one

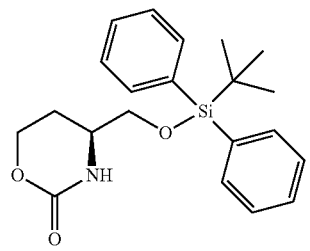 [SMILES: CC(C)(C)[Si](OC[C@@H]1CCOC(=O)N1)(c1ccccc1)c1ccccc1]

To a solution of the product from step 9.4 (900 mg, 2.03 mmol) in THF (40 mL) under argon was added NaH 60% in oil (160 mg, 4.0 mmol) and the mixture was stirred at rt for 4 h. The mixture was diluted with EtOAc and extracted with H₂O. The organic layer was dried (Na₂SO₄), filtered and concentrated. The residue was purified by flash chromatography (heptane/EtOAc, 100:0→0:100). $t_R$: 1.23 min (LC-MS 1); ESI-MS: 370.2 [M+H]⁺ (LC-MS 1).

Step 9.4: [(S)-1-(tert-Butyl-diphenyl-silanyloxymethyl)-3-hydroxy-propyl]-carbamic acid tert-butyl ester

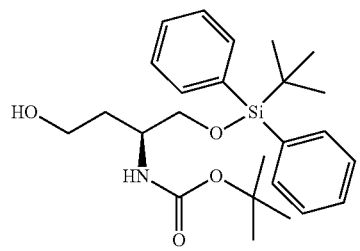 [SMILES: CC(C)(C)OC(=O)N[C@@H](CCO)CO[Si](c1ccccc1)(c1ccccc1)C(C)(C)C]

To a solution of the product from step 9.5 (40 g, 73 mmol) in TBME (400 mL) at 0° C. was added dropwise LiBH₄ (2M in THF, 74 mL, 146 mmol) and the mixture was stirred at 0° C. for 10 min then warmed up at rt and stirred for 5 h. The reaction mixture was quenched with H₂O then with 0.5M citric acid solution. The mixture was extracted with TBME. The organic layer was dried (MgSO₄), filtered and concentrated. The product was used without further purification.

Step 9.5: (S)-3-tert-Butoxycarbonylamino-4-(tert-butyl-diphenyl-silanyloxy)-butyric acid benzyl ester

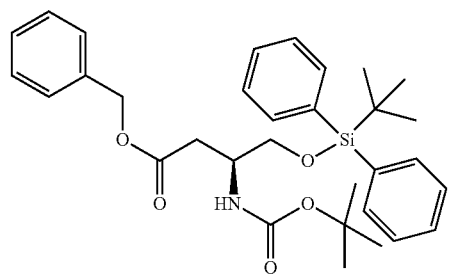 [SMILES: CC(C)(C)OC(=O)N[C@H](CO[Si](c1ccccc1)(c1ccccc1)C(C)(C)C)CC(=O)OCc1ccccc1]

The title product was prepared in analogy to the procedure described for step 6.4. $R_f$: 0.7 (hexane/EtOAc, 8:2)

Step 9.6:
(S)-3-tert-Butoxycarbonylamino-4-hydroxy-butyric acid benzyl ester

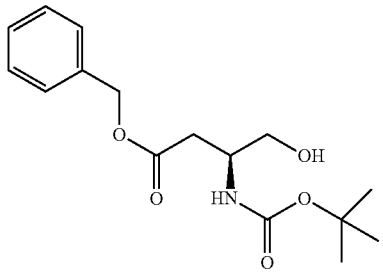 [SMILES: CC(C)(C)OC(=O)N[C@H](CO)CC(=O)OCc1ccccc1]

To a solution of Boc-L-aspartic acid-4-benzyl ester (100 g, 309 mmol) in DME (1.8 L) at −20° C. was added NMM (34 mL, 309 mmol) then dropwise iso-butylchloroformate (40 mL, 309 mmol) and the mixture was stirred at −20° C. for 20 min. The reaction mixture was filtered and the filtrate was cooled to −20° C. NaBH$_4$ (17.5 g, 463 mmol) was added portionwise at −20° C. The mixture was allowed to warm and stirred at rt for 1 h. The mixture was quenched with a 20% citric acid solution and then extracted with AcOEt. The organic layer was washed with NaHCO$_3$ solution, H$_2$O and brine, dried (MgSO$_4$), filtered and concentrated. The product was used without further purification for the next step.

Example 10

(4S,5R)-3-[2'-Amino-2-((S)-3-methyl-morpholin-4-yl)-4'-trifluoromethyl-[4,5']bipyrimidinyl-6-yl]-4-hydroxymethyl-5-methyl-oxazolidin-2-one

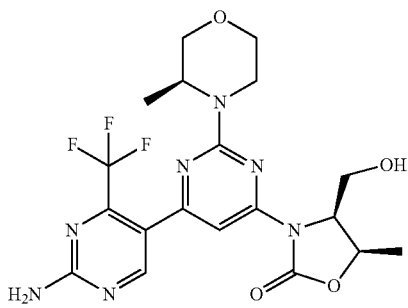 [SMILES: C[C@H]1OC(=O)N(c2cc(-c3cnc(N)nc3C(F)(F)F)nc(N3CCOC[C@@H]3C)n2)[C@H]1CO]

The title compound was prepared in analogy to the entire sequence described for example 6, but using product from step 10.1 instead of intermediate A and D-allo-Threoninol instead of D-threoninol. The mixture was dropwise added to a saturated solution of Na$_2$CO$_3$. After the addition, a saturated solution of NaHCO$_3$ was added (the final pH was around 7-8. It was diluted with water and extracted with EtOAc. The organic phase was washed with brine, dried over Na$_2$SO$_4$, filtered and evaporated. The residue was purified by preparative HPLC (Waters Sun Fire C18, 30×100 mm, 5 um; 0.1% TFA-water/acetonitrile; gradient acetonitrile 5-100% in 20 min). The residue was recrystalised in Et2O/hexane (3/1). The crystals were filtered off and washed with hexane to give the title compound. t$_R$: 2.89 min (HPLC 1); ESI-MS: 470.3 [M+H]$^+$ (LC-MS 1); m.p. 217.7° C. (onset).

Step 10.1: (S)-4-(4,6-Dichloro-pyrimidin-2-yl)-3-methyl-morpholine

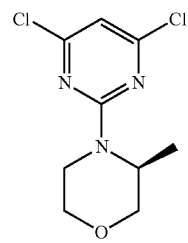

The 2,4,6-trichloropyrimidine (100 mg, 053 mmol) was dissolved in dioxane (2 mL) with DIPEA (280 μL, 1.6 mmol) and (S)-3-methylmorpholine (54 mg, 0.53 mmol). The reaction mixture was heated at 130° C. under microwave irradiations for 15 min. It was then diluted with EtOAc and washed with brine. The organic layer was dried over Na2SO4, filtered and concentrated. The residue was purified by preparative HPLC (Waters Sun Fire C18, 30×100 mm, 5 um; 0.1% TFA-water/acetonitrile; gradient acetonitrile 5-100% in 20 min) to afford the title compound (45 mg, 34%). t$_R$: 3.70 min (HPLC 1); ESI-MS: 248.2/250.2 [M+H]$^+$ (LC-MS 1).

Example 11

(For Comparison Purposes) 3-(2'-Amino-2-morpholin-4-yl-4'-trifluoromethyl-[4,5']bipyrimidinyl-6-yl)-oxazolidin-2-one

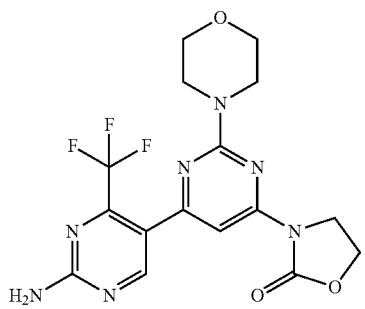 [SMILES: Nc1ncc(-c2cc(N3CCOC3=O)nc(N3CCOCC3)n2)c(C(F)(F)F)n1]

The title compound was prepared in analogy to example 5 (including step 5.1) but using the product from step 11.1. The reaction was performed at 100° C. for 1 h. The extraction was performed in EtOAc. The residue was purified by flash chromatography (heptane/EtOAc, 100:0→0:100). t$_R$: 0.87 min (LC-MS 1); ESI-MS: 412.4 [M+H]$^+$ (LC-MS 1).

Step 11.1: 3-(6-Chloro-2-morpholin-4-yl-pyrimidin-4-yl)-oxazolidin-2-one

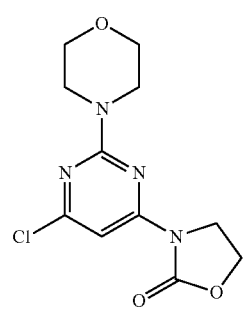 [SMILES: O=C1OCCN1c1cc(Cl)nc(N2CCOCC2)n1]

The title compound was prepared in analogy to the entire sequence described for step 2.2 but using oxazolidin-2-one. $t_R$: 0.93 min (LC-MS 1); ESI-MS: 285.5/287.4 [M+H]$^+$ (LC-MS 1).

Example 12

Formic acid (4S,5R)-3-(2'-amino-2-morpholin-4-yl-4'-trifluoromethyl-[4,5']bipyrimidinyl-6-yl)-5-methyl-2-oxo-oxazolidin-4-ylmethyl ester

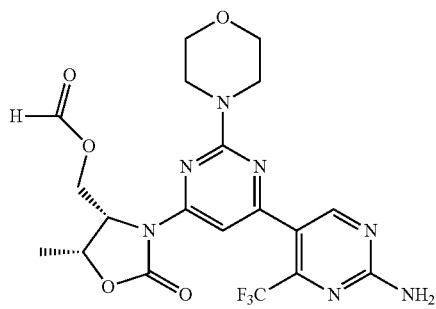 [SMILES: C[C@H]1OC(=O)N(c2cc(-c3cnc(N)nc3C(F)(F)F)nc(N3CCOCC3)n2)[C@H]1COC=O]

The compound of example 18 (47 mg, 0.10 mmol) was dissolved in formic acid (80 μL, 2.09 mmol) and stored at 5° C. for 4 days. It was then allowed to warm up to RT and it was stored for 2 days. It was then taken up with EtOAc and washed saturated NaHCO$_3$ solution and brine. The organic layer was dried over Na$_2$SO$_4$, filtered and concentrated. The residue was purified by preparative HPLC (Waters Sun Fire C18, 30×100 mm, 5 um; 0.1% TFA-water/acetonitrile; gradient acetonitrile 5-70% in 20 min) to afford the title compound (57 mg, 80%). $t_R$: 0.88 min (LC-MS 1); ESI-MS: 484.4 [M+H]$^+$ (LC-MS 1).

Example 13

(S)-3-[2'-Amino-2-((S)-3-methyl-morpholin-4-yl)-4'-trifluoromethyl-[4,5']bipyrimidinyl-6-yl]-4-methyl-oxazolidin-2-one

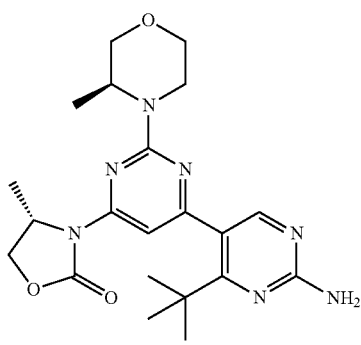 [SMILES: C[C@H]1COCCN1c1nc(-c2cnc(N)nc2C(C)(C)C)cc(N2C(=O)OC[C@@H]2C)n1]

The title compound was prepared in analogy to the entire sequence described for example 11, but using product from step 10.1 instead of intermediate A and (S)-4-methyl-2-oxazolidinone instead of oxazolidin-2-one. The residue was purified by flash chromatography (DCM/EtOH: 99.8/0.2→98/2) and then by preparative HPLC (Waters Sun Fire C18, 30×100 mm, 5 um; 0.1% TFA-water/acetonitrile; gradient acetonitrile 5-100% in 20 min) to afford the title compound (35 mg, 32%). $t_R$: 0.98 min (LC-MS 1); ESI-MS: 440.1 [M+H]$^+$ (LC-MS 1).

Example 14

(S)-3-(2'-Amino-2-morpholin-4-yl-4'-trifluoromethyl-[4,5']bipyrimidinyl-6-yl)-5-hydroxymethyl-oxazolidin-2-one

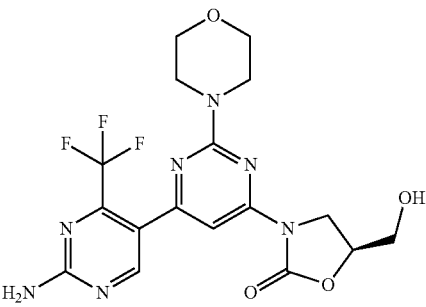 [SMILES: Nc1ncc(-c2cc(N3C[C@@H](CO)OC3=O)nc(N3CCOCC3)n2)c(C(F)(F)F)n1]

The title compound was prepared in analogy to the procedure described for example 6 but using the product from step 14.1. The residue was purified by flash chromatography (DCM/MeOH, 100:0→95:5). $t_R$: 0.77 min (LC-MS 1); ESI-MS: 442.2 [M+H]$^+$ (LC-MS 1).

Step 14.1: (S)-3-(2'-Amino-2-morpholin-4-yl-4'-trifluoromethyl-[4,5']bipyrimidinyl-6-yl)-5-(tert-butyl-diphenyl-silanyloxymethyl)-oxazolidin-2-one

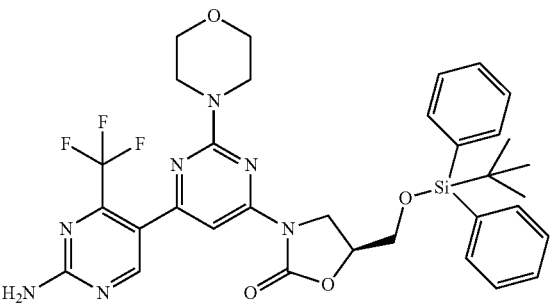 [SMILES: CC(C)(C)[Si](OC[C@@H]1CN(c2cc(-c3cnc(N)nc3C(F)(F)F)nc(N3CCOCC3)n2)C(=O)O1)(c1ccccc1)c1ccccc1]

The title compound was prepared in analogy to the procedure described for example 5 but using the product from step 14.2. The reaction was performed at 100° C. in an oil bath for 1 h. The extraction was performed in EtOAc. The residue was purified by flash chromatography (heptane/EtOAc, 100:0→0:100). $t_R$: 1.40 min (LC-MS 1); ESI-MS: 680.3 [M+H]$^+$ (LC-MS 1).

Step 14.2: (S)-5-(tert-Butyl-diphenyl-silanyloxymethyl)-3-(6-chloro-2-morpholin-4-yl-pyrimidin-4-yl)-oxazolidin-2-one

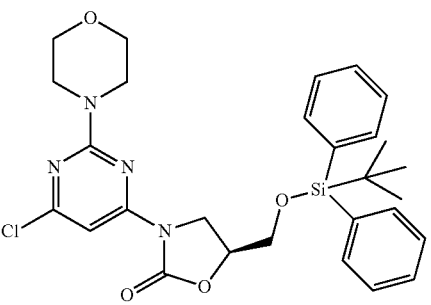 [SMILES: CC(C)(C)[Si](OC[C@@H]1CN(c2cc(Cl)nc(N3CCOCC3)n2)C(=O)O1)(c1ccccc1)c1ccccc1]

The title compound was prepared in analogy to the procedure described for step 2.2 but using the product from step 14.3. After extraction, the residue was purified by flash chromatography (heptane/EtOAc, 100:0→40:60). $t_R$: 1.49 min (LC-MS 1); ESI-MS: 553.3 [M+H]$^+$ (LC-MS 1).

Step 14.3: (S)-5-(tert-Butyl-diphenyl-silanyloxymethyl)-oxazolidin-2-one

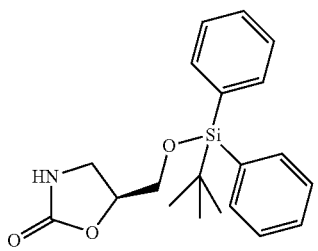 [SMILES: CC(C)(C)[Si](OC[C@@H]1CNC(=O)O1)(c1ccccc1)c1ccccc1]

To a solution of the product from step 14.4 (2.72 g, 8.27 mmol) and Et$_3$N (2.88 mL, 20.67 mmol) in DCM under argon was added dropwise triphosgene (982 mg, 3.31 mmol) and the mixture was stirred at rt for 5 h. The reaction mixture was quenched with a NH$_4$Cl solution. The organic layer was dried (Na$_2$SO$_4$), filtered and concentrated. The residue was purified by flash chromatography (heptane/EtOAc, 100:0→0:100). $t_R$: 1.21 min (LC-MS 1); ESI-MS: 373.2 [M+H]$^+$ (LC-MS 1).

Step 14.4: (S)-1-Amino-3-(tert-butyl-diphenyl-silanyloxy)-propan-2-ol

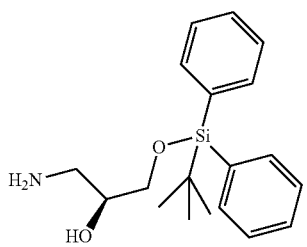 [SMILES: CC(C)(C)[Si](OC[C@@H](O)CN)(c1ccccc1)c1ccccc1]

The title compound was prepared in analogy to the procedure described for step 6.4 but using (S)-3-aminopropane-1,2-diol and using Et$_3$N instead of imidazole. After extraction, the residue was purified by flash chromatography (DCM/MeOH, 100:0→90/10). $t_R$: 0.93 min (LC-MS 1); ESI-MS: 330.2 [M+H]$^+$ (LC-MS 1).

Example 15

(4S,5R)-3-(2'-Amino-2-morpholin-4-yl-4'-trifluoromethyl-[4,5']bipyrimidinyl-6-yl)-5-hydroxymethyl-4-methyl-oxazolidin-2-one

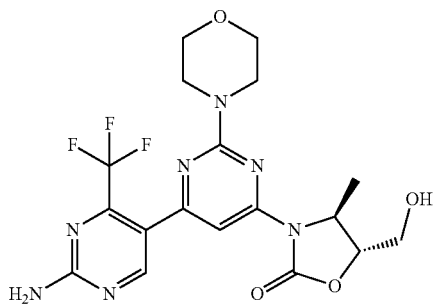 [SMILES: C[C@H]1[C@H](CO)OC(=O)N1c1cc(-c2cnc(N)nc2C(F)(F)F)nc(N2CCOCC2)n1]

The title compound was prepared in analogy to the entire sequence described for example 6, but using product from step 15.1 instead of D-threoninol. $t_R$: 0.98 min (LC-MS 1); ESI-MS: 344.3 [M+H]$^+$ (LC-MS 1).

Step 15.1: (2R,3S)-3-Amino-butane-1,2-diol

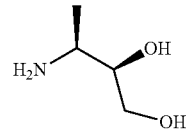

The title compound was prepared in analogy to the procedure of step 19.1, but using product from step 15.2. The residue was purified by flash chromatography (DCM/EtOH: 99.8/0.2→98/2) and then by preparative HPLC (Waters Sun Fire C18, 30×100 mm, 5 um; 0.1% TFA-water/acetonitrile; gradient acetonitrile 5-100% in 20 min) to afford the title compound (35 mg, 32%). $t_R$: 0.98 min (LC-MS 1); ESI-MS: 440.1 [M+H]$^+$ (LC-MS 1).

Step 15.2: N-Benzyl-N—[(S)-1-((R)-2,2-dimethyl-[1,3]dioxolan-4-yl)-ethyl]-hydroxylamine

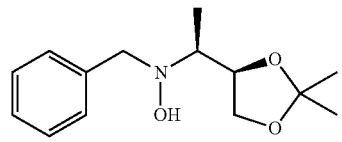 [SMILES: C[C@@H]([C@@H]1COC(C)(C)O1)N(O)Cc1ccccc1]

The title compound is the second isomer formed during the step 19.2 (1.07 g, 57%). $t_R$: 0.91 min (LC-MS 1); ESI-MS: 252.2 [M+H]$^+$ (LC-MS 1).

Example 16

(S)-3-(2'-Amino-2-morpholin-4-yl-4'-trifluoromethyl-[4,5']bipyrimidinyl-6-yl)-5-methyl-oxazolidin-2-one

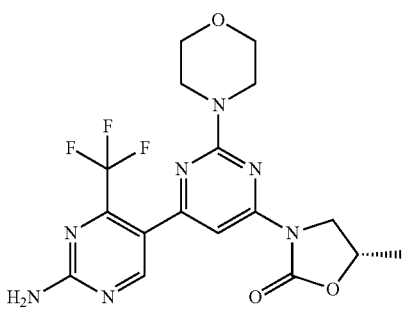 [SMILES: C[C@H]1CN(c2cc(-c3cnc(N)nc3C(F)(F)F)nc(N3CCOCC3)n2)C(=O)O1]

The title compound was prepared in analogy to example 11, but using product from step 16.1 instead of (R)-4-methyl-2-oxazolidinone. The reaction was performed at 100° C. for 1 H. The reaction mixture was taken up with EtOAc. It was washed twice with saturated NaHCO$_3$ solution and once with brine. The organic layer dried over sodium sulfate. The residue was purified by flash chromatography (heptane/EtOAc: 0%→85% EtOAc) to give the title compound (9.6 mg, 58%). $t_R$: 0.94 min (LC-MS 1); ESI-MS: 426.2 [M+H]$^+$ (LC-MS 1).

Step 16.1: (S)-5-Methyl-oxazolidin-2-one

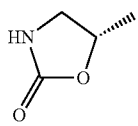

The title compound was prepared in analogy to the procedure described for step 6.3, but using (S)-1-aminopropan-2-ol. The reaction was performed at RT for 3 H. The reaction was quenched with saturated NH4Cl solution (10 mL) and stirred 10 min at RT. The water layer was separated and the organic layer washed with water. The combined aqueous layer were extracted 3× with DCM. The combined organic layer were dried over $Na_2SO_4$, filtered and concentrated. The residue was purified by flash chromatography (heptane/EtOAc: 0%→100% EtOAc) to give the title compound (38 mg, 9%). $^1$H NMR (400 MHz, <DMSO>) δ ppm 1.27 (d, J=6.25 Hz, 3H) 2.94-3.08 (m, 1H) 3.48-3.58 (m, 1H) 4.62 (m, 1H) 7.37 (br. s., 1H)

Example 17

(S)-3-(2'-amino-2-D8-morpholino-4'-(trifluoromethyl)-[4,5'-bipyrimidin]-6-yl)-4-methyloxazolidin-2-one

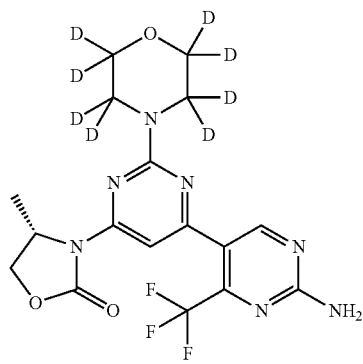 [SMILES: [2H]C1([2H])OC([2H])([2H])C([2H])([2H])N(c2nc(-c3cnc(N)nc3C(F)(F)F)cc(N3C(=O)OC[C@@H]3C)n2)C1([2H])[2H]]

The title compound was prepared in analogy to the procedure described for example 4 but using the product from step 17.1. After completion, the reaction mixture was filtered through celite and concentrated. The residue was purified by flash chromatography (DCM/EtOH, 99.5:0.5→98:2). The residue was triturated in DCM and washed with hexane to afford the title compound. $t_R$: 0.89 min (LC-MS 1); ESI-MS: 434.4 [M+H]$^+$ (LC-MS 1); $R_f$: 0.67 (DCM/EtOH, 95:5).

Step 17.1: (S)-3-(6-Chloro-2-D8-morpholin-4-yl-pyrimidin-4-yl)-4-methyl-oxazolidin-2-one

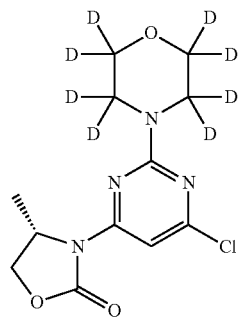 [SMILES: [2H]C1([2H])OC([2H])([2H])C([2H])([2H])N(c2nc(Cl)cc(N3C(=O)OC[C@@H]3C)n2)C1([2H])[2H]]

The title compound was prepared in analogy to the procedure described for step 2.2 but using the product from step 8.1 and (S)-4-methyl-2-oxazolidinone. The extraction was performed in DCM. The residue was purified by flash chromatography (heptane/EtOAc, 9:1→7:3). $t_R$: 0.97 min (LC-MS 1); ESI-MS: 307.3/309.3 [M+H]$^+$ (LC-MS 1).

Example 18

(4S,5R)-3-(2'-Amino-2-morpholin-4-yl-4'-trifluoromethyl-[4,5']bipyrimidinyl-6-yl)-4-hydroxymethyl-5-methyl-oxazolidin-2-one

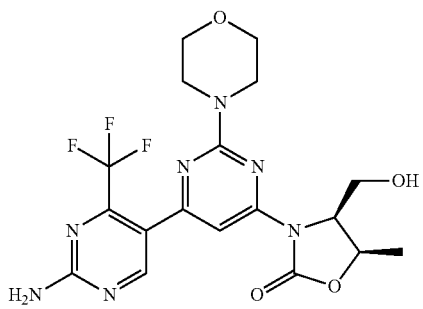 [SMILES: C[C@H]1OC(=O)N(c2cc(-c3cnc(N)nc3C(F)(F)F)nc(N3CCOCC3)n2)[C@H]1CO]

The title compound was prepared in analogy to the entire sequence described for example 6, but using D-allo-Threoninol instead of D-threoninol. The reaction was performed at RT for 33H. The mixture was dropwised added to a saturated solution of $Na_2CO_3$. After the addition, the pH was around 7-8. It was diluted with water and extracted with EtOAc. The organic phase was washed with brine, dried over $Na_2SO_4$, filtered and evaporated. The residue was purified by preparative HPLC (Waters Sun Fire C18, 30×100 mm, 5 um; 0.1% TFA-water/acetonitrile; gradient acetonitrile 5-60% in 20 min). The fractions were combined and basified with 5% $NaHCO_3$ solution. The product precipitated and was filtered off. To eliminate residual Palladium the product was dissolved in DCM/MeOH (4/1) and was passed through an SPE cartridge of MP-Thiol from polymerlabs and then the solvent was evaporated. A number of batches were produced based on this method, and several worked-up to provide crystalline material as follows.

Batch A:

For the preparation of this batch the product was not passed through an SPE cartridge of MP-Thiol from polymerlabs. The pure fractions obtained after the preparative HPLC were combined and treated with NaHCO3. The $CH_3CN$ was evaporated whereupon the product crystallized. The product was collected by filtration washed with water and dried to give the title compound as a white solid. m.p. 221.3° C. (onset).

Batch B:

For the preparation of this batch the product was not passed through an SPE cartridge of MP-Thiol from polymerlabs. The pure fractions obtained after the preparative HPLC were combined and treated with solid NaHCO3. The $CH_3CN$ was evaporated whereupon the product crystallized. The aqueous mixture was kept for 1 h in the refrigerator, filtered, washed with water and dried under HV overnight to afford a white solid, m=298 mg. m.p. 249.9° C. (onset)

Batch C:

For the preparation of this batch the product was not passed through an SPE cartridge of MP-Thiol from polymerlabs. The pure fractions obtained after the preparative HPLC were combined and evaporated. The residue was taken up in $CH_3CN$ and then water containing 0.1% TFA was added followed by solid $NaHCO_3$. The solution is concentrated and the precipitate is filtered, washed with water and dried to give the title product as a white solid. m.p. 237.9° C. (onset)

Batch D:

After the passage through the SPE cartridge of MP-Thiol from polymerlabs the solvent was evaporated. The residue was dissolved in $CH_3CN$ and then diluted with the same amount of water. The $CH_3CN$ was evaporated and just before crystallization of the product, some crystals of Batch B were added. $CH_3CN$ was then completely evaporated and the suspension was cooled in the fridge. It was then filtered, collected and dried under HV overnight to afford a the title product as a white solid, m.p. 259.0° C. (onset)

Batch E:

Same procedure as described for Batch C but some crystals of Batch D were added to induce crystallisation. The title product was obtained as a white solid, m.p. 258.8° C. (onset).

Example 19

(4S,5S)-3-(2'-Amino-2-morpholin-4-yl-4'-trifluoromethyl-[4,5']bipyrimidinyl-6-yl)-5-hydroxymethyl-4-methyl-oxazolidin-2-one

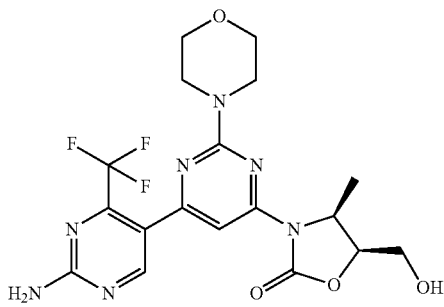 [SMILES: C[C@H]1[C@@H](CO)OC(=O)N1c1cc(-c2cnc(N)nc2C(F)(F)F)nc(N2CCOCC2)n1]

The title compound was prepared in analogy to the entire sequence described for example 6, but using product from step 19.1 instead of D-threoninol. The reaction was performed at RT for 16H 30. The mixture was dropwised added to a saturated solution of $Na_2CO_3$. After the addition, it was diluted with water and extracted twice with EtOAc. The organic phase was washed with brine, dried over $Na_2SO_4$, filtered and evaporated. The residue was purified by preparative HPLC (Waters Sun Fire C18, 30×100 mm, 5 um; 0.1% TFA-water/acetonitrile; gradient acetonitrile 5-80% in 20 min) to give the title compound (16.3 mg, 75%). $t_R$: 2.79 min (HPLC 1); ESI-MS: 456.1 $[M+H]^+$.

Step 19.1: (2S,3S)-3-Amino-butane-1,2-diol

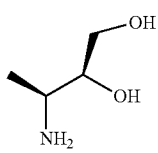

The product from step 19.2 was stirred in HCl in solution in EtOH for 2 H at RT. The solvent was removed to give the title compound as an HCl salt (303 mg, 100%). $^1$H NMR (400 MHz, <dmso>) δ ppm 1.08 (d, J=6.65 Hz, 3H) 3.18-3.33 (m, 1H) 3.33-3.45 (m, 1H) 3.61-3.72 (m, 1H) 7.85 (br. s., 2H)

Step 19.2: (S)-1-((S)-2,2-Dimethyl-[1,3]dioxolan-4-yl)-ethylamine

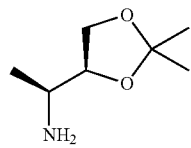

The product from step 19.3 (product 2, last eluting, 538 mg, 2.14 mmol) was dissolved in AcOH (25 mL) with Pd/C (100 mg) and the reaction mixture was stirred at RT for 11H under $H_2$ conditions. It was then filtered over Celite and then the solvent was removed to give the title compound (311 mg, 100%). NMR (400 MHz, <dmso>) δ ppm 0.90-1.04 (m, 3H) 1.16-1.38 (m, 6H) 2.76-2.90 (m, 1H) 3.75 (dd, J=13.86, 7.22 Hz, 2H) 3.90 (br. s., 1H); $t_R$: 3.13 min (HPLC 1).

Step 19.3: N-Benzyl-N—[(R)-1-((S)-2,2-dimethyl-[1,3]dioxolan-4-yl)-ethyl]-hydroxylamine and N-Benzyl-N—[(S)-1-((S)-2,2-dimethyl-[1,3]dioxolan-4-yl)-ethyl]-hydroxylamine Product 1

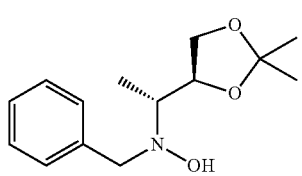

Product 2

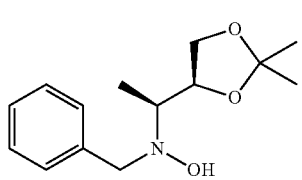

To a well stirred solution of 1.48 g (6.29 mmol) of the product from step 19.4 in 80 ml $Et_2O$ was added 6.29 ml (6.29 mmol) 1M $Et_2AlCl$ in hexanes in one portion and stirring was continued for 15 min. The mixture was then cooled to −60° C. and treated with 6.29 ml (18.87 mmol) 3M Methylmagnesium bromide in $Et_2O$. The mixture was stirred for 2 h at −60° C. and then allowed to slowly warm up to RT under stirring during the night. After that, the reaction was treated with NaOH (2M, 40 ml). After stirring for 15 min at RT, the mixture was extracted 3×120 with $Et_2O$. The combined organic layers were dried over $Na_2SO_4$, filtered and concentrated under vacuum. The residue is dissolved in MeOH and purified by reverse phase prep. HPLC in 8 injections ($H_2O$[+ 0.1% TFA]/$CH_3CN$ 97:3 to 50:50 in 20 min.):

Fractions 1-3 were collected together and basified with ~2 g NaHCO$_3$, before being concentrated. The resulting layer was extracted with 2×150 ml Et$_2$O and the combined organic layers were dried over Na2SO4, filtered and evaporated to dryness to give 1.01 g of a colorless oil, which slowly crystallizes (~99% pure by 1HNMR; HPLC Rt=2.36; ESI-MS: 252.2 [M+H]$^+$ (LC-MS 1))→Product 1

Fractions 5-7 were collected together and basified with ~2 g NaHCO$_3$, before being concentrated. The resulting suspension was extracted with 2×150 ml Et$_2$O and the combined organic layers are dried over Na$_2$SO$_4$, filtered and evaporated to dryness to give 363 mg of a white solid (~99% pure by 1 HNMR; HPLC Rt=2.44; ESI-MS: 252.3 [M+H]+(LC-MS 1))→Product 2.

Step 19.4: (S,Z)-N-((2,2-dimethyl-1,3-dioxolan-4-yl)methylene)-1-phenylmethanamine oxide

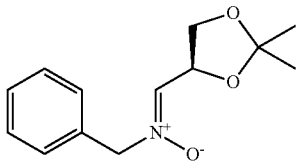 [SMILES: CC1(C)OC[C@H](/C=[N+](\[O-])Cc2ccccc2)O1]

1.50 g (11.53 mmol) (R)-2,2-Dimethyl-1.3-dioxolane-4-carboxaldehyde (Fluorochem, Hadfield, UK) was dissolved in 60 ml of DCM and treated with 1.64 g (11.53 mmol) sodium sulfate. The reaction mixture was flushed with argon and treated with a solution of 1.42 g (11.53 mmol) N-benzylhydroxylamine (prepared from the commercially available hydrochloride salt) in 20 ml of CH2Cl2. The reaction mixture was stirred under argon at RT for 16.5 h and then filtered. Silicagel was added to the filtrate is and preabsorbed, before being purified by chromatography on silicagel (gradient: Heptane/EtOAc 0%-100% in 30 min). Fr. 20-80 were collected and evaporated to dryness and dried under vacuum overnight to give 1.48 g of a white solid (~100% pure by HPLC, Rt=1.43); ESI-MS: 236.2 [M+H]+(LC-MS 1))

Example 20

(R)-3-(2'-Amino-2-morpholin-4-yl-4'-trifluoromethyl-[4,5']bipyrimidinyl-6-yl)-5-hydroxymethyl-oxazolidin-2-one

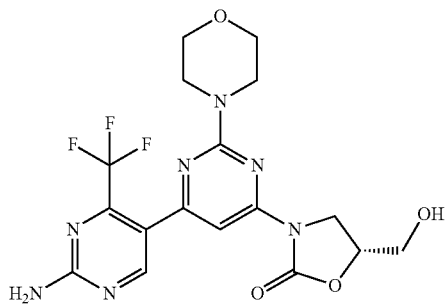 [SMILES: Nc1ncc(-c2cc(N3C[C@H](CO)OC3=O)nc(N3CCOCC3)n2)c(C(F)(F)F)n1]

The title compound was prepared in analogy to the entire sequence described for example 6, but using (R)-3-aminopropane-1,2-diol instead of D-threoninol. The reaction was performed at RT for 16H. Then the reaction mixture was quenched carefully with NaHCO$_3$. Then it was diluted with EtOAc and washed twice with saturated NaHCO3 solution and once with brine. The organic layer was dried over Na$_2$SO$_4$, filtered and evaporated. The residue was purified by flash chromatography (DCM/EtOH: 0%→10% MeOH) to give the title compound (22.8 mg, 38%). $t_R$: 0.77 min (HPLC 1); ESI-MS: 442.2 [M+H]$^+$ (LC-MS 1).

Example 21

(3aR,6aR)-3-(2'-amino-2-morpholino-4'-(trifluoromethyl)-[4,5'-bipyrimidin]-6-yl)-tetrahydrofuro[3,4-d]oxazol-2(3H)-one

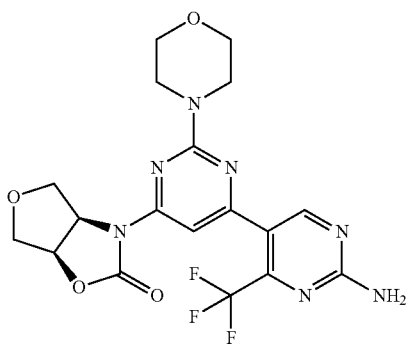 [SMILES: Nc1ncc(-c2cc(N3C(=O)O[C@H]4COC[C@H]43)nc(N3CCOCC3)n2)c(C(F)(F)F)n1]

A solution (3aR,6aR)-3-(6-chloro-2-morpholinopyrimidin-4-yl)tetrahydrofuro[3,4-d]oxazol-2(3H)-one (100 mg, 0.306 mmol), intermediate B (115 mg, 0.398 mmol), K$_3$PO$_4$ (195 mg, 0.918 mmol) and PdCl$_2$(dppf)-CH$_2$Cl$_2$ (25 mg, 0.031 mmol) in DME/H$_2$O (2.2 mL) under argon was stirred at 80° C. for 1.5 h. The mixture was diluted in EtOAc and extracted with saturated NaHCO$_3$. The organic layer was washed with H$_2$O and brine, dried over MgSO$_4$, filtered and concentrated. The residue was purified by flash chromatography (hexane-EtOAc 70:30→0:100) to afford the title compound as a colorless solid (88 mg, 62%): $t_R$=0.84 min (LC-MS 3); ESI-MS: 454 [M+H]$^+$ (LC-MS 3).

Step 21.1: (3aR,6aR)-3-(6-Chloro-2-morpholinopyrimidin-4-yl)tetrahydrofuro[3,4-d]oxazol-2(3H)-one

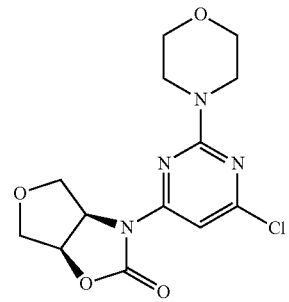 [SMILES: O=C1O[C@H]2COC[C@H]2N1c1cc(Cl)nc(N2CCOCC2)n1]

To a solution of (3aR,6aR)-tetrahydrofuro[3,4-d]oxazol-2(3H)-one (500 mg, 3.87 mmol), 4-(4,6-dichloropyrimidin-2-yl)morpholine (1088 mg, 4.65 mmol) and Cs$_2$CO$_3$ (2.14 g, 6.58 mmol) in dioxane (20 mL) was added after degassing with argon 4,5-bis(diphenylphosphino)-9,9-dimethylxanthene (157 mg, 0.271 mmol) and Pd$_2$(dba)$_3$ (70.9 mg, 0.077 mmol) and the reaction mixture was heated for 6 h at 85° C. The reaction mixture was added to 10% aqueous NaHCO$_3$ solution and extracted with EtOAc. Combined extracts were washed with brine, dried over MgSO4, filtered and concentrated. The crude product was triturated in MeOH overnight, filtered off and dried to afford the title compound as a colorless solid (1.12 g, 87%): t$_R$=0.92 min (LC-MS 3); ESI-MS: 327, 329 [M+H]$^+$ (LC-MS 3).

Step 21.2:
(3aR,6aR)-Tetrahydrofuro[3,4-d]oxazol-2(3H)-one

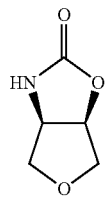

To a solution of (3R,4R)-4-aminotetrahydrofuran-3-ol (1.1 g, 7.88 mmol) and DIEA (4.54 ml, 26.0 mmol) in CH$_2$Cl$_2$ (30 mL) was added (bis(trichloromethyl) carbonate (1.75 g, 5.91 mmol) dissolved in CH$_2$Cl$_2$ (5 mL) at RT over a period of 30 min. After stirring for 0.5 h at 25° C., the reaction mixture was added to aqueous K$_2$CO$_3$ solution, stirred for 1 h and the CH$_2$Cl$_2$ was evaporated. The aqueous phase was washed with Et$_2$O and afterwards evaporated to dryness. The residue was triturated with EtOH/THF 1:1, the inorganic salts removed by filtration through a plug of silica gel, and the filtrate was concentrated to provide the title compound as a beige solid (930 mg, 90%): ESI-MS: 147 [M+NH]$^+$.

Example 22

(3aR*,6R*,6aR*)-3-(2'-Amino-2-morpholino-4'-(trifluoromethyl)-[4,5'-bipyrimidin]-6-yl)-6-hydroxyhexahydro-2H-cyclopenta[d]oxazol-2-one

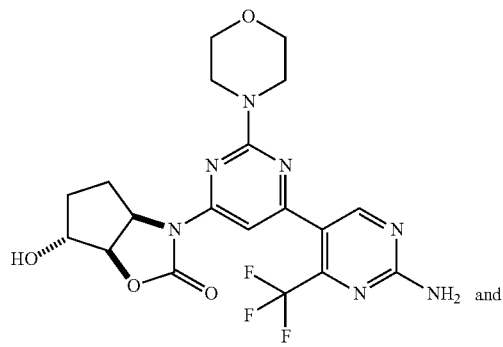

and

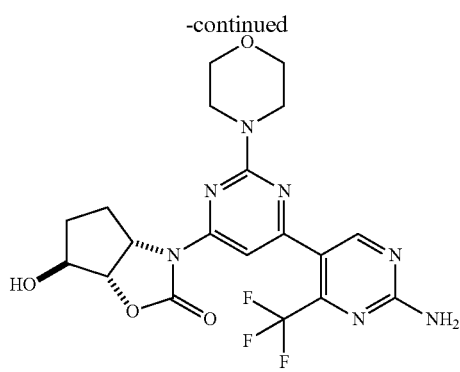

To a solution of (3aR*,6R*,6aR*)-3-(2'-amino-2-morpholino-4'-(trifluoromethyl)-[4,5'-bipyrimidin]-6-yl)-6-((tert-butyldimethylsilyl)oxy)hexahydro-2H-cyclopenta[d]oxazol-2-one (810 mg, 1.253 mmol) in THF (12 mL), was added dropwise 1M TBAF in THF (1.0 mL, 1.0 mmol) at 0° C. The reaction mixture was stirred for 30 min at 0° C. and 2 h at RT before evaporation. The residue was purified by flash chromatography (hexane-THF 60:40→0:100). The residue was triturated in Et$_2$O, filtered and dried. The residue was purified by preparative HPLC (Waters Sun Fire C18, 30×100 mm, 5 um; 0.1% TFA-water/acetonitrile; gradient acetonitrile 5-100% in 20 min) to afford the title compound (430 mg, 72%); t$_R$=0.93 min (UPLC 1), t$_R$=0.81 min (LC-MS 3); ESI-MS: 468 [M+H]$^+$ (LC-MS 3).

Step 22.1: (3aR*,6R*,6aR*)-3-(2'-Amino-2-morpholino-4'-(trifluoromethyl)-[4,5'-bipyrimidin]-6-yl)-6-((tert-butyldimethylsilyl)oxy)hexahydro-2H-cyclopenta[d]oxazol-2-one

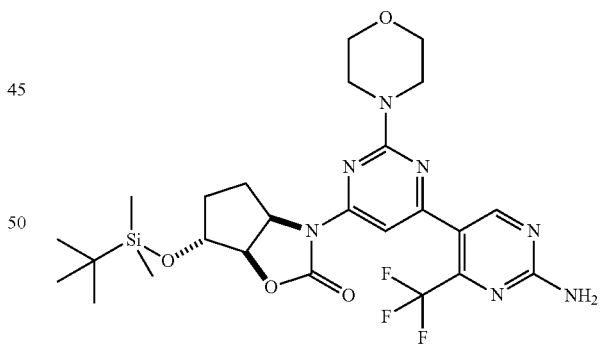

The title compound was prepared in analogy to the procedure described for example 21 from (3aR*,6R*,6aR*)-6-((tert-butyldimethylsilyl)oxy)-3-(6-chloro-2-morpholinopyrimidin-4-yl)hexa-hydro-2H-cyclopenta[d]oxazol-2-one and intermediate B and using Pd(PPh$_3$)$_4$ instead of PdCl$_2$(dppf)-CH$_2$Cl$_2$ and Na$_2$CO$_3$ instead of K$_3$PO$_4$ to afford the title compound after crystallization from EtOAc/hexane as white solid: t$_R$=1.62 min (UPLC 1), t$_R$=1.47 min (LC-MS 3); ESI-MS: 582 [M+H]$^+$ (LC-MS 3).

Step 22.2: (3aR*,6R*,6aR*)-6-((tert-butyldimethyl-silyl)oxy)-3-(6-chloro-2-morpholinopyrimidin-4-yl)hexahydro-2H-cyclopenta[d]oxazol-2-one

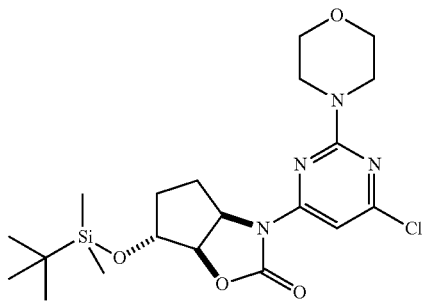

The title compound was prepared in analogy to the procedure described for step 21.1 from (3aR*,6R*,6aR*)-6-((tert-butyldimethylsilyl)oxy)hexahydro-2H-cyclopenta[d]oxazol-2-one and intermediate A: $t_R$=1.76 min (UPLC 1), $t_R$, 1.58 min (LC-MS 3); ESI-MS: 455, 457 [M+H]$^+$ (LC-MS 3).

Step 22.3: (3aR*,6R*,6aR*)-6-((tert-Butyldimethyl-silyl)oxy)hexahydro-2H-cyclopenta[d]oxazol-2-one

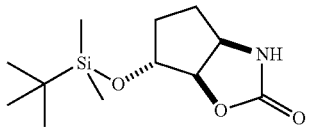

To a suspension of (3aR*,6R*,6aR*)-6-((tert-butyldimethylsilyl)oxy)-3-((2-nitrophenyl)sulfonyl)-hexahydro-2H-cyclopenta[d]oxazol-2-one (1.47 g, 3.32 mmol) and $Cs_2CO_3$ (2.164 g, 6.64 mmol) in DMF (25 mL) was added N-acetyl-L-cysteine (0.921 g, 5.65 mmol) and the reaction mixture was stirred for 16 h at RT. The reaction mixture was evaporated and the residue suspended in saturated NaHCO3 solution and extracted with EtOAc. Combined extracts were washed with brine, dried over MgSO4, filtered and concentrated. The title compound was obtained after purification by flash chromatography (heptane/EtOAc 90:10→50:50) as a yellow oil (0.84 g, 98%): TLC (heptane/EtOAc 1:1) $R_f$=0.28.

Step 22.4: (3aR*,6R*,6aR*)-6-((tert-Butyldimethyl-silyl)oxy)-3-((2-nitrophenyl)sulfonyl)hexahydro-2H-cyclopenta[d]oxazol-2-one

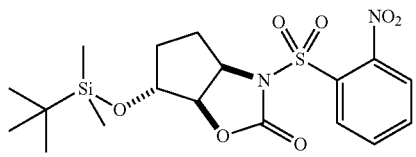

To a solution of (3aR*,6R*,6aR*)-6-hydroxy-3-((2-nitrophenyl)sulfonyl)hexahydro-2H-cyclo-penta[d]oxazol-2-one (1.2 g, 3.66 mmol) and 2,6-lutidine (0.851 mL, 7.31 mmol) in $CH_2Cl_2$ (25 mL) was added dropwise at 0° C. the tert-butyldimethylsilyl trifluoromethanesulfonate (1.091 mL, 4.75 mmol). The reaction mixture was stirred for 1 h at 0° C. followed by 2 h at RT. The reaction mixture was diluted with $CH_2Cl_2$ and washed with 20% aqueous $NaH_2PO_4$ solution and $H_2O$, dried over $MgSO_4$, filtered and concentrated. The title compound was obtained after crystallization from EtOAc/heptane as white solid (1.5 g, 88%): TLC (heptane/EtOAc 1:1) $R_f$=0.54; $t_R$=1.58 min (UPLC 1), $t_R$=1.43 min (LC-MS 3); ESI-MS: 460 [M+NH$_4$]$^+$ (LC-MS 3).

Step 22.5: (3aR*,6R*,6aR*)-6-Hydroxy-3-((2-nitro-phenyl)sulfonyl)hexahydro-2H-cyclopenta[d]-ox-azol-2-one

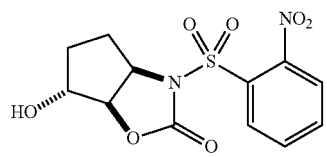

To a solution of tert-butyl (1R*,2S*,5S*)-6-oxabicyclo[3.1.0]hexan-2-yl((2-nitrophenyl)sulfonyl)-carbamate (2.0 g, 5.10 mmol) in MeOH (40 mL) was added Amberlyst 15 (4.0 g) and the resulting suspension was stirred for 1.5 h at 25° C. The reaction mixture was filtered and concentrated. The title compound was obtained after purification by flash chromatography (heptane-EtOAc 90:10→EtOAc) as a beige solid (1.24 g, 73%): TLC (heptane/EtOAc 1:2) $R_f$=0.36; $t_R$=0.80 min (UPLC 1), $t_R$, 0.77 min (LC-MS 3); ESI-MS: 346 [M+NH$_4$]$^+$ (LC-MS 3).

Step 22.6: (tert-Butyl (1R*,2S*,5S*)-6-oxabicyclo[3.1.0]hexan-2-yl((2-nitrophenyl)sulfonyl)-carbamate

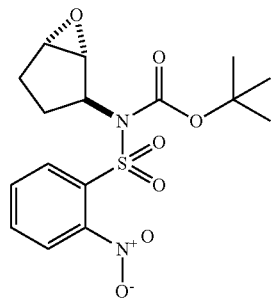

To a suspension of tert-butyl cyclopent-2-en-1-yl((2-nitrophenyl)sulfonyl)carbamate (2.75 g, 7.46 mmol) and NaHCO$_3$ (1.254 g, 14.93 mmol) in $CH_2Cl_2$ (60 mL) was added in one portion meta-chloroperoxybenzoic acid (2.58 g, 14.93 mmol). The resulting reaction mixture was stirred overnight at RT. The reaction mixture was diluted with $CH_2Cl_2$ and washed with 20% aqueous $Na_2SO_3$ solution, saturated NaHCO$_3$ solution and water. The organic phase was dried over $MgSO_4$ and concenrated. The title compound was obtained after crystallization from EtOAc as white crystals (2.01 g, 68%): TLC (heptane-EtOAc 1:1) $R_f$=0.48; $t_R$=1.20 min (UPLC 1), $t_R$=1.12 min (LC-MS 3); ESI-MS: 329 [M-isobutylene]$^+$ (LC-MS 3).

Step 22.7: (tert-butyl cyclopent-2-en-1-yl((2-nitrophenyl)sulfonyl)carbamate

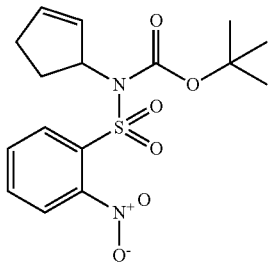

To a suspension of triphenylphosphine (3.09 g, 11.77 mmol), tert-butyl 2-nitrophenylsulfonyl-carbamate (3.40 g, 11.23 mmol) and cyclopent-2-enol (0.900 g, 10.70 mmol) in toluene (60 mL) was added dropwise at −20° C. the diethylazodicarboxylate (1.948 mL, 12.30 mmol). The reaction mixture was stirred at −20° C. for 2 h followed by 3 h at 0° C. The reaction mixture was concentrated and the title compound was obtained after purification by flash chromatography (heptane/EtOAc 95:5→3:1) as a white solid (2.79 g, 67%): $t_R$=1.34 min (UPLC 1), $t_R$, 1.24 min (LC-MS 3); ESI-MS: 386 M+NH$_4$]$^+$ (LC-MS 3).

Example 22A

First Eluting Enantiomer on Chiralpak AD of (3aR, 6R,6aR)- and (3aS,6S,6aS)-(2'-Amino-2-morpholino-4'-(trifluoromethyl)-[4,5'-bipyrimidin]-6-yl)-6-hydroxyhexahydro-2H-cyclopenta[d]oxazol-2-one Absolute stereochemistry not determined.

The title compound was obtained after preparative chiral HPLC separation of the racemic product of example 22. (Column: Chiralpak AD 20 μm 5×500 mm. Flow 70 mL/min. heptane/EtOH/DEA 20:80:0.01). $t_R$: 17.7 min (Column: Chiralpak AD-H, 4.6×250 mm. Flow 1.2 mL/min. heptane/EtOH 70:30).

Example 22B

Second Eluting Enantiomer on Chiralpak AD of (3aR,6R,6aR)- and (3aS,6S,6aS)-(2'-Amino-2-morpholino-4'-(trifluoromethyl)-[4,5'-bipyrimidin]-6-yl)-6-hydroxyhexahydro-2H-cyclopenta[d]oxazol-2-one Absolute stereochemistry not determined.

The title compound was obtained after preparative chiral HPLC separation of the racemic product of example 22. (Column: Chiralpak AD 20 μm 5×500 mm. Flow 70 mL/min. heptane/EtOH/DEA 20:80:0.01). $t_R$: 23.3 min (Column: Chiralpak AD-H, 4.6×250 mm. Flow 1.2 mL/min. heptane/EtOH 70:30).

Example 23

(4S,5R)-3-(2'-Amino-2-morpholino-4'-(trifluoromethyl)-[4,5'-bipyrimidin]-6-yl)-5-(2-hydroxyethyl)-4-methyloxazolidin-2-one

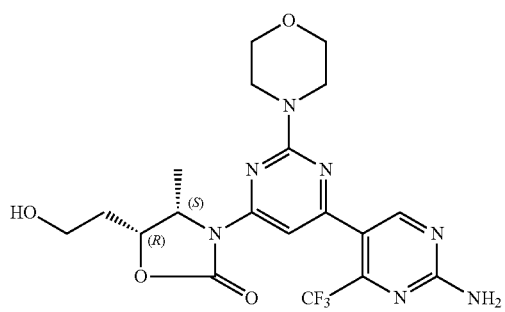

To a solution of (4S,5R)-3-(2'-amino-2-morpholino-4'-(trifluoromethyl)-[4,5'-bipyrimidin]-6-yl)-5-(2-((tert-butyl-diphenylsilyl)oxy)ethyl)-4-methyloxazolidin-2-one (2.1 g, 3 mmol) in THF (20 mL), was added dropwise 1M TBAF in THF (3 mL, 3 mmol) at 0° C. The reaction mixture was stirred for 1 h at 0° C. before evaporation. The residue was purified by flash chromatography (hexane/EtOAc/MeOH 90:10:1→0:100:10). The purified product was re-crystallized from MeOH to afford the title compound as a white solid (1.17 g, 83%): $t_R$=0.80 min (UPLC 1), $t_R$=0.82 min (LC-MS 3); ESI-MS: 470 [M+H]$^+$ (LC-MS 3).

Step 23.1: (4S,5R)-3-(2'-Amino-2-morpholino-4'-(trifluoromethyl)-[4,5'-bipyrimidin]-6-yl)-5-(2-((tert-butyldiphenylsilyl)oxy)ethyl)-4-methyloxazolidin-2-one

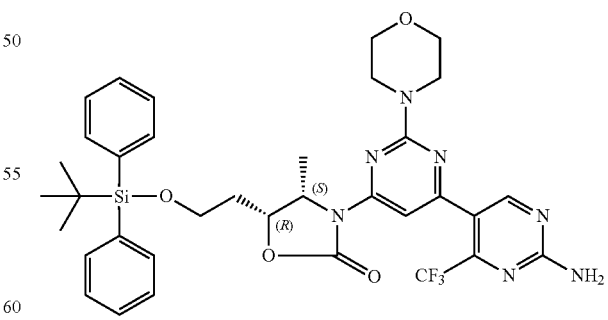

The title compound was prepared in analogy to the procedure described for example 22.1 from 4S,5R)-5-(2-((tert-butyldiphenylsilyl)oxy)ethyl)-3-(6-chloro-2-morpholinopyrimidin-4-yl)-4-methyloxazolidin-2-one and intermediate B to afford the title compound after crystallization from MeOH: $t_R$=1.72 min (UPLC 1), $t_R$=1.55 min (LC-MS 3); ESI-MS: 708 [M+H]$^+$ (LC-MS 3).

Step 23.2: (4S,5R)-5-(2-((tert-butyldiphenylsilyl)oxy)ethyl)-3-(6-chloro-2-morpholinopyrimidin-4-yl)-4-methyloxazolidin-2-one

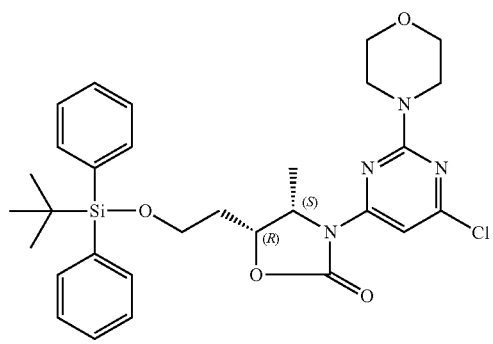

The title compound was prepared in analogy to the procedure described for step 21.1 from a 4:1 mixture of the (4S,5R)- and (4S,5S)-diastereoisomer of 5-(2-((tert-butyldiphenylsilyl)oxy)ethyl)-3-(6-chloro-2-morpholinopyrimidin-4-yl)-4-methyloxazolidin-2-one and intermediate A to afford after removal of the (4S,5S)-diastereoisomer by two re-crystallizations from THF/MeOH only the (4S,5R)-diastereoisomer of the title compound: $t_R$=1.88 min (UPLC 1), $t_R$=1.64 min (LC-MS 3); ESI-MS: 581, 583 [M+H]$^+$ (LC-MS 3); $^1$H NMR (400 MHz, DMSO-d$_6$): δ 1.08 (s, 9H), 1.36 (d, 3H), 2.02 (m, 2H), 3.70-3.90 (m, 10H), 4.82 (m, 2H), 7.40-7.50 (m, 6H), 7.51 (s, 1H), 7.67 (m, 4H).

Step 23.3: (4S,5R)- and (4S,5S)-5-(2-((tert-butyl-diphenylsilyl)oxy)ethyl)-4-methyloxazolidin-2-one

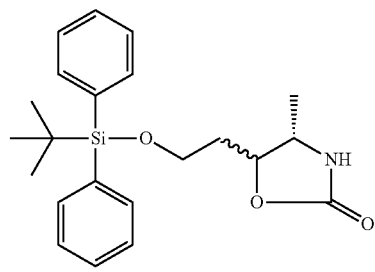 [SMILES: C[C@@H]1NC(=O)OC1CCO[Si](c1ccccc1)(c1ccccc1)C(C)(C)C]

To a solution of a 4:1 mixture of the (4S,5R)- and (4S,5S)-diastereoisomer of 5-(2-((tert-butyl-diphenylsilyl)oxy) ethyl)-3-(4-methoxybenzyl)-4-methyloxazolidin-2-one (4.1 g, 7.8 mmol) in acetonitrile (40 mL) was added a solution of (NH$_4$)$_2$Ce(NO$_3$)$_6$ (10.71 g, 19.5 mmol) in H$_2$O (20 mL) at 0° C. The reaction mixture was stirred for 4 h at 0-5° C. The mixture was added to ice-water and the product extracted with EtOAc. Combined extracts were washed with saturated NaHCO$_3$ solution and brine, dried over MgSO$_4$, filtered and concentrated. The title compound was obtained after purification by flash chromatography (heptane/EtOAc 10:1→EtOAc) as a 4:1 mixture of diastereomers (2.2 g, 71%): TLC (hexane-EtOAc 1:1) R$_f$=0.23; $t_R$=1.47 min (UPLC 1), $t_R$, 1.33 min (LC-MS 3); ESI-MS: 401 [M+NH4]$^+$ (LC-MS 3).

Step 23.4: (4S,5R)- and (4S,5S)-5-(2-((tert-butyl-diphenylsilyl)oxy)ethyl)-3-(4-methoxybenzyl)-4-methyloxazolidin-2-one

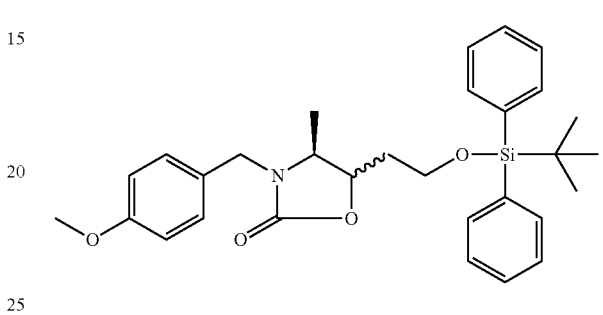

To a solution of a 4:1 mixture of the (4S,5R)- and (4S,5S)-diastereomers of 5-(2-hydroxyethyl)-3-(4-methoxybenzyl)-4-methyloxazolidin-2-one (2.65 g, 10 mmol) in DMF (30 mL) was added imidazole (1.73 g, 25 mmol) and TBDPSCl (3.57 g, 13 mmol) at 0-5° C. The reaction mixture was allowed to warm to RT and was stirred overnight at RT. The reaction mixture was concentrated and the residual oil was dissolved in TBME and washed with 10% aqueous KHSO$_4$ solution, H$_2$O, saturated NaHCO$_3$ solution and brine, dried over MgSO$_4$, filtered and concentrated. The title compound was obtained after purification by flash chromatography (heptane/EtOAc 20:1→2:1) as a 4:1 mixture of diastereomers (4.18 g, 80%): TLC (hexane/EtOAc 3:1) R$_f$=0.27; $t_R$=1.70 min (UPLC 1), $t_R$, 1.52 min (LC-MS 3); ESI-MS: 526 [M+Na]$^+$ (LC-MS 3).

Step 23.5: (4S,5R)- and (4S,5S)-5-(2-hydroxyethyl)-3-(4-methoxybenzyl)-4-methyloxazolidin-2-one

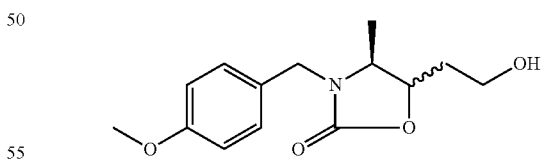

A 4:1 mixture of (4S,5R)- and (4S,5S)-allyl-3-(4-methoxybenzyl)-4-methyloxazolidin-2-one (2.67 g, 10 mmol) in CH$_2$Cl$_2$-MeOH 2:1 (40 mL) was ozonated at −78° C. After complete ozonide formation NaBH$_4$ (0.57 g, 15 mmol) was added and the reaction mixture was allowed to warm to RT and stirred for 2 h at RT. The reaction mixture was added to a 20% aqueous K$_2$CO$_3$ solution and the product was extracted with EtOAc. Combined extracts were washed with brine, dried over MgSO$_4$, filtered and concentrated to afford the title compound as a light yellow oil (2.65 g, 99%): TLC (EtOAc)

R$_f$=0.28; t$_R$=0.68 min (UPLC 1), t$_R$, 0.69 min (LC-MS 3); ESI-MS: 266 [M+H]$^+$ (LC-MS 3).

Step 23.6: (4S,5R)- and (4S,5S)-5-allyl-3-(4-methoxybenzyl)-4-methyloxazolidin-2-one

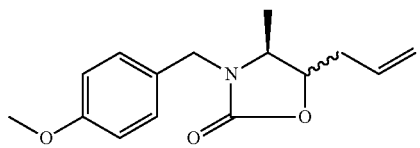 [SMILES: C=CCC1OC(=O)N(Cc2ccc(OC)cc2)[C@H]1C]

To a solution of a 4:1 mixture of benzyl ((2S,3R)-3-hydroxyhex-5-en-2-yl)(4-methoxybenzyl)-carbamate and benzyl ((2S,3S)-3-hydroxyhex-5-en-2-yl)(4-methoxybenzyl) carbamate (3.55 g, 9.5 mmol) in THF (60 mL) was added under argon at −50° C. a 1M solution of NaHMDS in THF (10.5 mL). After stirring the reaction mixture for 0.5 h at −40° C. the mixture was added to cold 10% aqueous KHSO$_4$ solution and the product was extracted with EtOAc. Combined extracts were washed with brine, dried over MgSO$_4$, filtered and concentrated. The title compound was obtained after purification by flash chromatography (hexane/EtOAc 10:1→1:1) as a colorless oil (2.4 g, 97%): TLC (hexane/EtOAc 1:1) R$_f$=0.42; t$_R$=1.03 min (UPLC 1), t$_R$, 0.99 min (LC-MS 3); ESI-MS: 262 [M+H]$^+$ (LC-MS 3); $^1$H NMR (400 MHz, DMSO-d$_6$): δ 1.06 (d, 2.4H), 1.13 (d, 0.6H), 2.30-2.40 (m, 2H), 3.25 (m, 0.2H), 3.66 (m, 0.8H, strong NOE to signal at 4.54), 3.75 (s, 3H), 4.07 (d, 1H), 4.10 (m, 0.2H), 4.48 (d, 1H), 4.54 (m, 0.8H), 5.05-5.20 (m, 2H), 5.23 (m, 0.2H), 5.78 (m, 0.8H), 6.92 (d, 2H), 7.22 (d, 0.4H), 7.24 (d, 1.6H).

Step 23.7: (2S,3R)- and (2S,3S)-benzyl 4-methoxybenzyl(1-oxopropan-2-yl)carbamate

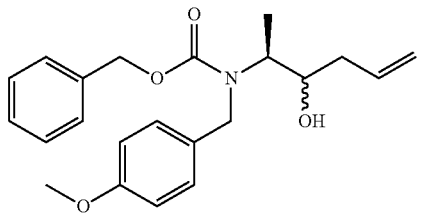 [SMILES: C=CCC(O)[C@H](C)N(Cc1ccc(OC)cc1)C(=O)OCc1ccccc1]

To a solution of (S)-benzyl 4-methoxybenzyl(1-oxopropan-2-yl)carbamate (3.86 g, 10 mmol) in THF (30 mL) was added zinc dust (1.64 g, 25 mmol), saturated aqueous NH$_4$Cl solution (5 mL) and allyl bromide (2.2 mL, 25 mmol) and the reaction mixture was stirred for 1 h at 25-30° C. The reaction mixture was diluted with H$_2$O and the product was extracted EtOAc. Combined extracts were washed with 10% aqueous KHSO$_4$ solution, H$_2$O, NaHCO$_3$ and brine, dried over MgSO4, filtered and concentrated. The title compound was obtained after purification by flash chromatography (hexane/EtOAc 20:1→2:1) as a colorless oil (3.5 g, 97%): t$_R$=1.25 min and 1.27 min (UPLC 1) (4:1 mixture of (2S,3R)- and (2S,3S)-diastereoisomer), TLC (hexane/EtOAc 1:1) R$_f$=0.51; t$_R$, 1.68 min and 1.69 min (LC-MS 3); ESI-MS: 370 [M+H]$^+$ (LC-MS 3).

Step 23.8: (S)-benzyl 4-methoxybenzyl(1-oxopropan-2-yl)carbamate

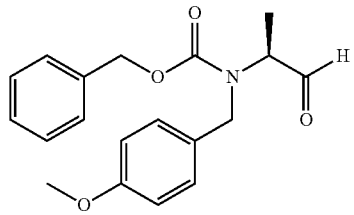 [SMILES: COc1ccc(CN(C(=O)OCc2ccccc2)[C@@H](C)C=O)cc1]

To a solution of (S)-benzyl (1-hydroxypropan-2-yl)(4-methoxybenzyl)carbamate (11.8 g, 35.5 mmol) in CH$_2$Cl$_2$ was added NaHCO$_3$ (3.28 g, 39 mmol), KBr (0.25 g, 2.1 mmol) and TEMPO 0.168 g, 1.07 mmol). The reaction mixture was cooled to 0-5° C. and the 5% aqueous NaClO solution (85 mL, 71 mmol) was added within 30 min. After stirring for 1 h at 0-5° C. the reaction mixture was added to Na$_2$S$_2$O$_3$ solution and the product was extracted with EtOAc. Combined extracts were washed with aqueous NaH$_2$PO$_4$ solution, H$_2$O and brine, dried over MgSO$_4$, filtered and concentrated to provide the title compound as a yellow oil (11.2 g, 96%): TLC (hexane/EtOAc 1:1) R$_f$=0.55; t$_R$=1.29 min (UPLC 1), t$_R$, 1.15 min (LC-MS 3); ESI-MS: 328 [M+H]$^+$ (LC-MS 3).

Step 23.10: (S)-benzyl (1-hydroxypropan-2-yl)(4-methoxybenzyl)carbamate

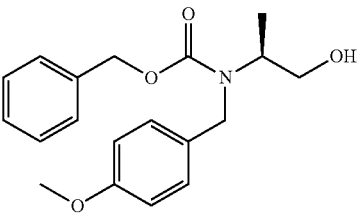 [SMILES: COc1ccc(CN(C(=O)OCc2ccccc2)[C@@H](C)CO)cc1]

To a solution of (S)-2-(((benzyloxy)carbonyl)(4-methoxybenzyl)amino)propanoic acid [439589-23-8] (16 g, 41.9 mmol) in THF (150 mL) was slowly added under argon borane dimethylsulfide (8.4 mL, 84 mmol) at 0-5° C. The reaction mixture was stirred for 1 h at 0-5° C. followed by 3 h at 40-45° C. Excess borane was destroyed by careful addition of MeOH and the reaction mixture was evaporated 3× with 200 mL MeOH and 2× with CHCl$_3$. The title compound was obtained after drying as a colorless oil (13.7 g, 99%): TLC (hexane/EtOAc 1:1) R$_f$=0.22; t$_R$=1.06 min (UPLC 1), t$_R$, 1.02 min (LC-MS 3); ESI-MS: 330 [M+H]$^+$ (LC-MS 3).

Example 24

First eluting diastereoisomer on the LC-MS 3 of (4S,5R)-3-(2'-amino-2-morpholino-4'-(trifluoromethyl)-[4,5'-bipyrimidin]-6-yl)-5-((R)-2-hydroxypropyl)-4-methyloxazolidin-2-one Absolute stereochemistry of 2-hydroxypropyl moiety not determined, (R)-configuration arbitrary assigned.

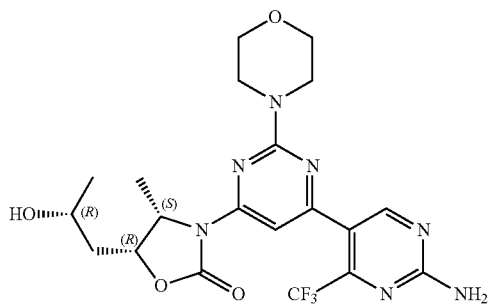

The title compound was prepared in analogy to the procedure described for example 23 from (4S,5R)-3-(2'-amino-2-morpholino-4'-(trifluoromethyl)-[4,5'-bipyrimidin]-6-yl)-5-((R)-2-((tert-butyl-diphenylsilyl)oxy)propyl)-4-methyloxazolidin-2-one and TBAF to afford after purification by flash chromatography (hexane/EtOAc 5:1→EtOAc/MeOH 10:1) and re-crystallization from MeOH the title compound as a white solid: TLC (EtOAc) $R_f$=0.50; $t_R$=0.88 min (LC-MS 3); ESI-MS: 484 [M+H]$^+$ (LC-MS 3).

Step 24.1: (4S,5R)-3-(2'-amino-2-morpholino-4'-(trifluoromethyl)-[4,5'-bipyrimidin]-6-yl)-5-aR)-2-((tert-butyldiphenylsilyl)oxy)propyl)-4-methyloxazolidin-2-one Absolute stereochemistry of the protected 2-hydroxypropyl moiety not determined, (R)-configuration arbitrary assigned.

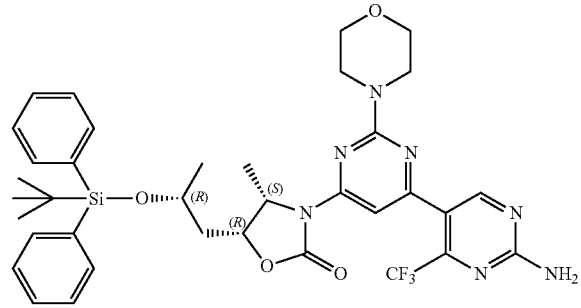

The title compound was prepared in analogy to the procedure described for step 22.1 from (4S,5R)-5-((R)-2-((tert-butyldiphenylsilyl)oxy)propyl)-3-(6-chloro-2-morpholinopyrimidin-4-yl)-4-methyloxazolidin-2-one and intermediate B to afford after purification by flash chromatography (hexane/EtOAc 20:1→EtOAc) the title compound as a light yellow foam: TLC (hexane/EtOAc 1:1) $R_f$=0.45; $t_R$=1.57 min (LC-MS 3); ESI-MS: 722 [M+H]$^+$ (LC-MS 3).

Step 24.2: (4S,5R)-5-((R)-2-((tert-butyldiphenylsilyl)oxy)propyl)-3-(6-chloro-2-morpholino-pyrimidin-4-yl)-4-methyloxazolidin-2-one Absolute stereochemistry of the protected 2-hydroxypropyl moiety not determined, (R)-configuration arbitrary assigned.

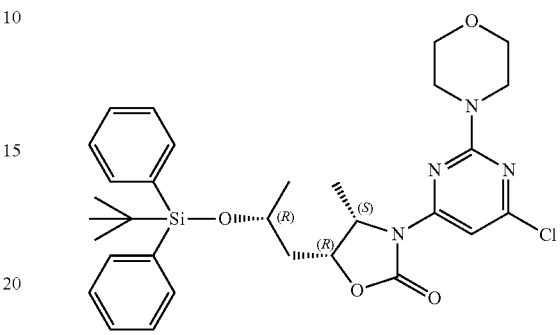

The title compound was prepared in analogy to the procedure described for step 21.1 from (4S,5R)-5-((R)-2-((tert-butyldiphenylsilyl)oxy)propyl)-4-methyloxazolidin-2-one and intermediate A to afford after purification by flash chromatography (hexane/EtOAc 20:1→3:1) the title compound as a colorless oil: TLC (hexane/EtOAc 1:1) $R_f$=0.65; $t_R$=1.67 min (LC-MS 3); ESI-MS: 595, 597 [M+H]$^+$ (LC-MS 3).

Step 24.3: (4S,5R)-5-((R)-2-((tert-butyldiphenylsilyl)oxy)propyl)-4-methyloxazolidin-2-one Absolute stereochemistry of the protected 2-hydroxypropyl moiety not determined, (R)-configuration arbitrary assigned.

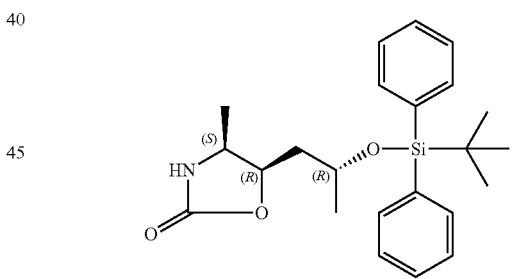

The title compound was prepared in analogy to the procedure described for step 23.3 from (4S,5R)-5-((R)-2-((tert-butyldiphenylsilyl)oxy)propyl)-3-(4-methoxybenzyl)-4-methyloxazolidin-2-one to afford after purification by flash chromatography (hexane/EtOAc 20:1→EtOAc) the title compound as a colorless oil: TLC (hexane/EtOAc 1:1) $R_f$=0.28; $t_R$=1.38 min (LC-MS 3); ESI-MS: 415 [M+NH$_4$]$^+$ (LC-MS 3).

Step 24.4: (4S,5R)-5-((R)-2-((tert-butyldiphenylsilyl)oxy)propyl)-3-(4-methoxybenzyl)-4-methyl-oxazolidin-2-one Absolute stereochemistry of the protected 2-hydroxypropyl moiety not determined, (R)-configuration arbitrary assigned.

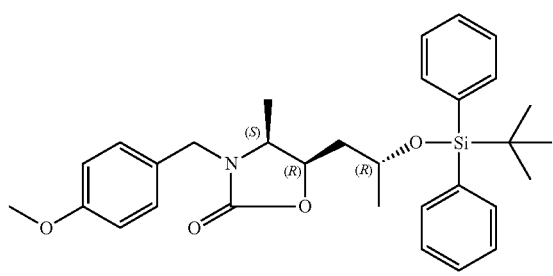

The title compound was prepared in analogy to the procedure described for step 23.4 from (4S,5R)-5-((R)-2-hydroxypropyl)-3-(4-methoxybenzyl)-4-methyloxazolidin-2-one (contaminated with 15% of the first eluting (2S,4S,5R)-diastereoisomer from step 24.5) to afford after purification by flash chromatography (hexane/EtOAc 20:1→EtOAc) the title compound as a colorless oil: TLC (hexane/EtOAc 3:1) R$_f$=0.26; t$_R$=1.55 min (LC-MS 3); ESI-MS: 540 [M+Na]$^+$ (LC-MS 3).

Step 24.5: (4S,5R)-5-((S)- and (4S,5R)-5-((R)-2-hydroxypropyl)-3-(4-methoxybenzyl)-4-methyl-oxazolidin-2-one Absolute stereochemistry of 2-hydroxypropyl moiety after reduction of the ketone was not determined, the (S)-configuration was arbitrarily assigned to the first eluting product (4S,5R,5S)-diastereoisomer.

First eluting product is the (4S,5R,5S)-diastereoisomer:

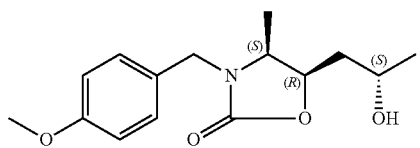

Second eluting product, mixture of (2R,4S,5R)-diastereoisomer (arbitrarily assigned (2R)-configuration for the 2-hydroxypropyl moiety):

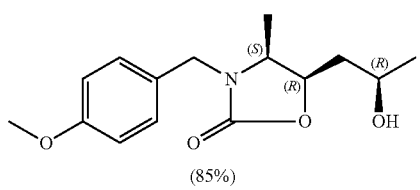

(85%)

contaminated with first eluting (4S,5R,5S)-diastereoisomer:

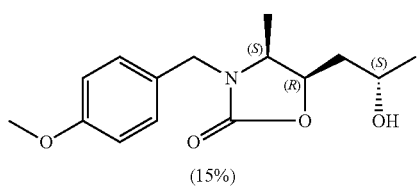

(15%)

The title compound was prepared in analogy to the procedure described for step 23.5 from a 3:1 mixture of the (4S, 5R)- and (4S,5S)-diastereoisomer of 3-(4-methoxybenzyl)-4-methyl-5-(2-methylallyl)oxazolidin-2-one to afford after multiple separations of the 3:3:1:1 mixture of isomers by flash chromatography (RediSep Rf Gold silica gel; hexane/EtOAc 1:1→EtOAc and toluene/EtOAc 3:1→EtOAc) the individual two minor (2S,4S,5S)- and (2R,4S,5S)-diastereoisomers and the individual two major (2S,4S,5R)- and (2R,4S,5R)-diastereoisomers as colorless oils:

First eluting (2S,4S,5R)-diastereoisomer of the title compound (arbitrarily assigned (2S)-configuration for the 2-hydroxypropyl moiety): TLC (EtOAc) R$_f$=0.39; t$_R$=0.752 min (UPLC 1); t$_R$=0.76 min (LC-MS 3); ESI-MS: 280 [M+H]$^+$ (LC-MS 3); $^1$H NMR (400 MHz, CDCl$_3$): δ 1.12 (d, 3H), 1.28 (d, 3H), 1.5-1.63 (m, 1H), 1.81 (m, 1H), 1.90 (d, 1H), 3.68 (m, 1H), 3.82 (s, 3H), 4.03 (d, 1H), 4.14 (m, 1H), 4.60 (ddd, 1H), 4.79 (d, 1H), 6.89 (d, 2H), 7.22 (d, 2H).

Second eluting (2R,4S,5R)-diastereoisomer of the title compound (arbitrarily assigned (2R)-configuration for the 2-hydroxypropyl moiety) contaminated with 15% of the first eluting (2S,4S,5R)-diastereoisomer: TLC (EtOAc) R$_f$=0.35; t$_R$=0.742 min and 0.752 min (UPLC 1); t$_R$=0.75 min and 0.76 min (LC-MS 3); ESI-MS: 280 [M+H]$^+$ (LC-MS 3); $^1$H NMR (400 MHz, CDCl$_3$): δ 1.12 (d, 3H), 1.28 (d, 3H), 1.50-1.64 (m, 1H), 1.81 (m, 0.15H), 1.90 (d, 0.15H). 1.94 (m, 0.85H), 2.21 (d, 0.85H), 3.67 (m, 1H), 3.82 (s, 3H), 4.01 (m, 1H), 4.13 (m, 1H), 4.73 (m, 0.85H), 4.79 (d, 0.15H), 4.80 (d, 1H), 6.90 (d, 2H), 7.22 (d, 2H).

Step 24.6: (4S,5R)- and (4S,5S)-diastereoisomer of 3-(4-methoxybenzyl)-4-methyl-5-(2-methylallyl)oxazolidin-2-one

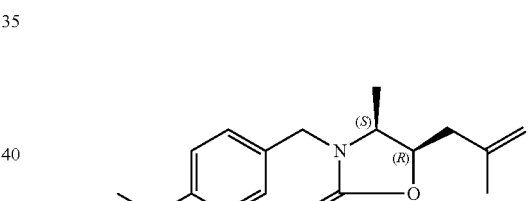

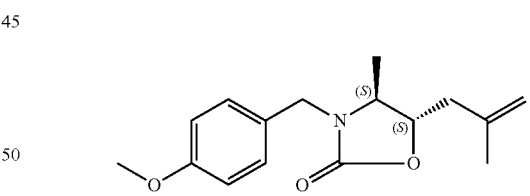

The title compound was prepared in analogy to the procedure described for step 23.6 from a 3:1 mixture of the (2S,3R)- and (2S,3S)-diastereoisomers of benzyl ((2S)-3-hydroxy-5-methylhex-5-en-2-yl)(4-methoxybenzyl)carbamate to afford after purification by flash chromatography (hexane/EtOAc 20:1→1:1) the title compound as a 3:1 mixture of the (4S,5R)- and (4S,5S)-diastereoisomer: t$_R$=1.112 min (UPLC 1); t$_R$=1.05 min (LC-MS 3); ESI-MS: 276 [M+H]$^+$ (LC-MS 3); $^1$H NMR (400 MHz, CDCl$_3$): δ 1.13 (d, 2.2H), 1.20 (d, 0.8H), 1.76 (s, 0.8H), 1.80 (s, 2.2H), 2.23 (ddd, 0.25H), 2.27 (dd, 0.75H), 2.39 (dd, 0.25H) 2.46 (dd, 0.75H), 3.28 (m, 0.25H), 3.68 (m, 0.75H), 3.83 (s, 3H), 3.99 (d, 0.75H), 4.04

(d, 0.35H), 4.14 (m, 0.25H), 4.62 (m, 0.75H), 4.70-4.90 (m, 4H), 6.90 (d, 2H), 7.25 (d, 2H).

Step 24.7: (2S,3R)- and (2S,3S)-diastereomer of Benzyl (3-hydroxy-5-methylhex-5-en-2-yl)(4-methoxybenzyl)carbamate

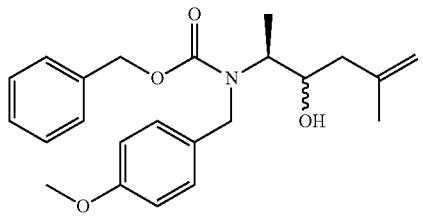 [SMILES: C=C(C)CC(O)[C@H](C)N(Cc1ccc(OC)cc1)C(=O)OCc1ccccc1]

The title compound was prepared in analogy to the procedure described for step 23.7 from (S)-benzyl 4-methoxybenzyl(1-oxopropan-2-yl)carbamate and 3-bromo-2-methylprop-1-ene to afford the title compound as a 3:1 mixture of (2S,3R)- and (2S,3S)-diastereomer: $t_R$=1.322 min (major isomer) and 1.329 min (minor isomer) (UPLC 1); $t_R$=1.23 min (major isomer) and 1.24 min (minor isomer) (LC-MS 3); ESI-MS: 384 [M+H]$^+$ (LC-MS 3).

Example 25

Second Eluting Product on the LC MS 3 which is a 9:1 Mixture of (4S,5R)- and (4S,5S)-3-(2'-amino-2-morpholino-4'-(trifluoromethyl)-[4,5'-bipyrimidin]-6-yl)-5-((S)-2-hydroxy-propyl)-4-methyloxazolidin-2-one Absolute stereochemistry of 2-hydroxypropyl moiety not determined, (S)-configuration arbitrary assigned.

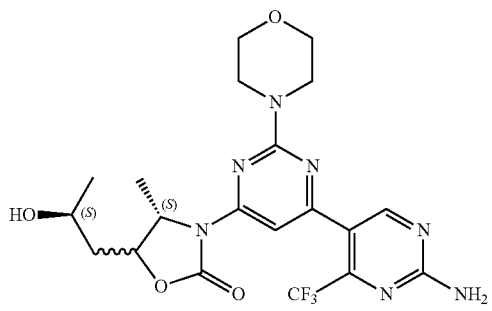

The title compound was prepared in analogy to the procedure described for example 23 from a 8:1 mixture of (4S,5R)- and (4S,5S)-3-(2'-amino-2-morpholino-4'-(trifluoromethyl)-[4,5'-bipyrimidin]-6-yl)-5-((S)-2-((tert-butyldiphenylsilyl)oxy)propyl)-4-methyloxazolidin-2-one and TBAF to afford after purification by flash chromatography (hexane/EtOAc 5:1→EtOAc/MeOH 10:1) and re-crystallization from MeOH the title compound as a white solid: TLC (EtOAc) $R_f$=0.50; $t_R$=0.87 min (minor (4S,5S)-diastereomer) and 0.89 min (major (4S,5R)-diastereomer) (LC-MS 3); ESI-MS: 484 [M+H]$^+$ (LC-MS 3).

Step 25.1: (4S,5R)- and (4S,5S)-3-(2'-amino-2-morpholino-4'-(trifluoromethyl)-[4,5'-bipyrimidin]-6-yl)-5-aS)-2-((tert-butyldiphenylsilyl)oxy)propyl)-4-methyloxazolidin-2-one Absolute stereochemistry of the protected 2-hydroxypropyl moiety was not determined, (S)-configuration arbitrary assigned.

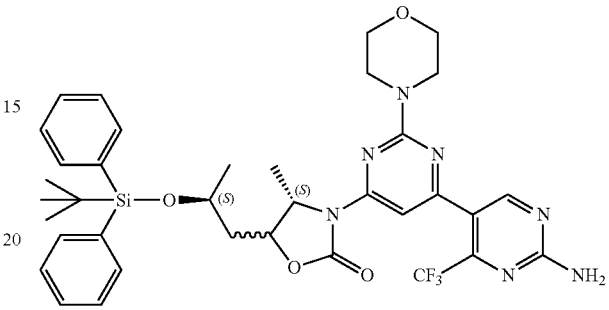

The title compound was prepared in analogy to the procedure described for step 22.1 from a 7:1 mixture of (4S,5R)- and (4S,5S)-5-((R)-2-((tert-butyldiphenylsilyl)oxy)propyl)-3-(6-chloro-2-morpholinopyrimidin-4-yl)-4-methyloxazolidin-2-one and intermediate B to afford after purification by flash chromatography (hexane/EtOAc 20:1→EtOAc) the title compound as a 8:1 mixture of (4S,5R)- and (4S,5S)-diastereoisomers: TLC (hexane/EtOAc 1:1) $R_f$=0.45; $t_R$=1.58 min (LC-MS 3); ESI-MS: 722 [M+H]$^+$ (LC-MS 3).

Step 25.2: (4S,5R)- and (4S,5S)-54(S)-2-((tert-butyldiphenylsilyl)oxy)propyl)-3-(6-chloro-2-morpholinopyrimidin-4-yl)-4-methyloxazolidin-2-one Absolute stereochemistry of the protected 2-hydroxypropyl moiety not determined, (S)-configuration arbitrary assigned.

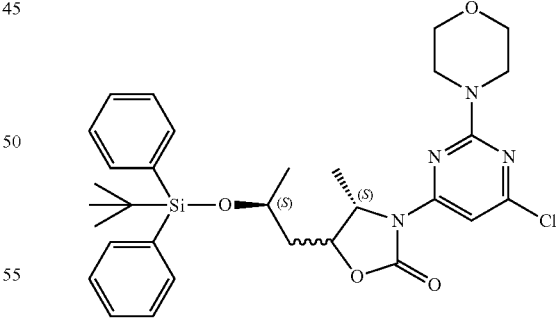

The title compound was prepared in analogy to the procedure described for step 21.1 from a 7:1 mixture of (4S,5R)- and (4S,5S)-5-((S)-2-((tert-butyldiphenylsilyl)oxy)propyl)-4-methyl-oxazolidin-2-one and intermediate A to afford after purification by flash chromatography (hexane/EtOAc 20:1→3:1) and crystallization from MeOH/THF the title compound as a 7:1 mixture of the (4S,5R)- and (4S,5S)-diastereoisomers: TLC (hexane/EtOAc 1:1) $R_f$=0.65; $t_R$=1.67 min (LC-MS 3); ESI-MS: 595, 597 [M+H]$^+$ (LC-MS 3).

Step 25.3: (4S,5R)- and (4S,5S)-54(S)-2-((tert-butyl-diphenylsilyl)oxy)propyl)-4-methyloxazolidin-2-one Absolute stereochemistry of the protected 2-hydroxypropyl moiety not determined, (S)-configuration arbitrary assigned.

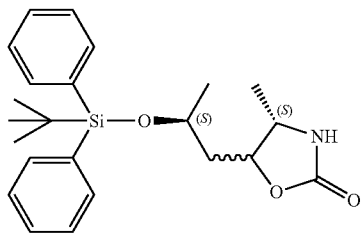

The title compound was prepared in analogy to the procedure described for step 23.3 from a 7:1 mixture of (4S,5R)- and (4S,5S)-5-((S)-2-((tert-butyldiphenylsilyl)oxy)propyl)-3-(4-methoxy-benzyl)-4-methyloxazolidin-2-one to afford after purification by flash chromatography (hexane/EtOAc 20:1→2:1) the title compound as a colorless oil as a 10:1 mixture of the (4S,5R)- and (4S,5S)-diastereoisomer: TLC (hexane/EtOAc 1:1) $R_f$=0.30; $t_R$=1.38 min (LC-MS 3); ESI-MS: 415 [M+NH$_4$]$^+$ (LC-MS 3).

Step 25.4: (4S,5R)- and (4S,5S)-54(S)-2-((tert-butyl-diphenylsilyl)oxy)propyl)-3-(4-methoxy-benzyl)-4-methyloxazolidin-2-one Absolute stereochemistry of the protected 2-hydroxypropyl moiety not determined, (S)-configuration arbitrary assigned.

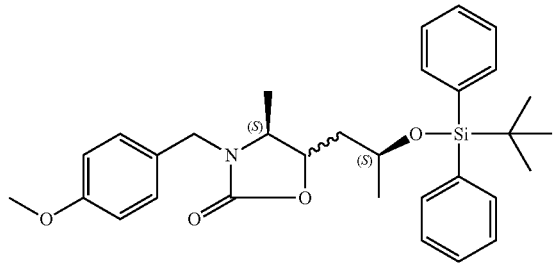

The title compound was prepared in analogy to the procedure described for step 23.4 from a 7:1 mixture of (4S,5R)- and (4S,5S)-5-((S)-2-hydroxypropyl)-3-(4-methoxybenzyl)-4-methyl-oxazolidin-2-one prepared in step 24.5 to afford after purification by flash chromatography (hexane/EtOAc 20:1→EtOAc) the title compound as a 7:1 mixture of the (4S,5R)- and (4S,5S)-diastereoisomer: TLC (hexane/EtOAc 3:1) $R_f$=0.26; $t_R$=1.56 min (LC-MS 3); ESI-MS: 540 [M+Na]$^+$ (LC-MS 3).

Example 26

(4S,5R)- and (4S,5S)-3-(2'-amino-2-morpholino-4'-(trifluoromethyl)-[4,5'-bipyrimidin]-6-yl)-5-(2-hydroxy-2-methylpropyl)-4-methyloxazolidin-2-one

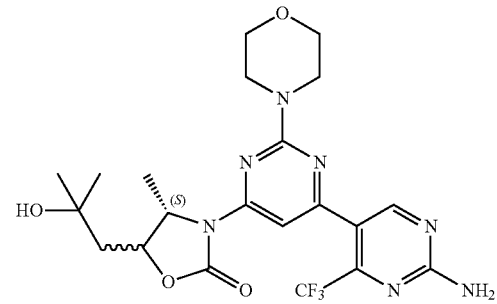

The title compound was prepared in analogy to the procedure described for step 22.1 from a 5:1 mixture of (4S,5R)- and (4S,5S)-3-(6-chloro-2-morpholinopyrimidin-4-yl)-5-(2-hydroxy-2-methylpropyl)-4-methyloxazolidin-2-one and intermediate B to afford after purification by flash chromatography (hexane/EtOAc/MeOH 90:10:1→10:100:10) and re-crystallization from MeOH the title compound as a white solid and as a 7:1 mixture of the (4S,5R)- and (4S,5S)-diastereoisomer: TLC (EtOAc) $R_f$=0.43; $t_R$=0.93 min (LC-MS 3); ESI-MS: 498 [M+H]$^+$ (LC-MS 3).

Step 26.1: (4S,5R)- and (4S,5S)-3-(6-chloro-2-morpholinopyrimidin-4-yl)-5-(2-hydroxy-2-methyl-propyl)-4-methyloxazolidin-2-one

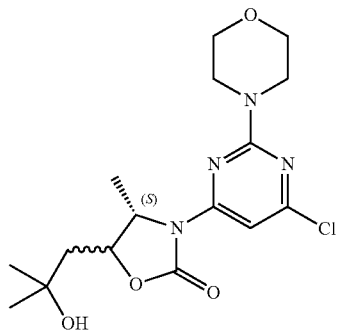

The title compound was prepared in analogy to the procedure described for step 21.1 from a 5:1 mixture of (4S,5R)- and (4S,5S)-5-((S)-2-((tert-butyldiphenylsilyl)oxy)propyl)-4-methyloxazolidin-2-one and intermediate A to afford after purification by flash chromatography (hexane/EtOAc 10:1→EtOAc) the title compound as light yellow foam and as a 5:1 mixture of the (4S,5R)- and (4S,5S)-diastereoisomers: TLC (EtOAc/MeOH 10:1) $R_f$=0.55; $t_R$=1.02 min (LC-MS 3); ESI-MS: 371, 373 [M+H]$^+$ (LC-MS 3).

Step 26.2: (4S,5R)- and (4S,5S)-5-(2-hydroxy-2-methylpropyl)-4-methyloxazolidin-2-one

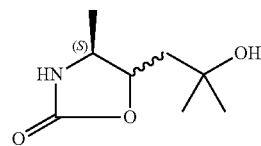

The title compound was prepared in analogy to the procedure described for step 23.3 from a 5:1 mixture of (4S,5R)- and (4S,5S)-5-(2-hydroxy-2-methylpropyl)-3-(4-methoxybenzyl)-4-methyl-oxazolidin-2-one to afford after purification by flash chromatography (hexane-EtOAc 1:1→EtOAc-MeOH 5:1) the title compound as a colorless oil as a 5:1 mixture of the (4S,5R)- and (4S,5S)-diastereoisomer: TLC (EtOAc/MeOH 10:1) $R_f$=0.40; $t_R$=0.41 min (LC-MS 3); ESI-MS: 174 [M+H]$^+$ (LC-MS 3).

Step 26.3: (4S,5R)- and (4S,5S)-5-(2-hydroxy-2-methylpropyl)-3-(4-methoxybenzyl)-4-methyl-oxazolidin-2-one

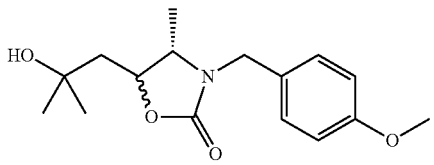 [SMILES: COc1ccc(CN2C(=O)OC(CC(C)(C)O)[C@@H]2C)cc1]

To a solution of a 3:1 mixture of methyl 2-((4S,5R)-3-(4-methoxybenzyl)-4-methyl-2-oxooxazolidin-5-yl)acetate and methyl 2-((4S,5S)-3-(4-methoxybenzyl)-4-methyl-2-oxooxazolidin-5-yl)acetate (2.0 g, 6.82 mmol) in THF (50 mL) was slowly added under argon a 3M methylmagnesium chloride solution in THF (6.82 ml, 20.46 mmol) at −78° C. After the addition the reaction mixture was allowed to warm to RT. After addition of 10% aqueous NH4Cl solution the product was extracted with EtOAc. Combined extracts were washed with H$_2$O, dried over MgSO$_4$, filtered and concentrated to afford the title compound after purification by flash chromatography (hexane/EtOAc 20:1→EtOAc) as a colorless oil (1.2 g, 59%, 3:1 mixture of (4S,5R)- and (4S,5S)-diastereoisomer): TLC (CH$_2$Cl$_2$/MeOH 10:1) $R_f$=0.43; $t_R$=0.80 min and 0.81 min (LC-MS 3); ESI-MS: 294 [M+H]$^+$ (LC-MS 3); $^1$H NMR (400 MHz, CDCl$_3$): δ 1.12 (d, 2.25H), 1.22 (d, 0.75), 1.32 (s, 1.5H), 1.34 (s, 4.5H), 1.68 (dd, 1H), 1.86 (dd, 0.25H), 1.93 (dd, 0.75H), 3.23 (m, 0.25H), 3.64 (m, 0.75H), 3.83 (s, 3H), 3.99 (d, 0.75H), 4.04 (d, 0.25H), 4.26 (d, 0.25H), 4.72 (d, 0.25H), 4.73 (m, 0.75H), 4.80 (d, 0.75H), 6.89 (d, 0.5H), 6.90 (d, 1.5H), 7.23 (d, 0.5H), 7.24 (1.5H).

Step 26.4: Methyl 24(4S,5R)-3-(4-methoxybenzyl)-4-methyl-2-oxooxazolidin-5-yl)acetate and Methyl 24(4S,5S)-3-(4-methoxybenzyl)-4-methyl-2-oxooxazolidin-5-yl)acetate

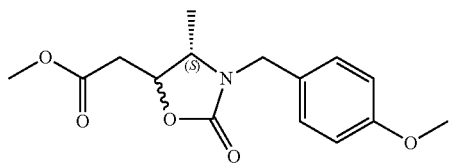

To a suspension of a 3:1 mixture of the (3R,4S)- and (3S,4S)-methyl 3-hydroxy-4-((4methoxybenzyl)amino)pentanoate (4.1 g, 10.74 mmol) in CH$_2$Cl$_2$ (80 mL) was added DIEA (8.44 ml, 48.3 mmol) and at 0° C. a solution of (bis(trichloromethyl) carbonate (2.389 g, 8.05 mmol) dissolved in CH$_2$Cl$_2$ (10 mL). After stirring for 0.5 h at RT the reaction mixture was added to saturated NaHCO$_3$ solution and the product was extracted with CH$_2$Cl$_2$. Combined extracts were washed with H$_2$O, dried over MgSO$_4$, filtered and concentrated to afford the title compound after purification by flash chromatography (hexane/EtOAc 20:1→EtOAc) as a light yellow foam (2.02 g, 63%, 3:1 mixture of the (4S,5R)- and (4S,5S)-diastereoisomers): TLC (toluene/EtOAc 1:1) $R_f$=0.47; $t_R$=0.84 min (LC-MS 3); ESI-MS: 294 [M+H]$^+$ (LC-MS 3); $^1$H NMR (400 MHz, CDCl$_3$): δ 1.11 (d, 2.25H), 1.27 (d, 0.75H), 2.57 (dd, 0.25H), 2.67 (dd, 0.75H), 2.75 (dd, 0.25H), 2.81 (dd, 0.75H), 3.34 (m, 0.25H), 3.70 (s, 0.75H), 3.73 (s, 2.25H), 3.77 (m, 0.75H), 3.83 (s, 3H), 3.99 (d, 0.75H), 4.04 (d, 0.25H), 4.44 (m, 0.25H), 4.75 (d, 0.25H), 4.78 (d, 0.75H), 4.88 (m, 0.75H), 6.90 (d, 2H), 7.22 (d, 0.5H), 7.23 (d, 1.5H).

Step 26.5: (3R,4S)- and (3S,4S)-Methyl 3-hydroxy-4 ((4-methoxybenzyl)amino)pentanoate

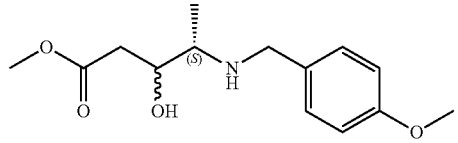

To suspension of (3R,4S)-methyl 4-amino-3-hydroxypentanoate hydrochloride [111061-25-7] (2.17 g, 11.8 mmol) in CH$_2$Cl$_2$ (60 mL) and MeOH (60 mL) was added NaOAc (1.357 g, 16.54 mmol) and after 10 min stirring p-anisaldehyde (1.37 mL, 11.2 mmol) and molecular sieve (2 g). The reaction mixture was stirred for 16 h at RT. After the addition of 2 mL of AcOH, NaBH$_3$CN (1.11 g, 17.7 mmol) was added in portions over a period of 30 min. After stirring for an additional 30 min at RT, the reaction mixture was filtered, the filtrate acidified with 4N aqueous HCl and evaporated to dryness. The residue was first washed with Et$_2$O, than suspended in CH$_2$Cl$_2$/MeOH 1:1 and the inorganic material was filtered off. The filtrate was concentrated to afford the title compound after drying at 50° C. for 4 h as a beige solid (2.9 g, 80%, 3:1 mixture of the (3R,4S)- and (3S,4S)-diastereoisomers): $t_R$=0.46 min ((3R,4S)-diastereoisomer) and 0.48 min ((3S,4S)-diastereoisomer) (LC-MS 3); ESI-MS: 268 [M+H]+(LC-MS 3).

The $^1$H NMR data for the compounds of the above examples is provided in the following table.

| Example 1 | 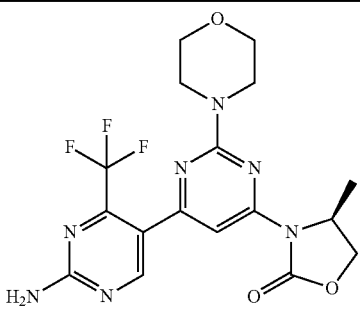 | ¹H NMR (400 MHz, <dmso>) δ ppm 1.41 (d, J = 6.26 Hz, 3 H) 3.67 (dd, J = 15.25, 4.30 Hz, 8 H) 4.10 (dd, J = 8.60, 3.13 Hz, 1 H) 4.52 (t, J = 8.21 Hz, 1 H) 4.73-4.85 (m, 1 H) 7.41 (s, 1 H) 7.60 (br. s., 2 H) 8.56 (s, 1 H) |
|---|---|---|
| Example 2 | 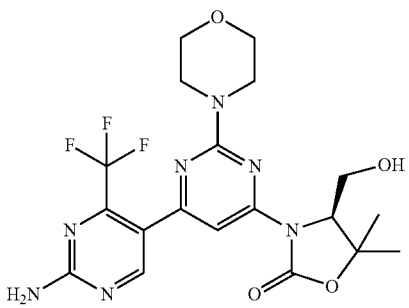 [SMILES: CC1(C)OC(=O)N(c2cc(-c3cnc(N)nc3C(F)(F)F)nc(N3CCOCC3)n2)[C@H]1CO] | ¹H NMR (400 MHz, <cdcl₃>) δ ppm 1.52 (s, 3H) 1.61 (s, 3H) 3.76 (s, 8H) 3.99 (dd, J = 11.52 Hz, J = 4.10 Hz, 1H) 4.13 (dd, J = 11.52 Hz, J = 4.49 Hz, 1H), 4.45 (t, J = 4.30 Hz, 1H) 5.47 (s, 2H) 7.64 (s, 1H) 8.58 (s, 1H) |
| Example 3 (racemic) | 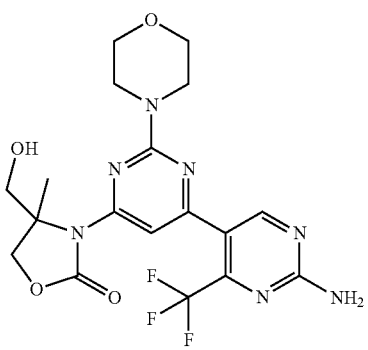 [SMILES: CC1(CO)COC(=O)N1c1cc(-c2cnc(N)nc2C(F)(F)F)nc(N2CCOCC2)n1] | ¹H NMR (400 MHz, <dmso>) δ ppm 1.55 (s, 3H) 3.51 (dd, J = 11.34 Hz, J = 5.08 Hz, 1H) 3.65 (s, 8H) 4.05 (d, J = 8.60 Hz, 1H) 4.21 (dd, J = 11.34 Hz, J = 5.67 Hz, 1H) 4.39 (d, J = 8.60 Hz, 1H) 5.26 (t, J = 5.47 Hz, 1H) 7.41 (s, 1H), 7.59 (br s, 2H), 8.54 (s, 1H) |
| Example 3A Single enantiomer. Absolute stereo-chemistry not determined. | 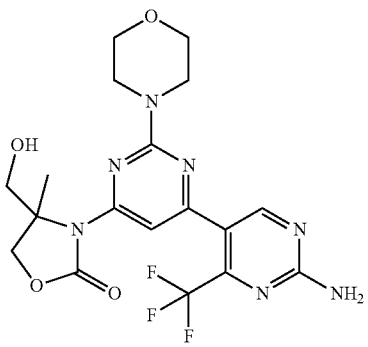 [SMILES: CC1(CO)COC(=O)N1c1cc(-c2cnc(N)nc2C(F)(F)F)nc(N2CCOCC2)n1] | ¹H NMR (400 MHz, <dmso>) δ ppm 1.55 (s, 3H) 3.51 (dd, J = 11.1 Hz, J = 5.3 Hz, 1H) 3.65 (s, 8H) 4.05 (d, J = 8.2 Hz, 1H) 4.21 (dd, J = 11.1 Hz, J = 5.7 Hz, 1H) 4.39 (d, J = 8.2 Hz, 1H) 5.26 (t, J = 5.7 Hz, 1H) 7.41 (s, 1H) 7.59 (s, 2H) 8.54 (s, 1H) |
| Example 3B Single enantiomer. Absolute stereo-chemistry not determined. | 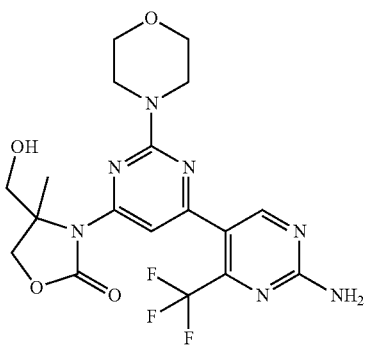 [SMILES: CC1(CO)COC(=O)N1c1cc(-c2cnc(N)nc2C(F)(F)F)nc(N2CCOCC2)n1] | ¹H NMR (400 MHz, <dmso>) δ ppm 1.55 (s, 3H) 3.51 (dd, J = 11.1 Hz, J = 5.3 Hz, 1H) 3.65 (s, 8H) 4.05 (d, J = 8.2 Hz, 1H) 4.21 (dd, J = 11.1 Hz, J = 5.7 Hz, 1H) 4.39 (d, J = 8.2 Hz, 1H) 5.26 (t, J = 5.7 Hz, 1H) 7.41 (s, 1H) 7.59 (s, 2H) 8.54 (s, 1H) |

| Example 4 | 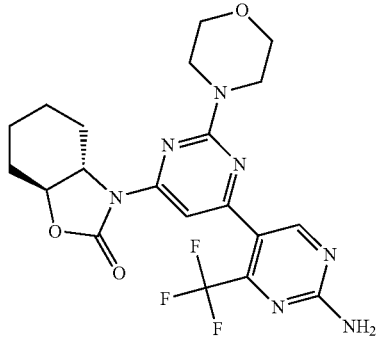 [SMILES: Nc1ncc(-c2cc(N3C(=O)O[C@H]4CCCC[C@@H]43)nc(N3CCOCC3)n2)c(C(F)(F)F)n1] | ¹H NMR (400 MHz, <dmso>) δ ppm 1.45 (br. s., 3 H) 1.57-1.96 (m, 3 H) 2.13 (d, J = 12.12 Hz, 1 H) 2.77 (br. s., 1 H) 3.65 (br. s., 8 H) 3.83-3.95 (m, 1 H) 4.12 (td, J = 11.53, 3.13 Hz, 1 H) 7.11 (s, 1 H) 7.61 (br. s., 2 H) 8.56 (s, 1 H) |
|---|---|---|
| Example 5 | 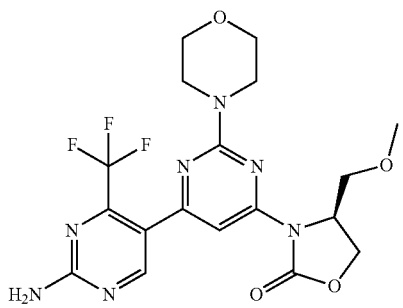 [SMILES: COC[C@H]1COC(=O)N1c1cc(-c2cnc(N)nc2C(F)(F)F)nc(N2CCOCC2)n1] | ¹H NMR (400 MHz, <cdcl3>) δ ppm 3.37-3.41 (m, 3 H) 3.69 (dd, J = 9.37, 6.25 Hz, 1 H) 3.72-3.83 (m, 9 H) 4.37-4.55 (m, 2 H) 4.83-4.97 (m, 1 H) 5.46 (s, 2 H) 7.60 (s, 1 H) 8.58 (s, 1 H) |
| Example 6 | 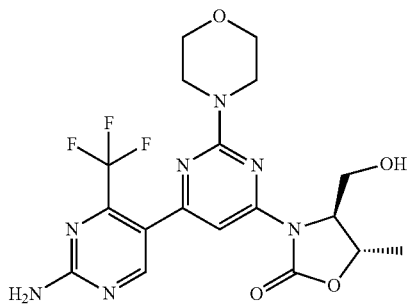 | ¹H NMR (400 MHz, cdcl3) δ ppm 3.37-3.41 (m, 3H), 3.69 (dd, 1 H), 3.72-3.83 (m, 10H), 4.37-4.55 (m, 2H), 4.83-4.97 (m, 1H), 5.46 (s, 2H), 7.60 (s, 1H), 8.58 (s, 1H). |
| Example 7 | 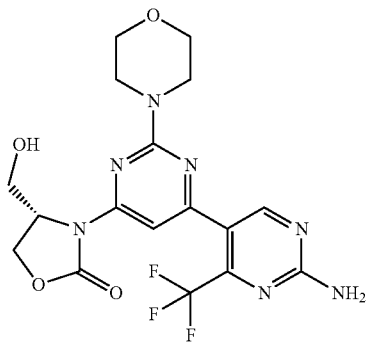 [SMILES: Nc1ncc(-c2cc(N3C(=O)OC[C@@H]3CO)nc(N3CCOCC3)n2)c(C(F)(F)F)n1] | ¹H NMR (400 MHz, <dmso>) δ ppm 3.57-3.72 (m, 9 H) 3.81-3.92 (m, 1 H) 4.36 (dd, J = 8.60, 3.13 Hz, 1 H) 4.47 (t, J = 8.60 Hz, 1 H) 4.75 (s, 1 H) 5.11 (t, J = 5.67 Hz, 1 H) 7.46 (s, 1 H) 7.59 (s, 2 H) 8.54 (s, 1 H) |

-continued

| Example 8 | 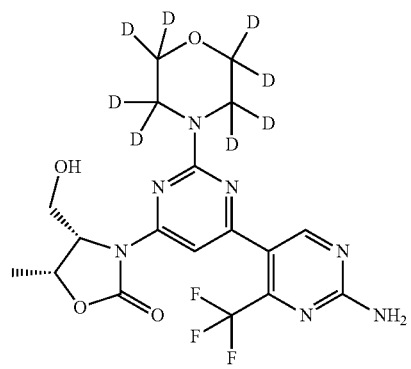 [SMILES: [2H]C1([2H])OC([2H])([2H])C([2H])([2H])N(c2nc(-c3cnc(N)nc3C(F)(F)F)cc(N3C(=O)O[C@H](C)[C@@H]3CO)n2)C1([2H])[2H]] | ¹H NMR (400 MHz, <dmso>) δ ppm 1.49 (d, J = 6.26 Hz, 3 H) 3.67 (dd, J = 11.73, 5.08 Hz, 1 H) 3.98 (dt, J = 11.63, 4.35 Hz, 1 H) 4.64 (dd, J = 7.23, 3.32 Hz, 1 H) 4.85 (m, J = 6.84 Hz, 1 H) 4.95 (t, J = 4.89 Hz, 1 H) 7.48 (s, 1 H) 7.54-7.65 (m, 2 H) 8.54 (s, 1 H) |
| Example 9 | 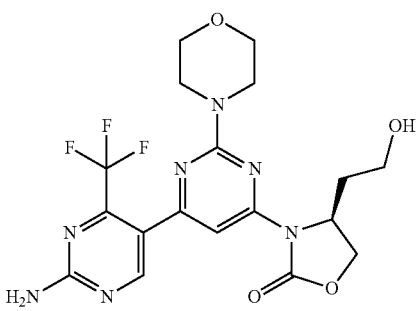 [SMILES: Nc1ncc(-c2cc(N3C(=O)OC[C@@H]3CCO)nc(N3CCOCC3)n2)c(C(F)(F)F)n1] | ¹H NMR (400 MHz, <cd3od>) δ ppm 1.86-2.00 (m, 1H) 2.18-2.34 (m, 1H) 3.65-3.85 (m, 10H) 4.38-4.46 (m, 1H) 4.49-4.60 (m, 1H) 4.91-5.02 (m, 1H) 7.51 (s, 1H) 8.53 (s, 1H) |
| Example 10 | 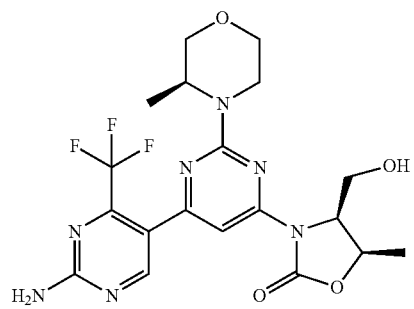 [SMILES: C[C@H]1OC(=O)N(c2cc(-c3cnc(N)nc3C(F)(F)F)nc(N3CCOC[C@@H]3C)n2)[C@H]1CO] | ¹H NMR (400 MHz, <dmso>) δ ppm 1.18 (d, J = 6.65 Hz, 3 H) 1.49 (d, J = 6.65 Hz, 3 H) 3.13 (td, J = 13.00, 3.71 Hz, 1 H) 3.33-3.44 (m, 1 H) 3.51-3.59 (m, 1 H) 3.62-3.73 (m, 2 H) 3.89 (dd, J = 11.34, 3.13 Hz, 1 H) 4.00 (dt, J = 11.53, 4.59 Hz, 1 H) 4.20 (d, J = 11.73 Hz, 1 H) 4.52 (d, J = 5.86 Hz, 1 H) 4.62 (dd, J = 7.43, 2.74 Hz, 1 H) 4.86 (m, 1 H) 4.96 (t, J = 4.69 Hz, 1 H) 7.47 (s, 1 H) 7.59 (s, 2 H) 8.54 (s, 1 H) |
| Example 11 (for comparison) | 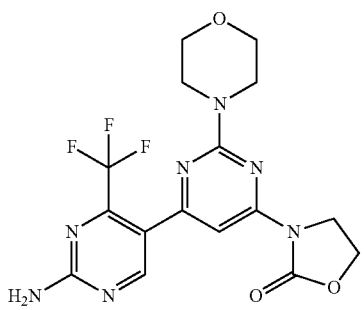 [SMILES: Nc1ncc(-c2cc(N3CCOC3=O)nc(N3CCOCC3)n2)c(C(F)(F)F)n1] | ¹H NMR (400 MHz, <dmso>) δ ppm 3.56-3.74 (m, 8H) 4.08-4.21 (m, 2H) 4.36-4.50 (m, 2H) 7.42 (s, 1H) 4.58 (s, 2H) 8.55 (s, 1H) |
| Example 12 | 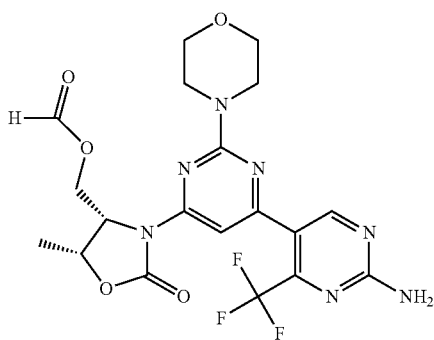 [SMILES: C[C@H]1OC(=O)N(c2cc(-c3cnc(N)nc3C(F)(F)F)nc(N3CCOCC3)n2)[C@H]1COC=O] | ¹H NMR (400 MHz, <dmso>) δ ppm 1.43 (d, J = 6.26 Hz, 3 H) 3.66 (dd, J = 15.84, 3.71 Hz, 8 H) 4.39 (d, J = 12.12 Hz, 1 H) 4.69 (dd, J = 12.51, 3.52 Hz, 1 H) 4.91-5.04 (m, 2 H) 7.43 (s, 1 H) 7.60 (s, 2 H) 8.22 (s, 1 H) 8.56 (s, 1 H) |

| Example 13 | 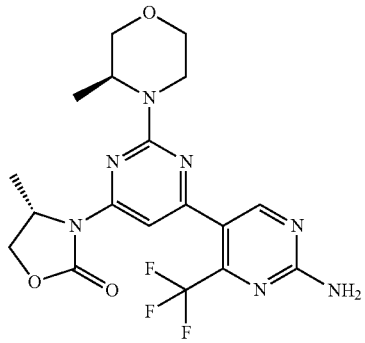 [SMILES: C[C@H]1COCCN1c1nc(-c2cnc(N)nc2C(F)(F)F)cc(N2C(=O)OC[C@@H]2C)n1] | ¹H NMR (400 MHz, <dmso>) δ ppm 1.12-1.29 (m, 3 H) 1.42 (d, J = 6.26 Hz, 3 H) 3.15 (td, J = 13.00, 3.71 Hz, 1 H) 3.35-3.47 (m, 1 H) 3.56 (dd, J = 11.53, 2.93 Hz, 1 H) 3.70 (d, J = 11.34 Hz, 1 H) 3.90 (dd, J = 11.34, 3.13 Hz, 1 H) 4.10 (dd, J = 8.21, 3.13 Hz, 1 H) 4.22 (d, J = 12.12 Hz, 1 H) 4.47-4.59 (m, 2 H) 4.73-4.85 (m, 1 H) 7.39 (s, 1 H) 7.59 (br. s., 2 H) 8.55 (s, 1 H) |
|---|---|---|
| Example 14 | 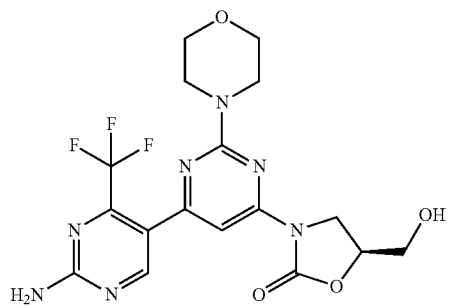 [SMILES: Nc1ncc(-c2cc(N3C[C@@H](CO)OC3=O)nc(N3CCOCC3)n2)c(C(F)(F)F)n1] | ¹H NMR (400 MHz, <dmso>) δ ppm 3.50-3.57 (m, 1H) 3.58-3.74 (m, 8H) 3.95 (dd, J = 10.3 Hz, J = 6.1 Hz, 1H) 4.16 (dd, J = 10.2 Hz, J = 9.4 Hz, 1H) 4.72 (td, J = 6.1 Hz (×2), J = 2.7, 1H) 5.2 (t, J = 5.7, 1H) 7.42 (s, 1H) 7.58 (s, 2H) 8.55 (s, 1H) |
| Example 15 | 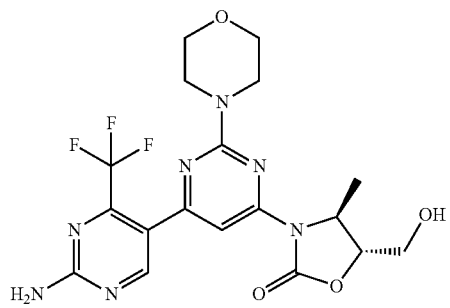 [SMILES: C[C@H]1[C@H](CO)OC(=O)N1c1cc(-c2cnc(N)nc2C(F)(F)F)nc(N2CCOCC2)n1] | ¹H NMR (400 MHz, <dmso>) δ ppm 1.32-1.59 (m, 3 H) 3.49-3.76 (m, 10 H) 4.23-4.36 (m, 1 H) 4.60 (dt, J = 6.44, 3.42 Hz, 1 H) 5.12-5.28 (m, 1 H) 7.41 (t, J = 3.12 Hz, 1 H) 7.59 (br. s., 2H) 8.55 (s, 1 H) |
| Example 16 | 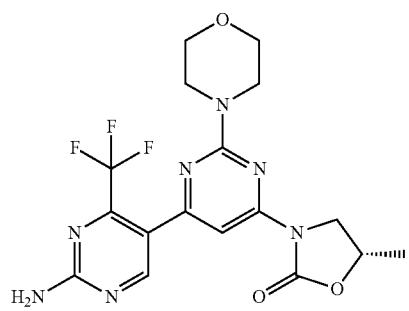 [SMILES: C[C@H]1CN(c2cc(-c3cnc(N)nc3C(F)(F)F)nc(N3CCOCC3)n2)C(=O)O1] | ¹H NMR (400 MHz, <dmso>) δ ppm 1.40 (d, J = 6.25 Hz, 3 H) 3.56-3.79 (m, 9 H) 4.29 (dd, J = 10.54, 8.20 Hz, 1 H) 4.74-4.89 (m, 1 H) 7.41 (s, 1 H) 7.59 (s, 2 H) 8.54 (s, 1 H) |

| Example 17 | 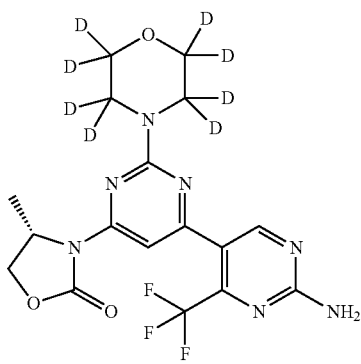 [SMILES: [2H]C1([2H])OC([2H])([2H])C([2H])([2H])N(c2nc(-c3cnc(N)nc3C(F)(F)F)cc(N3C(=O)OC[C@@H]3C)n2)C1([2H])[2H]] | $^1$H NMR (400 MHz, <dmso>) δ ppm 1.41 (d, J = 6.3 Hz, 3H) 4.1 (dd, J = 8.6 Hz, J = 3.1 Hz, 1H) 4.52 (t, J = 8.2 Hz, 1H) 4.73-4.87 (m, 1H) 7.40 (s, 1H) 7.59 (s, 2H) 8.56 (s, 1H) |
|---|---|---|
| Example 18 | 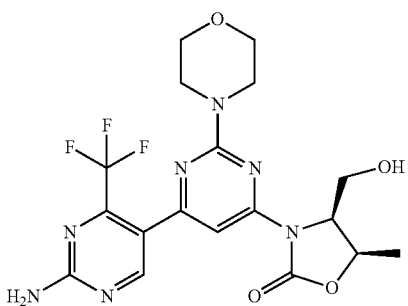 [SMILES: C[C@H]1OC(=O)N(c2cc(-c3cnc(N)nc3C(F)(F)F)nc(N3CCOCC3)n2)[C@H]1CO] | $^1$H NMR (400 MHz, <dmso>) δ ppm 1.49 (d, J = 6.26 Hz, 3 H) 3.58-3.72 (m, 9 H) 3.99 (dt, J = 11.83, 4.64 Hz, 1 H) 4.64 (dd, J = 7.43, 2.74 Hz, 1 H) 4.85 (m, 1 H) 4.96 (t, J = 4.69 Hz, 1 H) 7.48 (s, 1 H) 7.59 (s, 2 H) 8.54 (s, 1 H) |
| Example 19 | 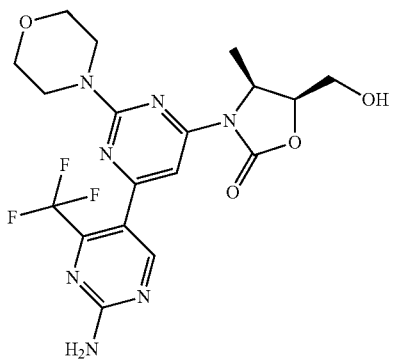 [SMILES: C[C@H]1[C@@H](CO)OC(=O)N1c1cc(-c2cnc(N)nc2C(F)(F)F)nc(N2CCOCC2)n1] | $^1$H NMR (400 MHz, <dmso>) δ ppm 1.30 (d, J = 6.26 Hz, 3 H) 3.59-3.77 (m, 10 H) 4.64-4.73 (m, 1 H) 4.85 (t, J = 6.84 Hz, 1 H) 5.15 (t, J = 5.47 Hz, 1 H) 7.40 (s, 1 H) 7.59 (s, 2 H) 8.55 (s, 1 H) |
| Example 20 | 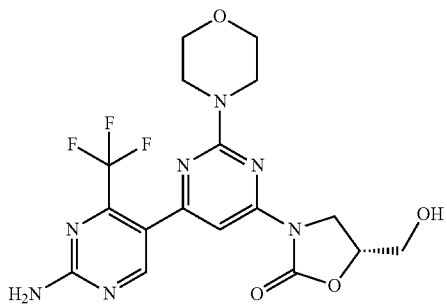 [SMILES: Nc1ncc(-c2cc(N3C[C@H](CO)OC3=O)nc(N3CCOCC3)n2)c(C(F)(F)F)n1] | $^1$H NMR (400 MHz, <dmso>) δ ppm 3.51-3.76 (m, 10 H) 3.95 (dd, J = 10.35, 6.05 Hz, 1 H) 4.16 (t, J = 9.76 Hz, 1 H) 4.66-4.82 (m, 1 H) 5.20 (t, J = 5.66 Hz, 1 H) 7.42 (s, 1 H) 7.59 (s, 2 H) 8.55 (s, 1 H) |

-continued

| | | |
|---|---|---|
| Example 21 | 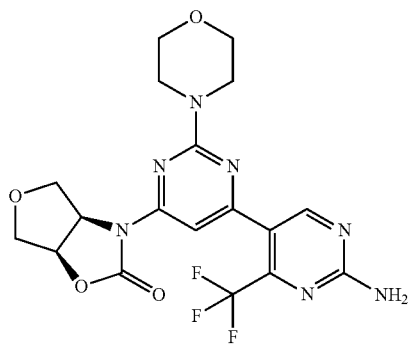 [SMILES: Nc1ncc(-c2cc(N3C(=O)O[C@H]4COC[C@H]43)nc(N3CCOCC3)n2)c(C(F)(F)F)n1] | $^1$H NMR (600 MHz, DMSO-d$_6$) δ ppm 3.60-3.75 (m, 8H), 4.12 (m, 4H), 5.15 (m, 1H), 5.26 (m, 1H), 7.47 (s, 1H), 7.62 (s, 2H), 8.59 (s, 1H). |
| Example 22 1:1 mixture of (3aR,6R,6aR)- and (3aS,6S,6aS)- diastereoisomer | 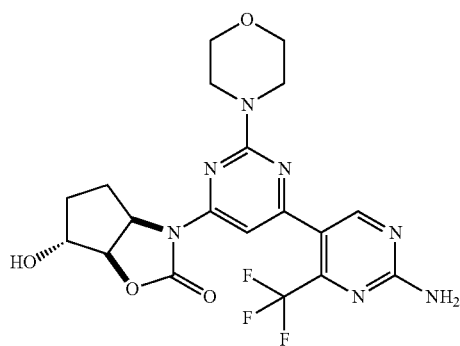 | $^1$H NMR (400 MHz, DMSO-d$_6$) δ ppm 1.04 (d, J = 6.3 Hz, 3H), 1.60-1.75 (m, 2H), 1.80-1.95 (m, 1H), 2.24 (m, 1H), 3.60-3.80 (m, 8H), 4.18 (m, 1H), 4.72 (d, J = 7.7 Hz, 1H), 5.01 (dt, J = 1.8, 7.3 Hz, 1H), 5.26 (d, J = 3.3 Hz, 1H), 7.46 (s, 1H), 7.62 (s, 2H), 8.58 (s, 1H). |
| Example 23 | 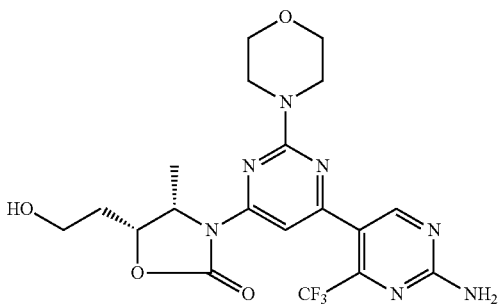 | $^1$H NMR (400 MHz, DMSO-d$_6$) δ ppm 1.30 (d, J = 6.3 Hz, 3H), 1.87 (m, 2H), 3.5-3.75 (m, 10H), 4.73 (t, J = 6.8 Hz, 1H), 4.83 (m, 2H), 7.44 (s, 1H), 7.62 (s, 2H), 8.58 (s, 1H). |
| Example 24 first eluting diastereoisomer on the LC MS 3, (R)-configuration arbitrary assigned. | 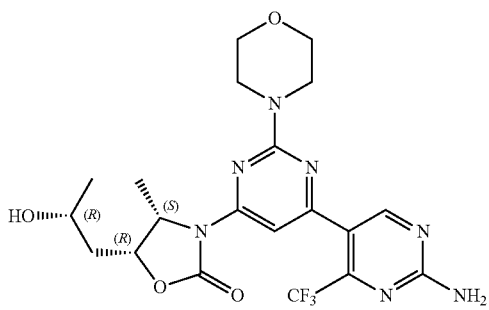 | $^1$H NMR (400 MHz, CDCl$_3$) δ ppm 1.26 (d, J = 6.2 Hz, 3H), 1.32 (d, J = 6.3 Hz, 3H), 1.75 (m, 1H), 1.96 (m, 1H), 3.41 (d, J = 6.5 Hz, 1H), 3.43 (br d, 1H), 3.69 (m, 8H), 4.03 (m, 1H), 4.72 (m, 1H), 4.80 (m, 1H), 5.38 (m, 2H), 7.50 (s, 1H), 8.51 (s, 1H). |
| Example 25 second eluting product on the LC MS 3, (S)-configuration arbitrary assigned. | 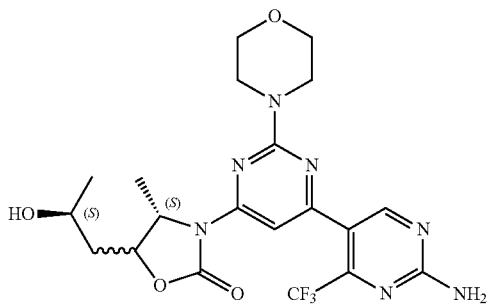 | $^1$H NMR (400 MHz, CDCl$_3$) of 9:1 mixture of (4S,5R)- and (4S,5R)- diastereoisomer δ ppm 1.25 (d, J = 6.2 Hz, 3H), 1.32 (d, J = 6.3 Hz, 2.7H), 1.48 (d, J = 6.3 Hz, 0.3H), 1.64 (m, 0.9H), 1.77 (m, 0.1H), 1.86 (m, 0.9H), 1.93 (m, 0.1H), 3.70 (m, 8H), 4.06 (m, 2H), 4.37 (m, 0.1H), 4.46 (m, 0.1H), 4.77 (m, 0.9H), 4.84 (m, 0.9H), 5.38 (m, 2H), 7.51 (s, 1H), 8.51 (s, 1H). |

| Example 26 | 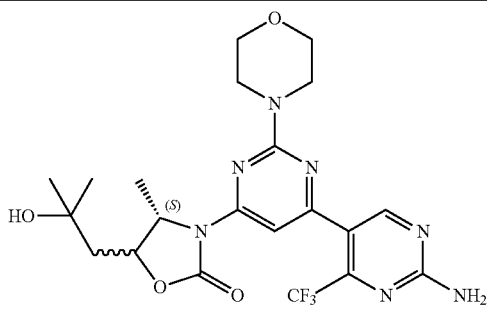 | ¹H NMR (400 MHz, CDCl₃) of 10:1 mixture of (4S,5R)- and (4S,5R)-diastereoisomer:<br>δ ppm 1.30 (br s, 8.4H), 1.33 (s, 0.3H)*, 1.56 (0.3H)*, 1.79 (d, 1H), 1.95 (dd, 1H), 3.70 (br s, 8H), 4.43 (m, 0.2H)*, 4.70-4.90 (m, 1.8H), 5.36 (br s, 2H), 7.51 (s, 1H), 8.51 (s, 1H). |
|---|---|---|

Further Physical Properties

The crystalline materials obtained from examples 10 and 18, batches A-E were further characterised as follows.

Melting Point Determination:

Melting point was determined by Differential Scanning calorimetry (DSC). DSC was measured using a TA Instruments, DSC 2000, Serial No. 100036. A sample of 1-5 mg was weighed into standard aluminium pan (pan+lid, TA 900786.901, 900779.901). The instrument was operated using the Thermal Advantage Q-Series software V.2.6.0.367 and the Thermal Advantage software V4.6.9. Thermal events were characterized using Universal Analysis V4.3A Build 4.3.0.6. The samples was measured against an empty pan. The sample was treated according to the protocol below:

Step 1: EQUILIBRATE AT −40° C.
Step 2: HEAT 10° C./min/300° C.
Modulation: No

The obtained graphs are shown in FIGS. 1, 3, 5, 7, 9 and 11.

Powder X-Ray Diffraction (PXRD):

A sample amount of ca 2-5 mg is placed on an objective glass slide and centered in the X-ray beam on a Bruker D8 GADDS Discover with CuKa anode (Serial No. 002482). Sample-Detector distance was 30 cm. Two frames were recorded between 5 and 40° 2-theta. Frames were merged using GADDS software 4.1.27. Evaluation was conducted using EVA 10.0.0.

The obtained graphs are shown in FIGS. 2, 4, 6, 8, 10 and 12.

Representative 2-theta [°] peaks are provided in the following tables:

FIG. 2 (PXRD Example 10)

| 2-theta [°] | Intensity |
|---|---|
| 9.9 | medium |
| 14.2 | medium |
| 20.1 | high |
| 23.2 | medium |
| 29.7 | medium |

FIG. 4 (PXRD Example 18A)

| 2-theta [°] | Intensity |
|---|---|
| 8.7 | medium |
| 10.6 | high |
| 18.5 | low |
| 25.3 | medium |
| 30.3 | medium |

FIG. 6 (PXRD Example 18B)

| 2-theta [°] | Intensity |
|---|---|
| 10.3 | medium |
| 15.2 | high |
| 16.0 | medium |
| 22.7 | medium |
| 23.7 | medium |

FIG. 8 (PXRD Example 18C)

| 2-theta [°] | Intensity |
|---|---|
| 10.3 | medium |
| 15.2 | high |
| 16.0 | medium |
| 20.3 | medium |
| 29.0 | low |

FIG. 10 (PXRD Example 18D)

| 2-theta [°] | Intensity |
|---|---|
| 10.3 | medium |
| 15.2 | high |
| 16.0 | medium |
| 16.8 | low |
| 20.3 | medium |

FIG. 12 (PXRD Example 18E)

| 2-theta [°] | Intensity |
|---|---|
| 10.2 | medium |
| 15.1 | high |
| 15.9 | medium |
| 20.1 | medium |
| 29.0 | medium |

Biological Activity

The efficacy of the compounds of the present invention as PI3 kinase inhibitors can be demonstrated as follows:

Preparation of Compound Dilutions (384-Well)

Test compounds were dissolved in DMSO (10 mM) and transferred into 1.4 mL flat bottom or V-shaped Matrix tubes carrying a unique 2D matrix chip by individual Novartis compound hubs. The numbers of these chips were distinctively linked to Novartis Pharma Numbers. The stock solutions were stored at −20° C. if not used immediately. For the test procedure the vials were defrosted and identified by a scanner whereby a working sheet was generated that guided the subsequent working steps.

Compounds were either manually diluted in DMSO for individual experiments (96 wells enabling 10 cpds at 8 (single points) concentrations) as described in or prepared as described below if tested for profiling in 384-wells. This format enabled the assay of maximally 40 individual test compounds at 8 concentrations (single points) including 4 reference compounds. The dilution protocol included the production of "pre-dilution plates", "master plates" and "assay plates".

Pre-Dilution Plates:

96 polypropylene well plates were used as pre-dilution plates. A total of 4 pre-dilution plates were prepared including 10 test compounds each on the plate positions A1-A10, one standard compound at A11 and one DMSO control at A12. The pattern of the dilution steps is summarized in Table 1. Programs have been written to run these pipetting steps on the HamiltonSTAR robots.

TABLE 1

Dilution pattern for pre-dilution plates

| Row | Vol (μL) | Conc. (μM) |   | Vol (μL) DMSO |   | Vol (μL) | Conc (μM) | Dil. ratio | Final concentration (μM) |
|-----|----------|------------|---|---------------|---|----------|-----------|------------|--------------------------|
| A | 30 | 10'000 | + | 135 | → | 165 | 1'820 | 1:5.5 | 10 |
| B | 50 | 1'820 | + | 116 | → | 166 | 546 | 1:3.33 | 3 |
| C | 50 | 546 | + | 100 | → | 150 | 182 | 1:3 | 1 |
| D | 50 | 182 | + | 116 | → | 166 | 54.6 | 1:3.33 | 0.3 |
| E | 50 | 54.6 | + | 100 | → | 150 | 18.2 | 1:3 | 0.1 |
| F | 50 | 18.2 | + | 116 | → | 166 | 5.46 | 1:3.33 | 0.03 |
| G | 50 | 5.46 | + | 100 | → | 150 | 1.82 | 1:3 | 0.01 |
| H | 50 | 1.82 | + | 116 | → | 166 | 0.546 | 1:3.33 | 0.003 |

DMSO was saturated with $H_2O$ to a concentration of 10%.
Vol: Volume,
Conc: Concentration,
Dil. ratio: Dilution ratio,
Fin. c: Final concentration.

Master Plates:

100 μL of individual compound dilutions including standard compound and controls of the 4 "pre-dilution plates" were transferred into a 384 "master plate" including the following concentrations 1,820, 564, 182, 54.6, 18.2, 5.46, 1.82 and 0.546 μM, respectively in 90% DMSO.

Assay Plates:

Identical "assay plates" were then prepared by pipetting 50 nL each of compound dilutions of the "master plates" into 384-well "assay plates". The compounds were mixed with 4.5 μL of assays components plus 4.5 μL enzyme corresponding to a 1:181 dilution enabling the final concentration of 10, 3.0, 1.0, 0.3, 0.1, 0.03, 0.01 and 0.003 μM, respectively. The preparation of the "master plates" was handled by the Matrix PlateMate Plus robot and replication of "assay plates" by the HummingBird robot.

Method to Generate Expression Constructs

Catalytically active human PI3Kα, PI3Kβ, PI3Kδ, and mTOR were cloned, expressed and purified as described (Maira S M, Stauffer F, Brueggen J, Furet P, Schnell C, Fritsch C, Brachmann S, Chène P, de Pover A, Schoemaker K, Fabbro D, Gabriel D, Simonen M, Murphy L, Finan P, Sellers W, García-Echeverría C (2008), *Mol Cancer Ther.* 7:1851-63 and Maira S M, Pecchi S, Brueggen J, Huh K, Schnell C, Fritsch C, Nagel T, Wiesmann M, Brachmann S, Dorsch M, Chène P, Schoemaker K, De Pover A, Menezes D, Fabbro D, Sellers W, García-Echeverría C, Voliva C F (2011), *Mol. Cancer Ther.* accepted).

Biochemical Assays for PI3Kalpha, PI3Kbeta

The luminescence-based ATP detection reagent KinaseGlo was obtained from Promega, (Cat. No. V6714, Lot No. 236161) through Catalys, Wallisellen, Switzerland. (L-alpha-phosphatidylinositol (PI), Liver, Bovine) were obtained from Avanti Polar Lipid (Cat. No. 840042C, Lot#LPI-274), Phosphatidylinositol-4,5-bisphosphate $(PIP(4,5))_2$ (Avanti, Cat. No. 840046x) or L-α-phosphatidylinositol (PI) was obtained from Avanti Polar Lipid (Cat. No. 840042C, Lot#LPI-274). L-α-Phosphatidylserine (PS) was from Avanti Polar Lipid (Cat. No. 840032C), n-OctylGlucoside Avanti Polar Lipid (Cat. No. 10634425001). Luminescence is a well established readout to determine ATP concentrations and can thus be used to follow the activity of many kinases regardless of their substrate. The Kinase Glo Luminescent Kinase Assay (Promega, Madison/Wis., USA) is a homogeneous HTS method of measuring kinase activity by quantifying the amount of ATP remaining in solution following a kinase reaction.

50 nL of compound dilutions were dispensed onto black 384-well low volume Non Binding Styrene (NBS) plates (Costar Cat. No. NBS#3676) as described in section 8.2. L-α-phosphatidylinositol (PI), provided as 10 mg/ml solution in methanol, was transferred into a glass tube and dried under nitrogen beam. It was then resuspended in 3% OctylGlucoside by vortexing and stored at 4° C. 5 μL of a mix of PI/OG with the PI3Ka and Pi3Kb subtypes were added. Kinase reactions were started by addition of 5 μl of ATP-mix containing in a final volume 10 μL 10 mM TRIS-HCl pH 7.5, 3 mM $MgCl_2$, 50 mM NaCl, 0.05% CHAPS, 1 mM DTT and 1 μM ATP, and occurred at room temperature. Reactions were stopped with 10 μl of KinaseGlo and plates were read 10 mins later in a Synergy2 reader using an integration time of 0.1 seconds per well. 2.5 μM of NVP-BGT226 (standard) was added to the assay plates to generate the 100% inhibition of the kinase reaction, and the 0% inhibition was given by the solvent vehicle (90% DMSO in water). NVP-BGT226 was used as a reference compound and included in all assay plates in the form of 16 dilution points in duplicate.

$IC_{50}$ values of the percentage inhibition of each compound at 8 concentrations (usually 10, 3.0, 1.0, 0.3, 0.1, 0.030, 0.010 and 0.003 μM) n=2 were derived by fitting a sigmoidal dose-response curve to a plot of assay readout over inhibitor concentration as described. All fits were performed with the program XLfit4 (ID Business Solutions, Guildford, UK).

Biochemical Assays for PI3Kdelta, PI3Kgamma

The TR-FRET Adapta™ Universal Kinase Assay Kit was purchased from Invitrogen Corporation (Carlsbad/CA, USA) (Cat. No. PV5099). The kit contains the following reagents: Adapta Eu-anti-ADP Antibody (Europium labeled anti-ADP antibody in HEPES buffered saline, Cat. No. PV5097), Alexa Fluor® 647-labeled ADP tracer (Alexa Fluor® 647-labeled ADP tracer in HEPES buffered saline, Cat. No. PV5098), proprietary TR-FRET dilution buffer pH 7.5 (Cat. No. PV3574).

PIK3CD substrate Phosphatidylinositol was obtained from Invitrogen (vesicules consisting of 2 mM PI in 50 mM HEPES pH7.5; Cat. No. PV5371). PIK3CG substrate Phosphatidylinositol-4,5-bisphosphate $(PIP(4,5)_2$ was obtained from Invitrogen (PIP2:PS large unilamellar vesicules consisting of 1 mM PIP2: 19 mM PS in 50 mM HEPES pH7.5, 3 mM MgCl2, 1 mM EGTA; Cat. No. PV5100).

Time-Resolved Fluorescence Resonance Energy Transfer (TR-FRET) is a technology based on energy transfer between two adjacent dyes, from an excited electron in one dye (the donor) to an electron of an adjacent dye (the acceptor) through resonance, then released as a photon. This energy transfer is detected by an increase in the fluorescence emission of the acceptor, and a decrease in the fluorescence emission of the donor. TR-FRET assays for protein kinases use a long-lifetime lanthanide Terbium or Europium chelates as the donor species which overcome interference from compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds. The Adapta™ assay can be divided into two phases: a kinase reaction phase and an ADP detection phase. In the kinase reaction phase, all kinase reaction components are added to the well and the reaction is allowed to incubate for a set period of time specific for each kinase. After the reaction, a detection solution of Eu-labeled anti-ADP antibody, Alexa Fluor® 647-labeled ADP tracer, and EDTA (to stop the kinase reaction) are added to the assay well. ADP formed by the kinase reaction will displace the Alexa Fluor® 647-labeled ADP tracer from the antibody, resulting in a decrease in TR-FRET signal. In the presence of an inhibitor, the amount of ADP formed by the kinase reaction is reduced, and the resulting intact antibody-tracer interaction maintains a high TR-FRET signal. In the Adapta™ assay, the donor (Europium-anti-ADP antibody) is excited at 340 nm and will transfer its energy to the acceptor (Alexa Fluor® 647-labeled ADP tracer). The emission from the Alexa Fluor® 647 can be monitored with a filter centered at 665 nm because it is located between the emission peaks of the donor, which is measured at 615/620 nm. 50 nL of compound dilutions were dispensed onto white 384-well small volume polystyrene plate as described in section 2.2. Then 5 µL of PI3Kg and PI3Kd and lipid substrate (PI or PIP2:PS) followed by 5 µL of ATP (final assay volume 10 µL) are incubated at RT. The standard reaction buffer for the Adapta™ TR-FRET assay contained 10 mM Tris-HCl pH 7.5, 3 mM $MgCl_2$, 50 mM NaCl, 1 mM DTT, 0.05% CHAPS. Reactions were stopped with 5 µL of a mixture of EDTA containing the Eu-labeled anti-ADP antibody and the Alexa Fluor® 647-labeled ADP tracer in TR-FRET dilution buffer (proprietary to IVG). Plates are read 15 to 60 mins later in a Synergy2 reader using an integration time of 0.4 seconds and a delay of 0.05 seconds. Control for the 100% inhibition of the kinase reaction was performed by replacing the PI3K by the standard reaction buffer. The control for the 0% inhibition was given by the solvent vehicle of the compounds (90% DMSO in $H_2O$). The standard compound NVP-BGT226 was used as a reference compound and included in all assay plates in the form of 16 dilution points in duplicate.

Data are analyzed using Excel fit software or Graphpad Prism. $EC_{50}$ values were derived by fitting a sigmoidal dose-response curve to a plot of assay readout over inhibitor concentration. All fits were performed with the program XLfit4 (ID Business Solutions, Guildford, UK). Determination of $EC_{50}$ values of the percentage inhibition of each compound at 8 concentrations (usually 10, 3.0, 1.0, 0.3, 0.1, 0.030, 0.010 and 0.003 µM) n=2 were derived by fitting a sigmoidal dose-response curve to a plot of assay readout over inhibitor concentration. All fits were performed with the program XLfit4 (ID Business Solutions, Guildford, UK).

Biochemical Assay for mTOR

TR-FRET assays for protein kinases uses a long-lifetime lanthanide Terbium or Europium chelates as the donor species which overcome interference by compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds.

Binding Assays are based on the binding and displacement of an Alexa Fluor® 647-labeled, ATP-competitive kinase inhibitors to the kinase of interest. Invitrogen's "Kinase Tracers" have been developed to address a wide range of kinase targets and are based on ATP-competitive kinase inhibitors, making them suitable for detection of any compounds that bind to the ATP site or to an allosteric site altering the conformation of the ATP site. Inhibitors that bind the ATP site include both Type I kinase inhibitors, which bind solely to the ATP site, and Type II inhibitors (e.g., Gleevec®/Imatinib, Sorafenib, BIRB-796), which bind to both the ATP site and a hydrophobic site exposed in the DFG-out (non-active) conformation. Type III inhibitors are compounds that do not compete with ATP are loosely referred to as allosteric inhibitors. A study of 15 diverse Type III inhibitors demonstrated that all but one compound was detected in the binding assay with equivalent potency to activity assays. The sole exception was a substrate-competitive compound, and thus not a true allosteric inhibitor.

In contrast to most fluorescence-based kinase activity assays, LanthaScreen® $Eu^{3+}$ Kinase Binding Assays can be read continuously, which facilitates evaluation of compounds with slow binding kinetics. Also, unlike most activity assays, binding assays can be performed using either active or non-activated kinase preparations, which enables characterization of compounds that bind preferentially to non-activated kinases, such as Gleevec®/Imatinib and some allosteric inhibitors.

In the Lanthascreen™ kinase binding assay, the donor ($Eu^{3+}$-anti-GST antibody) is excited at 340 nm and will transfer its energy to the acceptor (Alexa Fluor® 647-labeled ATP-competitive kinase inhibitor=Tracer-314). The emission from the Tracer-314 (Alexa Fluor® 647 inhibitor) can be monitored with a filter centered at 665 nm because it is located between the emission peaks of the donor, which is measured at 615/620 nm. The binding of both, the Tracer-314 and $Eu^{3+}$-anti-GST antibody, to the kinase results in a high degree of FRET from the $Eu^{3+}$-donor fluorophore to the Alexa-Fluor® 647-acceptor fluorophore on the Tracer-314.

Binding of an inhibitor to the kinase competes for binding with the tracer, resulting in a loss of FRET.

50 nL of compound dilutions were dispensed onto white 384-well small volume polystyrene plate as described in section 2.2. Then 5 µL of GST-mTOR and Europium-anti-GST antibody followed by 5 µL of tracer-314 (final assay volume 10 µL) are incubated at RT. The standard reaction buffer for the Lanthascreen™ kinase binding assay contained 50 mM HEPES pH 7.5, 5 mM MgCl2, 1 mM EGTA, 0.01% Pluronic F-127. Plates are read 60 mins later in a Synergy2 reader using an integration time of 0.2 microseconds and a delay of 0.1 microseconds.

To calculate the emission ratio, the signal emitted at 665 nm from the acceptor (Alexa Fluor® 647-labeled Tracer-314) is divided by the signal emitted at 620 nm from the donor ($Eu^{3+}$ anti-GST antibody)

Control for the 0% inhibition was given by the solvent vehicle of the compounds (90% DMSO in $H_2O$). Control for the relative 100% inhibition was performed by adding 10 µM in the mix containing GST-mTOR and Europium anti-GST antibody. An additional control for the absolute 0% inhibition is given by $Eu^{3+}$ anti-GST antibody without GST-mTOR.

Cellular Assays for PI3Kalpha, Beta and Delta

AlphaScreen (Amplified Luminescent Proximity Homogeneous Assay, ALPHA, Perkin Elmer) is a non-radioactive bead-based proximity assay technology to study biomolecular interactions in a homogenous microtiter plate format. The brand name SureFire denotes AlphaScreen assays that are adapted to quantify the phosphorylation of endogenous cellular proteins in cell lysates, by using matched antibody pairs, which consist of an anti-phospho-kinase and an anti-kinase antibody. The assay allows characterization of kinase signaling in cells as well as measurement of kinase inhibitor effects. The AlphaScreen technology provides several advantages over standard assay techniques such as ELISA, as it avoids time-consuming washing procedures and reduces plate handling. Furthermore, it is miniaturizable at least to a 384-well format and provides sensitivity down to the femtomolar range, dependent on the affinity of the antibodies included in the individual AlphaScreen SureFire assay kit. High sensitivity is reached by an intrinsic amplification mechanism, which involves production of singlet oxygen molecules. SureFire assay kits are commercially available for specific targets and include pairs of validated antibodies (PerkinElmer). This report describes common procedures applied for AlphaScreen SureFire assays and respective semi-automated steps for routine kinase inhibitor profiling in cell-based assays.

The Rat-1 cell lines stably overexpressing activated PI3K class I isoforms Rat-1 pBABEpuro Myr-HA-hp110 delta (Rat-1_PI3Kdelta) and Rat-1 pBABEpuro Myr-HA-hp110alpha (Rat-1_PI3Kalpha) and Rat-1 pBABEpuro Myr-HA-hp110 beta (Rat-1_PI3beta) were prepared as described (Maira S M, Stauffer F, Brueggen J, Furet P, Schnell C, Fritsch C, Brachmann S, Chène P, de Pover A, Schoemaker K, Fabbro D, Gabriel D, Simonen M, Murphy L, Finan P, Sellers W, García-Echeverría C (2008), Mol Cancer Ther. 7:1851-63 and Maira S M, Pecchi S, Brueggen J, Huh K, Schnell C, Fritsch C, Nagel T, Wiesmann M, Brachmann S, Dorsch M, Chène P, Schoemaker K, De Pover A, Menezes D, Fabbro D, Sellers W, García-Echeverría C, Voliva C F (2011), *Mol. Cancer Ther.*, accepted). All cell lines were cultivated in complete growth medium (DMEM high glucose, 10% (v/v) fetal bovine serum, 1% (v/v) MEM NEAA, 10 mM HEPES, 2 mM L-glutamine, puromycin (10 µg/mL for Rat-1_PI3Kdelta and Rat-1_PI3Kalpha, 4 ug/mL for Rat-1_PI3beta), 1% (v/v) Pen/Strep) to 90% confluency at 37° C./5% $CO_2$/90% humidity in a humidified $CO_2$ incubator and were split twice a week.

The following materials were used for p-AKT(S473) detection in Rat-1 cell lysates: Dulbecco's modified Eagle's medium (DMEM) high glucose (Gibco Invitrogen, Basel, Switzerland, Cat. No. 41965), Heat Inactivated Fetal Bovine Serum, Qualified (HI FBS; Gibco Invitrogen, Basel, Switzerland, Lot. No. 16140), MEM non essential amino acids (NEAA; Gibco Invitrogen, Basel, Switzerland, Cat. No. 11140), HEPES (Gibco Invitrogen, Basel, Switzerland, Cat. No. 15630), Penicillin/Streptomycin (Pen/Strep, 100×; Gibco Invitrogen, Basel, Switzerland, Cat. No. 15140-122), L-Glutamine (Gibco Invitrogen, Basel, Switzerland, Cat. No. 25030), Puromycin (Sigma Aldrich, Buchs, Switzerland, Cat. No. P9620), DMSO (MERCK, Dietikon, Switzerland, Cat. No. 8.02912.2500), $H_2O$, MilliQ-$H_2O$ unless otherwise stated (MILLIPORE QGARDOOR1, Millipore, Zug, Switzerland), Bovine serum albumine (BSA; Sigma Aldrich, Buchs, Switzerland Cat. No. A8412), SureFire p-Akt 1/2 (Ser473) Assay Kit (PerkinElmer, Schwerzenbach, Switzerland, Cat. No. TGRAS50K).

The p-Akt(S473) SureFire assay measures the phosphorylation of endogenous cellular Akt 1/2 at Ser473 in cell lysates. Using Rat-1 cells stably expressing myr-HA-tagged versions of the human PI3Kdelta, PI3Kalpha, or PI3Kbeta p110 catalytic subunit isoforms, the assay was developed as a two-plate protocol in a 384-well format.

For compound testing, the cells were seeded at a density of 4000 (Rat-1_PI3Kdelta), 7500 (Rat-1_PI3Kalpha), or 6200 (Rat-1_PI3Kbeta) cells in 20 ul complete growth medium into cell culture treated 384-well plates and were grown at 37° C./5% $CO_2$/90% humidity for 24 h. Shortly before compound transfer, the complete medium was removed, 30 ul assay buffer (DMEM high glucose, 1×MEM NEAA, 10 mM HEPES, 2 mM L-glutamine, 0.1% (w/v) BSA) was added and 10 ul of the compound predilutions were transferred to the cells. For testing after February 2010, assay buffer was substituted for complete growth medium, which revealed similar results (data not shown). After treatment with compound for 1 h, the cells were lysed by the addition of 20 ul lysis buffer supplemented with 0.24% (w/v) BSA. Detection of p-AKT (Ser473) was performed with the SureFire p-Akt 1/2 (Ser473) Assay Kit according to the manufacturer's instructions using 5 ul of cell lysate in a total detection volume of 12 ul.

$IC_{50}$ values of the percentage inhibition of each compound at 8 concentrations (usually 10, 3.0, 1.0, 0.3, 0.1, 0.030, 0.010 and 0.003 µM) n=2 were derived by fitting a sigmoidal dose-response curve to a plot of assay readout over inhibitor concentration as described. All fits were performed with the program XLfit4 (ID Business Solutions, Guildford, UK).

Cellular Assay for mTOR

A cell based assay (384-well format) was developed for determination of compound effects on cellular mTOR kinase activity in MEF (mouse embryo fibroblasts) cells derived from mice lacking TSC1 (Tuberosclerosis Complex1) a potent suppressor of mTOR kinase activity. Due to lack of TSC1 the mTOR kinase is constitutively activated resulting in permanent phosphorylation of Thr 389 of S6 kinase 1 (S6K1) which is one of the downstream targets of mTOR.

Using a SureFire Kit that enables to determine the phosphorylation of Thr389 on the S6K1 an assay was developed, validated and implemented in the Alpha-Screen format that allows the quantitative determination of phospho-T389 of S6K1 in cell lysates. Treatment of the MEF TSC1−/− cells with mTOR specific (or mTOR pathway-) inhibitors dose-dependently reduced the levels of phospho-T389 on S6K1 allowing calculation of IC50 values. These were in agreement with those values obtained with the biochemical mTOR ATP-binding assay enabling a quantitative comparison of potency of mTOR inhibitors.

TSC1−/− MEFs cells (Kwiatkowski, D. J., Zhang, H., Bandura, J. L., Heiberger, K. M., Glogauer, M., el-Hashemite, N., and Onda, H. (2002) *Hum. Mol. Genet.* 11, 525-534) were cultured in DMEM high glucose medium supplemented with 10% FBS (Invitrogen), 2 mM Glutamine and 1% (w/v) Penicillin/Streptomycin at 37° C., 5% $CO_2$.

The SureFire kit for determination of P70S6kinase phosphorylation was purchased from Perkin Elmer (p70S6K p-T389, #TGR70S50K) and the assay was performed according to the instructions of the supplier and according to the generic method for SureFire assays. Shortly, 5 µL cell lysate per well were transferred to 384-well white proxy-plates (for luminescent readout) and mixed with 7 µL A and 5 µL B (final volume: 12 µL). After 3 h incubation in the dark at RT luminescence was read with the Envision Reader (Perkin Elmer). Untreated cells were used as control (high control) and cells treated with 3 µM BEZ235 were used as low control. The assay window between the signals obtained for the high and the low controls were defined as 100% and compound effects were expressed as percent inhibition. IC50 values were calculated from the dose response curves by graphical extrapolation.

The results obtained using the above-described assays are provided in the following tables, where SEM is the standard error of the mean and n the number of data measurements.

| Biochemical PI3Kalpha | | | |
|---|---|---|---|
| Example no. | PI3Ka/ IC50 [umol I-1] | SEM | n |
| 18 | 0.009 | 0.001 | 6 |
| 15 | 0.026 | 0.012 | 3 |
| 1 | 0.008 | 0.001 | 4 |
| 4 | 0.014 | — | 1 |
| 10 | 0.008 | 0.002 | 3 |
| 19 | 0.006 | — | 1 |
| 13 | 0.203 | — | 1 |
| 20 | 0.024 | 0.003 | 6 |
| 6 | 0.013 | 0.006 | 2 |
| 8 | 0.013 | — | 1 |
| 5 | 0.011 | — | 1 |
| 16 | 0.030 | 0.010 | 2 |
| 7 | 0.021 | — | 1 |
| 12 | 0.030 | — | 1 |
| 2 | 0.023 | — | 1 |
| 3 | 0.021 | — | 1 |
| 9 | 0.384 | — | 1 |
| 11 (comparator) | 0.038 | 0.013 | 3 |
| 3A | 0.030 | — | 1 |
| 17 | 0.017 | — | 1 |
| 14 | 0.057 | 0.020 | 2 |
| 3B | 0.031 | — | 1 |
| 21 | 0.019 | — | 1 |
| 22 | 0.006 | 0.001 | 2 |
| 22A | 0.007 | 0.001 | 2 |
| 22B | 0.026 | — | 1 |
| 23 | 0.006 | 0.001 | 3 |
| 24 | 0.005 | 0.001 | 2 |
| 25 | 0.005 | — | 1* |
| 26 | 0.005 | — | 1* |
| WO2007/084786 Example 10 | 0.044 | 0.004 | 23 |
| WO2007/084786 Example 331 | 0.592 | 0.076 | 3 |
| WO2007/084786 Example 17 | 0.125 | — | 1 |
| WO2007/084786 Example 324 | 0.359 | 0.074 | 3 |
| WO2007/084786 Example 18 | 0.107 | — | 1 |
| WO2007/084786 Example 344 | 0.134 | 0.028 | 3 |
| WO2007/084786 Example 85 | 0.028 | 0.012 | 2 |

*a different, separate measurement gave a value of <0.003 uM.

| Biochemical PI3Kbeta | | | |
|---|---|---|---|
| Example no. | PI3Kb/ IC50 [umol I-1] | SEM | n |
| 18 | 0.004 | 0.001 | 6 |
| 15 | 0.021 | 0.009 | 3 |
| 1 | 0.006 | 0.001 | 4 |
| 4 | 0.007 | — | 1 |
| 10 | 0.038 | 0.025 | 3 |
| 19 | 0.005 | — | 1 |
| 13 | 0.146 | — | 1 |
| 20 | 0.011 | 0.002 | 6 |
| 6 | 0.007 | 0.003 | 2 |
| 8 | 0.004 | — | 1 |
| 5 | 0.011 | — | 1 |
| 16 | 0.020 | 0.009 | 2 |
| 7 | 0.006 | — | 1 |
| 12 | 0.049 | — | 1 |
| 2 | 0.020 | — | 1 |
| 3 | 0.018 | — | 1 |
| 9 | 0.041 | — | 1 |
| 11 (comparator) | 0.012 | 0.002 | 3 |
| 3A | 0.012 | — | 1 |
| 17 | 0.007 | — | 1 |
| 14 | 0.018 | 0.003 | 2 |
| 3B | 0.032 | — | 1 |
| 21 | 0.035 | — | 1 |
| 22 | 0.048 | 0.038 | 2 |
| 22A | 0.086 | 0.038 | 2 |
| 22B | 0.058 | — | 1 |
| 23 | 0.011 | 0.007 | 2 |
| 24 | 0.016 | — | 1 |
| 25 | 0.011 | 0.003 | 2 |
| 26 | 0.124 | 0.067 | 2 |
| WO2007/084786 Example 10 | 0.165 | 0.018 | 22 |
| WO2007/084786 Example 331 | 2.747 | 0.200 | 3 |
| WO2007/084786 Example 17 | 0.214 | — | 1 |
| WO2007/084786 Example 324 | 1.249 | 0.468 | 3 |
| WO2007/084786 Example 18 | 0.192 | — | 1 |
| WO2007/084786 Example 344 | 0.875 | 0.321 | 3 |
| WO2007/084786 Example 85 | 0.037 | 0.023 | 2 |

| Biochemical PI3Kdelta | | | |
|---|---|---|---|
| Example no. | PIK3d/ IC50 [umol I-1] | SEM | n |
| 18 | 0.008 | 0.001 | 5 |
| 15 | 0.015 | 0.003 | 3 |
| 1 | 0.007 | 0.002 | 4 |
| 4 | 0.004 | — | 1 |
| 10 | 0.012 | 0.003 | 3 |
| 19 | 0.009 | — | 1 |
| 13 | 0.021 | — | 1 |
| 20 | 0.023 | 0.007 | 6 |
| 6 | 0.011 | 0.001 | 2 |
| 8 | 0.021 | — | 1 |
| 5 | 0.004 | — | 1 |
| 16 | 0.021 | 0.001 | 2 |
| 7 | 0.017 | — | 1 |
| 12 | 0.059 | — | 1 |
| 2 | 0.075 | — | 1 |
| 3 | 0.012 | — | 1 |
| 9 | 0.032 | — | 1 |
| 11 (comparator) | 0.029 | 0.016 | 3 |
| 3A | 0.041 | — | 1 |
| 17 | 0.008 | — | 1 |
| 14 | 0.017 | 0.002 | 2 |
| 3B | 0.063 | — | 1 |
| 21 | 0.017 | — | 1 |
| 22 | 0.006 | 0.0025 | 2 |
| 22A | 0.004 | 0.0020 | 2 |
| 22B | 0.005 | — | 1 |
| 23 | 0.009 | 0.0003 | 3 |
| 24 | 0.009 | 0.0022 | 2 |
| 25 | 0.007 | 0.0025 | 2 |
| 26 | 0.012 | 0 | 2 |
| WO2007/084786 Example 10 | 0.236 | 0.057 | 11 |
| WO2007/084786 Example 331 | 2.316 | 0.246 | 3 |
| WO2007/084786 Example 17 | 0.296 | — | 1 |
| WO2007/084786 Example 324 | 0.692 | 0.037 | 3 |
| WO2007/084786 Example 18 | 0.153 | — | 1 |
| WO2007/084786 Example 344 | 1.039 | 0.585 | 2 |
| WO2007/084786 Example 85 | 0.080 | 0.039 | 2 |

| Biochemical PI3Kgamma | | | |
|---|---|---|---|
| Example no. | PIK3g/ IC50 [umol I-1] | SEM | n |
| 18 | 0.253 | 0.070 | 6 |
| 15 | 0.338 | 0.043 | 3 |
| 1 | 0.276 | 0.068 | 4 |
| 4 | 0.238 | — | 1 |
| 10 | 0.158 | 0.011 | 3 |
| 19 | 0.184 | — | 1 |
| 13 | 0.386 | — | 1 |
| 20 | 0.601 | 0.216 | 6 |
| 6 | 0.258 | 0.027 | 2 |
| 8 | 0.237 | — | 1 |
| 5 | 0.329 | — | 1 |
| 16 | 0.770 | 0.319 | 2 |
| 7 | 0.529 | — | 1 |
| 12 | 1.661 | — | 1 |
| 2 | 0.348 | — | 1 |
| 3 | 0.516 | — | 1 |
| 9 | 1.130 | — | 1 |
| 11 (comparator) | 0.998 | 0.350 | 3 |
| 3A | 2.197 | — | 1 |
| 17 | 0.328 | — | 1 |
| 14 | 1.232 | 0.679 | 2 |
| 3B | 1.794 | — | 1 |
| 21 | 0.370 | — | 1 |
| 22 | 0.145 | 0.035 | 2 |
| 22A | 0.110 | 0.035 | 2 |
| 22B | 0.410 | — | 1 |
| 23 | 0.207 | 0.087 | 3 |
| 24 | 0.540 | 0.340 | 2 |
| 25 | 0.205 | 0.095 | 2 |
| 26 | 0.290 | 0.050 | 2 |
| WO2007/084786 Example 10 | 1.898 | 0.675 | 11 |
| WO2007/084786 Example 331 | 4.626 | * | 3 |
| WO2007/084786 Example 17 | 5.270 | — | 1 |
| WO2007/084786 Example 324 | 4.322 | 0.023 | 3 |
| WO2007/084786 Example 18 | 8.789 | — | 1 |
| WO2007/084786 Example 344 | >9.1 | ** | 2 |
| WO2007/084786 Example 85 | 0.464 | 0.231 | 2 |

* 2 of the 3 values >9.1. No SEM calculation possible.
** Both values >9.1. No SEM calculation possible.

| Cellular assay PI3Kalpha | | | |
|---|---|---|---|
| Example no. | Rat1-PI3Ka/ IC50 [umol I-1] | SEM | n |
| 18 | 0.038 | 0.011 | 7 |
| 15 | 0.079 | 0.026 | 4 |
| 1 | 0.048 | 0.006 | 5 |
| 4 | 0.031 | — | 1 |
| 10 | 0.061 | 0.013 | 3 |
| 19 | 0.050 | 0.007 | 2 |
| 13 | 0.058 | — | 1 |
| 20 | 0.158 | 0.033 | 5 |
| 6 | 0.094 | 0.015 | 3 |
| 8 | 0.081 | — | 1 |
| 5 | 0.093 | — | 1 |
| 16 | 0.108 | — | 1 |
| 7 | 0.120 | 0.007 | 2 |
| 12 | 0.113 | — | 1 |
| 2 | 0.134 | — | 1 |
| 3 | 0.147 | — | 1 |
| 9 | 0.147 | — | 1 |
| 11 (comparator) | 0.256 | 0.076 | 3 |
| 3A | 0.176 | — | 1 |
| 17 | 0.178 | — | 1 |
| 14 | 0.277 | 0.075 | 2 |
| 3B | 0.215 | — | 1 |
| 21 | 0.085 | — | 1 |
| 22 | 0.095 | 0.009 | 2 |
| 22A | 0.086 | 0.009 | 2 |
| 22B | 0.148 | — | 1 |
| 23 | 0.020 | 0.007 | 4 |
| 24 | 0.045 | 0 | 2 |
| 25 | 0.045 | 0.013 | 2 |
| 26 | 0.058 | 0.031 | 2 |
| WO2007/084786 Example 10 | 0.117 | 0.012 | 20 |
| WO2007/084786 Example 331 | 1.770 | 0.080 | 2 |

-continued

Cellular assay PI3Kalpha

| Example no. | Rat1-PI3Ka/ IC50 [umol I-1] | SEM | n |
|---|---|---|---|
| WO2007/084786 Example 17 | 0.460 | — | 1 |
| WO2007/084786 Example 324 | 1.730 | 0.420 | 2 |
| WO2007/084786 Example 18 | 0.669 | — | 1 |
| WO2007/084786 Example 344 | 1.247 | 0.035 | 3 |
| WO2007/084786 Example 85 | 0.126 | 0.017 | 4 |

Cellular assay PI3Kbeta

| Example no. | Rat1-PI3Kb/ IC50 [umol I-1] | SEM | n |
|---|---|---|---|
| 18 | 0.088 | 0.035 | 6 |
| 15 | 0.114 | 0.010 | 3 |
| 1 | 0.065* | 0.029 | 3 |
| 4 | 0.183 | — | 1 |
| 10 | 0.173 | 0.060 | 4 |
| 19 | 0.071 | — | 1 |
| 13 | 0.240 | — | 1 |
| 20 | 0.124 | 0.032 | 5 |
| 6 | 0.147 | 0.128 | 2 |
| 8 | 0.108 | — | 1 |
| 5 | 0.314 | — | 1 |
| 16 | 0.160 | — | 1 |
| 7 | 0.132 | — | 1 |
| 12 | 0.123 | — | 1 |
| 2 | 0.278 | — | 1 |
| 3 | 0.193 | — | 1 |
| 9 | 0.226 | — | 1 |
| 11 (comparator) | 0.184 | 0.031 | 3 |
| 3A | 0.093 | — | 1 |
| 17 | 0.171 | — | 1 |
| 14 | 0.157 | 0.026 | 2 |
| 3B | 0.331 | — | 1 |
| 21 | 0.046 | — | 1 |
| 22 | 0.077 | 0.017 | 2 |
| 22A | 0.060 | 0.017 | 2 |
| 22B | 0.125 | — | 1 |
| 23 | 0.027 | 0.013 | 4 |
| 24 | 0.034 | 0.013 | 2 |
| 25 | 0.043 | 0.009 | 2 |
| 26 | 0.075 | 0.037 | 2 |
| WO2007/084786 Example 10 | 0.523 | 0.047 | 18 |
| WO2007/084786 Example 331 | 8.220 | ** | 2 |
| WO2007/084786 Example 17 | 1.540 | — | 1 |
| WO2007/084786 Example 324 | 5.310 | ** | 2 |
| WO2007/084786 Example 18 | 1.580 | — | 1 |
| WO2007/084786 Example 344 | 4.035 | 0.540 | 4 |
| WO2007/084786 Example 85 | 0.229 | 0.049 | 4 |

*fourth measurement 3.9 uM, outlier
** The second value was >10. Therefore no SEM calculation was possible.

Cellular assay PI3Kdelta

| Example no. | Rat1-PI3Kd/ IC50 [umol I-1] | SEM | n |
|---|---|---|---|
| 18 | 0.028 | 0.006 | 7 |
| 15 | 0.053 | 0.020 | 4 |
| 1 | 0.027 | 0.005 | 4 |
| 4 | 0.013 | — | 1 |
| 10 | 0.052 | 0.011 | 3 |
| 19 | 0.034 | 0.010 | 2 |
| 13 | 0.042 | — | 1 |
| 20 | 0.111 | 0.017 | 5 |
| 6 | 0.037 | 0.003 | 3 |
| 8 | 0.054 | — | 1 |
| 5 | 0.023 | — | 1 |
| 16 | 0.087 | — | 1 |
| 7 | 0.070 | 0.015 | 3 |
| 12 | 0.092 | — | 1 |
| 2 | 0.081 | — | 1 |
| 3 | 0.073 | — | 1 |
| 9 | 0.078 | — | 1 |
| 11 (comparator) | 0.138 | 0.050 | 3 |
| 3A | 0.059 | — | 1 |
| 17 | 0.155 | — | 1 |
| 14 | 0.101 | 0.008 | 2 |
| 3B | 0.172 | — | 1 |
| 21 | 0.061 | — | 1 |
| 22 | 0.027 | — | 1 |
| 22A | 0.027 | — | 1 |
| 22B | 0.005 | — | 1 |
| 23 | 0.016 | 0.002 | 4 |
| 24 | 0.007 | 0 | 4 |
| 25 | 0.013 | 0.002 | 5 |
| 26 | 0.011 | 0.004 | 4 |
| WO2007/084786 Example 10 | 0.548 | 0.034 | 20 |
| WO2007/084786 Example 331 | 5.220 | * | 2 |
| WO2007/084786 Example 17 | 1.030 | — | 1 |
| WO2007/084786 Example 324 | 6.540 | 0.040 | 2 |
| WO2007/084786 Example 18 | 1.290 | — | 1 |
| WO2007/084786 Example 344 | 2.768 | 0.184 | 4 |
| WO2007/084786 Example 85 | 0.238 | 0.065 | 4 |

* The second value was >10. Therefore no SEM calculation was possible.

Cellular assay mTOR

| Example no. | mTOR S6K(T389)_TSC1ko/ IC50 [umol I-1] | SEM | n |
|---|---|---|---|
| 18 | 0.794 | 0.070 | 7 |
| 15 | 0.727 | * | 2 |
| 1 | 0.964 | 0.228 | 3 |
| 4 | 0.647 | 0.013 | 2 |
| 10 | 2.020 | ** | 4 |
| 19 | 0.423 | 0.050 | 2 |
| 13 | 1.950 | — | 1 |
| 20 | >2.27 |  | 8 |
| 6 | 0.574 | 0.100 | 4 |
| 8 | 0.994 | — | 1 |
| 5 | 1.41 | 0.05 | 2 |
| 16 | 0.942 |  | 4 |
| 7 | 1.23 | 0.09 | 2 |
| 12 | 1.100 | — | 1 |
| 3 | 0.759 | 0.048 | 2 |
| 9 | 1.260 | * | 2 |
| 11 (comparator) | 1.410 | *** | 5 |
| 3A | 1.570 | 0.170 | 2 |
| 17 | 0.867 | — | 1 |

-continued

Cellular assay mTOR

| Example no. | mTOR S6K(T389)_TSC1ko/ IC50 [umol l-1] | SEM | n |
|---|---|---|---|
| 14 | >2.27 | **** | 3 |
| 3B | 1.111 | 0.230 | 2 |
| 21 | 0.942 | 0.025 | 2 |
| 22 | 1.386 | 0.734 | 2 |
| 22A | 2.120 | 0.730 | 2 |
| 22B | 2.3 | — | 1 |
| 23 | 1.111 | 0.320 | 2 |
| 24 | 1.830 | — | 1 |
| 25 | 1.830 | — | 1 |
| 26 | 0.857 | — | 1 |
| WO2007/084786 Example 10 | 0.602 | 0.067 | 10 |
| WO2007/084786 Example 331 | >2.27 | **** | 4 |
| WO2007/084786 Example 17 | 2.120 | * | 2 |
| WO2007/084786 Example 324 | >2.27 | **** | 4 |
| WO2007/084786 Example 18 | >2.27 | **** | 2 |
| WO2007/084786 Example 344 | >2.27 | **** | 3 |
| WO2007/084786 Example 85 | 1.001 | 0.055 | 3 |

\* the second value was >2.27. Therefore no SEM calculation was possible.
\*\* 3 of the 4 values were >2.27. Therefore no SEM calculation was possible.
\*\*\* 3 of the 5 values were >2.27. Therefore no SEM calculation was possible.
\*\*\*\* All values were >2.27. Therefore no SEM calculation was possible.

The off-target effect (evidence of tubulin binding) was measured as follows.

Cytospin Assay Description:

Cell cycle G2/M arrest Cytospin assay to detect tubulin binding (off-target) binding activities of MAPP derivatives: $5 \times 10^5$ cells A2058 cells were plated in 6-well cluster, with 2 mL of DMEM (high Glucose containing 1% sodium pyruvate, 1% glutamin and 10% FCS). 18 hours later, the test items were added at a concentration of 5 µM (spiking 1 µL of a 10 mM solution of the test item). 24 hours later, the cells were trypsinized and transferred into a 15 mL conical tube. Cells are then pelleted by centrifugation, and resuspended with PBS/0 (containing 10% FCS). Cells are counted with a CASY counter, and each samples equilibrated to $1 \times 10^6$ cells/mL. 200 µL ($2 \times 10^5$ cells) were then transferred to 1.5 mL Cytospin tubes (Heraeus Sepatec, Ref 1152), and centrifuged for 5 min at 50×g at 4° C., with a Cytospin system, containing a Sepatech system (Heraeus, Ref #3425), adjusted on top of a microscope slide (Thermo-Scientific, Ref:#PH040820. Cells were then fixed for 15 min at room temperature, and stained with the Diff Quick® assay (Medion Diagnostics, Ref: #130832), following the recommendations of the manufacturer. Condensed DNA reflecting the G2/M arrest is revealed by punctuated staining in the cells, when examining the slides under the microscope. The staining was visually assessed for the presence of condensed DNA and given a score where 0=no condensed DNA observed (indicating no off target activity), 1=(indicating weak off target activity), 2=(indicating medium off target activity), 3=large amount of condensed DNA observed (indicating strong off-target activity).

The data obtained using this method is shown in the following table:

| Example no. | Score |
|---|---|
| 18 | 0 |
| 15 | 0 |
| 1 | 0 |
| 4 | 0 |
| 10 | 0 |
| 19 | 0 |
| 13 | 0 |
| 20 | 1-2 |
| 6 | 0 |
| 8 | 0 |
| 5 | 0 |
| 16 | 0 |
| 7 | n.d. |
| 12 | 0 |
| 2 | n.d. |
| 3 | 0 |
| 9 | n.d. |
| 11 (comparator) | 3 |
| 3A | 0 |
| 17 | 0 |
| 14 | 0 |
| 3B | 0 |
| 21 | 0 |
| 22 | 0 |
| 22A | n.d. |
| 22B | n.d. |
| 23 | 0 |
| 24 | 0 |
| 25 | 0 |
| 26 | 0 |
| WO2007/084786 Example 10 | 3 |
| WO2007/084786 Example 331 | 0 |
| WO2007/084786 Example 17 | 0 |
| WO2007/084786 Example 324 | 0 |
| WO2007/084786 Example 18 | 0 |
| WO2007/084786 Example 344 | 0 |
| WO2007/084786 Example 85 | 3 | n.d. = not done

What is claimed is:

1. A compound of Formula (I)

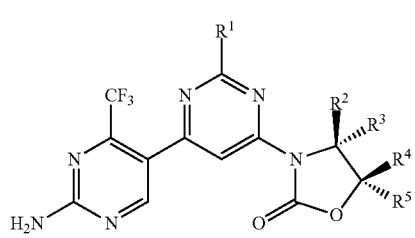

(I)

wherein,
$R^1$ is

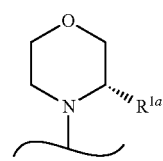

wherein $R^{1a}$ is H or —$CH_3$ or R¹ is

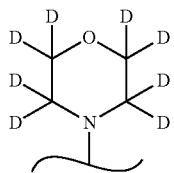

wherein D is deuterium;
R² is H;
R³ is H;
R⁴ is H, and R⁵ is —CH₃ or —CH₂OH; or
R⁴ is —CH₂OH, and R⁵ is H;
or
R² is —CH₃, —CH₂OH, —CH₂OCH₃, —CH₂CH₂OH or —CH₂OC(O)H;
R³ is H;
R⁴ is —CH₃, —CH₂OH, —CH₂CH₂OH, —CH₂CH(OH)CH₃ or —CH₂C(OH)(CH₃)₂ and R⁵ is H, or
R⁴ is H, and R⁵ is —CH₃, —CH₂OH, —CH₂CH(OH)CH₃ or —CH₂C(OH)(CH₃)₂, or
R⁴ is H or —CH₃ and R⁵ is H or —CH₃;
or
R³ is H;
R⁴ is H;
R² and R⁵ are joined and form —(CH₂)₄—;
or
R⁴ is H;
R⁵ is H; and
R² is —CH₂OH, and R³ is —CH₃; or
R² is H or —CH₃, and R³ is —CH₂OH;
or
R² is H;
R⁴ is H; and
R³ and R⁵ are joined and form the group

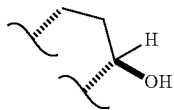

or the group

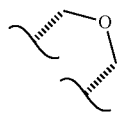

or
R³ is H;
R⁵ is H; and
R² and R⁴ are joined and form the group

or a pharmaceutically acceptable salt thereof.

2. The compound according to claim 1, wherein,
R² is —CH₃, —CH₂OH, —CH₂OCH₃, —CH₂CH₂OH or —CH₂OC(O)H;
R³ is H;
R⁴ is —CH₃, —CH₂OH or —CH₂CH₂OH, and R⁵ is H, or
R⁴ is H, and R⁵ is —CH₃ or —CH₂OH, or
R⁴ is H or —CH₃ and R⁵ is H or —CH₃;
or
R³ is H;
R⁴ is H;
R² and R⁵ is —(CH₂)₄—;
or
R⁴ is H;
R⁵ is H; and
R² is —CH₂OH, and R³ is —CH₃; or
R² is H or —CH₃, and R³ is —CH₂OH,
or a pharmaceutically acceptable salt thereof.

3. The compound according to claim 1, wherein,
R² is —CH₃, —CH₂OH, —CH₂OCH₃, —CH₂CH₂OH or —CH₂OC(O)H;
R³ is H;
R⁴ is —CH₃, —CH₂OH or —CH₂CH₂OH, and R⁵ is H, or
R⁴ is H, and R⁵ is —CH₃ or —CH₂OH, or
R⁴ is H or —CH₃ and R⁵ is H or —CH₃;
or
R⁴ is H;
R⁵ is H; and
R² is —CH₂OH, and R³ is —CH₃; or
R² is H or —CH₃, and R³ is —CH₂OH,
or a pharmaceutically acceptable salt thereof.

4. The compound according to claim 1, wherein,
R² is —CH₃, —CH₂OH, —CH₂OCH₃, —CH₂CH₂OH or —CH₂OC(O)H;
R³ is H;
R⁴ is —CH₃, —CH₂OH or —CH₂CH₂OH, and R⁵ is H, or
R⁴ is H, and R⁵ is —CH₃ or —CH₂OH, or
R⁴ is H or —CH₃ and R⁵ is H or —CH₃,
or a pharmaceutically acceptable salt thereof.

5. The compound according to claim 1, of formula (IA')

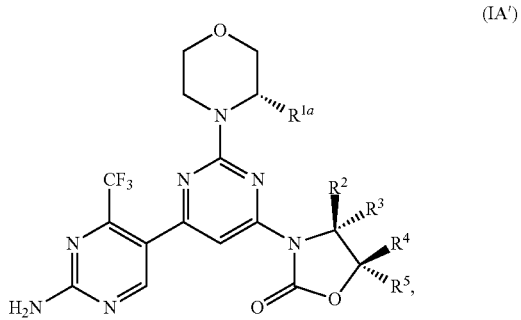

(IA')

wherein R¹ᵃ is H or —CH₃
or a pharmaceutically acceptable salt thereof.

6. The compound according to claim 1, of formula (IA):

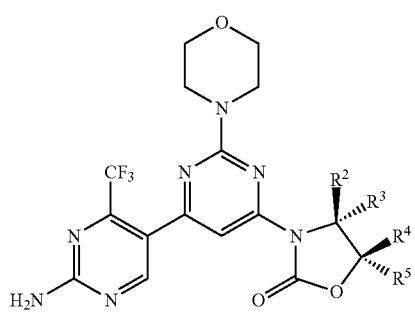

(IA)

wherein,
R² is —CH₃, —CH₂OH, —CH₂OCH₃, —CH₂CH₂OH or —CH₂OC(O)H;
R³ is H;
R⁴ is —CH₃, —CH₂OH or —CH₂CH₂OH, and R⁵ is H, or
R⁴ is H, and R⁵ is —CH₃ or —CH₂OH, or
R⁴ is H or —CH₃ and R⁵ is H or —CH₃,
or a pharmaceutically acceptable salt thereof.

7. The compound according to claim 6, wherein
R² is —CH₃ or —CH₂OH;
R³ is H;
R⁴ is —CH₃, —CH₂OH or —CH₂CH₂OH, and R⁵ is H, or
R⁴ is H, and R⁵ is —CH₃ or —CH₂OH, or
R⁴ is H or —CH₃ and R⁵ is H or —CH₃,
or a pharmaceutically acceptable salt thereof.

8. The compound according to claim 7, wherein
R² is —CH₃ or —CH₂OH;
R³ is H;
R⁴ is —CH₃, —CH₂OH or —CH₂CH₂OH and R⁵ is H or
R⁴ is H and R⁵ is CH₃ or —CH₂OH,
or a pharmaceutically acceptable salt thereof.

9. The compound, or a pharmaceutically acceptable salt thereof, according to claim 1 which is selected from
(S)-3-(2'-Amino-2-morpholin-4-yl-4'-trifluoromethyl-[4,5']bipyrimidinyl-6-yl)-4-methyl-oxazolidin-2-one,
(S)-3-(2'-Amino-2-morpholin-4-yl-4'-trifluoromethyl-[4,5']bipyrimidinyl-6-yl)-4-hydroxymethyl-5,5-dimethyl-oxazolidin-2-one,
racemic 3-(2'-amino-2-morpholino-4'-(trifluoromethyl)-4,5'-bipyrimidin-6-yl)-4-(hydroxymethyl)-4-methyloxazolidin-2-one,
(S)-3-(2'-amino-2-morpholino-4'-(trifluoromethyl)-4,5'-bipyrimidin-6-yl)-4-(hydroxymethyl)-4-methyloxazolidin-2-one (absolute stereochemistry not determined),
(R)-3-(2'-amino-2-morpholino-4'-(trifluoromethyl)-4,5'-bipyrimidin-6-yl)-4-(hydroxymethyl)-4-methyloxazolidin-2-one (absolute stereochemistry not determined),
(3aS,7aS)-3-(2'-Amino-2-morpholin-4-yl-4'-trifluoromethyl-[4,5']bipyrimidinyl-6-yl)-hexahydro-benzooxazol-2-one,
(S)-3-(2'-Amino-2-morpholin-4-yl-4'-trifluoromethyl-[4,5']bipyrimidinyl-6-yl)-4-methoxymethyl-oxazolidin-2-one,
(4S,5S)-3-(2'-Amino-2-morpholin-4-yl-4'-trifluoromethyl-[4,5']bipyrimidinyl-6-yl)-4-hydroxymethyl-5-methyl-oxazolidin-2-one,
(S)-3-(2'-Amino-2-morpholin-4-yl-4'-trifluoromethyl-[4,5']bipyrimidinyl-6-yl)-4-hydroxymethyl-oxazolidin-2-one,
(4S,5R)-3-(2'-Amino-2-(D8-morpholin-4-yl)-4'-trifluoromethyl-[4,5']bipyrimidinyl-6-yl)-4-hydroxymethyl-5-methyl-oxazolidin-2-one,
(S)-3-(2'-Amino-2-morpholin-4-yl-4'-trifluoromethyl-[4,5']bipyrimidinyl-6-yl)-4-(2-hydroxy-ethyl)-oxazolidin-2-one,
(4S,5R)-3-[2'-Amino-2-((S)-3-methyl-morpholin-4-yl)-4'-trifluoromethyl-[4,5']bipyrimidinyl-6-yl]-4-hydroxymethyl-5-methyl-oxazolidin-2-one,
Formic acid (4S,5R)-3-(2'-amino-2-morpholin-4-yl-4'-trifluoromethyl-[4,5']bipyrimidinyl-6-yl)-5-methyl-2-oxo-oxazolidin-4-ylmethyl ester,
(S)-3-[2'-Amino-2-((S)-3-methyl-morpholin-4-yl)-4'-trifluoromethyl-[4,5']bipyrimidinyl-6-yl]-4-methyl-oxazolidin-2-one,
(S)-3-(2'-Amino-2-morpholin-4-yl-4'-trifluoromethyl-[4,5']bipyrimidinyl-6-yl)-5-hydroxymethyl-oxazolidin-2-one,
(4S,5R)-3-(2'-Amino-2-morpholin-4-yl-4'-trifluoromethyl-[4,5']bipyrimidinyl-6-yl)-5-hydroxymethyl-4-methyl-oxazolidin-2-one,
(S)-3-(2'-Amino-2-morpholin-4-yl-4'-trifluoromethyl-[4,5']bipyrimidinyl-6-yl)-5-methyl-oxazolidin-2-one,
(S)-3-(2'-amino-2-D8-morpholino-4'-(trifluoromethyl)-[4,5'-bipyrimidin]-6-yl)-4-methyloxazolidin-2-one,
(4S,5R)-3-(2'-Amino-2-morpholin-4-yl-4'-trifluoromethyl-[4,5']bipyrimidinyl-6-yl)-4-hydroxymethyl-5-methyl-oxazolidin-2-one,
(4S,5S)-3-(2'-Amino-2-morpholin-4-yl-4'-trifluoromethyl-[4,5']bipyrimidinyl-6-yl)-5-hydroxymethyl-4-methyl-oxazolidin-2-one,
(R)-3-(2'-Amino-2-morpholin-4-yl-4'-trifluoromethyl-[4,5']bipyrimidinyl-6-yl)-5-hydroxymethyl-oxazolidin-2-one,
(3aR,6aR)-3-(2'-amino-2-morpholino-4'-(trifluoromethyl)-[4,5'-bipyrimidin]-6-yl)-tetrahydrofuro[3,4-d]oxazol-2(3H)-one,
racemic (3aR*,6R*,6aR*)-3-(2'-Amino-2-morpholino-4'-(trifluoromethyl)-[4,5'-bipyrimidin]-6-yl)-6-hydroxy-hexahydro-2H-cyclopenta[d]oxazol-2-one,
(3aR,6R,6aR)-(Z-Amino-2-morpholino-4'-(trifluoromethyl)-[4,5'-bipyrimidin]-6-yl)-6-hydroxyhexahydro-2H-cyclopenta[d]oxazol-2-one,
(3aS,6S,6aS)-(Z-Amino-2-morpholino-4'-(trifluoromethyl)-[4,5'-bipyrimidin]-6-yl)-6-hydroxyhexa-hydro-2H-cyclopenta[d]oxazol-2-one, or
(4S,5R)-3-(2'-Amino-2-morpholino-4'-(trifluoromethyl)-[4,5'-bipyrimidin]-6-yl)-5-(2-hydroxyethyl)-4-methyloxazolidin-2-one.

10. A compound, or a pharmaceutically acceptable salt thereof, selected from
(4S,5R)-3-[2'-Amino-2-((S)-3-methyl-morpholin-4-yl)-4'-trifluoromethyl-[4,5']bipyrimidinyl-6-yl]-4-hydroxymethyl-5-methyl-oxazolidin-2-one,
(4S,5R)-3-(2'-Amino-2-morpholin-4-yl-4'-trifluoromethyl-[4,5']bipyrimidinyl-6-yl)-4-hydroxymethyl-5-methyl-oxazolidin-2-one, or
(4S,5R)-3-(2'-Amino-2-morpholino-4'-(trifluoromethyl)-[4,5'-bipyrimidin]-6-yl)-5-(2-hydroxyethyl)-4-methyloxazolidin-2-one.

11. A pharmaceutical composition comprising a therapeutically effective amount of a compound according to claim 1, or a pharmaceutically acceptable salt thereof, and one or more pharmaceutically acceptable carriers.

12. A combination comprising a therapeutically effective amount of a compound according to claim 1, or a pharmaceutically acceptable salt thereof, and one or more additional therapeutically active agents.

13. A method of treating in a patent with cancer selected from a group consisting of HER2 positive breast cancer, solid tumors and non-small cell lung cancer comprising administering to a subject a therapeutically effective amount of a compound, or a pharmaceutically acceptable salt thereof, according to claim 1.

14. A pharmaceutical composition comprising a therapeutically effective amount of a compound according to claim 9, or a pharmaceutically acceptable salt thereof, and one or more pharmaceutically acceptable carriers.

15. A combination comprising a therapeutically effective amount of a compound according to claim 9, or a pharmaceutically acceptable salt thereof, and one or more additional therapeutically active agents.

16. A method of treating in a patient with cancer selected from the group consisting of HER2 positive breast cancer, solid tumors and non-small cell lung cancer comprising administering to a subject a therapeutically effective amount of a compound, or a pharmaceutically acceptable salt thereof, according to claim 9.

17. A pharmaceutical composition comprising a therapeutically effective amount of a compound according to claim 10, or a pharmaceutically acceptable salt thereof, and one or more pharmaceutically acceptable carriers.

18. A combination comprising a therapeutically effective amount of a compound according to claim 10, or a pharmaceutically acceptable salt thereof, and one or more additional therapeutically active agents.

19. A method of treating in a patient with cancer selected from the group consisting of HER2 positive breast cancer, solid tumors and non-small cell lung cancer comprising administering to a subject a therapeutically effective amount of a compound, or a pharmaceutically acceptable salt thereof, according to claim 10.

20. A compound (4S,5R)-3-[2'-Amino-2-((S)-3-methyl-morpholin-4-yl)-4'-trifluoromethyl-[4,5']bipyrimidinyl]-6-yl]-4-hydroxymethyl-5-methyl-oxazolidin-2-one.

21. A compound (4S,5R)-3-(2'-Amino-2-morpholin-4-yl-4'-trifluoromethyl-[4,5']bipyrimidinyl-6-yl)-4-hydroxymethyl-5-methyl-oxazolidin-2-one.

22. A compound (4S,5R)-3-(2'-Amino-2-morpholino-4'-(trifluoromethyl)-[4,5'-bipyrimidin]-6-yl)-5-(2-hydroxyethyl)-4-methyloxazolidin-2-one.

* * * * *